US011365195B2

(12) United States Patent
Newman et al.

(10) Patent No.: US 11,365,195 B2
(45) Date of Patent: Jun. 21, 2022

(54) ATYPICAL INHIBITORS OF MONOAMINE TRANSPORTERS; METHOD OF MAKING; AND USE THEREOF

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Amy Hauck Newman, Phoenix, MD (US); JoLynn Barbara Giancola, Boardman, OH (US); Rachel D. Slack, Baltimore, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/762,998

(22) PCT Filed: Nov. 12, 2018

(86) PCT No.: PCT/US2018/060260
§ 371 (c)(1),
(2) Date: May 11, 2020

(87) PCT Pub. No.: WO2019/094856
PCT Pub. Date: May 16, 2019

(65) Prior Publication Data
US 2021/0024523 A1    Jan. 28, 2021

Related U.S. Application Data

(60) Provisional application No. 62/585,058, filed on Nov. 13, 2017.

(51) Int. Cl.
*C07D 471/10* (2006.01)
*C07D 211/58* (2006.01)
*C07D 241/04* (2006.01)

(52) U.S. Cl.
CPC .......... *C07D 471/10* (2013.01); *C07D 211/58* (2013.01); *C07D 241/04* (2013.01)

(58) Field of Classification Search
CPC ................ C07D 471/10; C07D 211/58; C07D 241/04
USPC ....................................................... 514/278
See application file for complete search history.

(56) References Cited

U.S. PATENT DOCUMENTS

| 2,483,671 | A | 10/1949 | Rieveschl, Jr. et al. |
| 2,618,637 | A | 11/1952 | Archer et al. |
| 2,621,214 | A | 12/1952 | Deinet |
| 3,043,844 | A | 7/1962 | Elpern |
| 3,128,308 | A | 4/1964 | Dou et al. |
| 3,238,209 | A * | 3/1966 | Nakanishi .......... C07D 295/088 544/397 |
| 4,066,686 | A | 1/1978 | Lafon |
| 4,177,290 | A | 12/1979 | Lafon |
| 4,866,062 | A | 9/1989 | Toth et al. |
| 4,927,855 | A | 5/1990 | Lafon |
| 5,324,728 | A | 6/1994 | Sekine et al. |
| 6,387,389 | B1 | 5/2002 | Rothman et al. |
| 8,163,907 | B2 | 4/2012 | Chen et al. |
| 9,862,679 | B2 * | 1/2018 | Newman ............... C07C 317/44 |
| 10,590,074 | B2 * | 3/2020 | Newman ................ A61K 45/06 |
| 10,913,711 | B2 * | 2/2021 | Newman ................ A61P 25/00 |
| 2005/0222257 | A1 | 10/2005 | Rebiere et al. |
| 2008/0319227 | A1 | 12/2008 | Liang et al. |
| 2010/0226943 | A1 | 9/2010 | Brennan et al. |
| 2016/0009644 | A1 | 1/2016 | Newman et al. |
| 2018/0093947 | A1 | 4/2018 | Newman |
| 2019/0185424 | A1 | 6/2019 | Newman et al. |

FOREIGN PATENT DOCUMENTS

| BE | 633453 | 12/1963 |
| CH | 358080 | 12/1961 |
| DE | 4219659 A1 | 12/1993 |

(Continued)

OTHER PUBLICATIONS

Boos et al, "Str-activity relationships of sub. N-benxylpiperidines in the GBR series: Syn. of 4-(2-bis(4-fluorophenyl)methoxy)ethyl)-1-(2-trifluoromethylbenzyl) piperidine, an allosteric modulator of the serotonin transp.", Bio&Med Ch, 2006 14:11 67-73.

Cao et al., "SARs at the Monoamine Transporters for a Novel Series of Modafinil Analogues", ACS Medicinal Chemistry Letters; 2011, 2, 48-52.

Cao, Jianjing et al.; "Novel and High Affinity 2-[(Diphenylmethyl)sulfinyl]acetamide (Modafinil) Analogues as Atypical Dopamine Transporter Inhibitors"; Journal of Medicinal Chemistry, v. 59, 2016, p. 10676-10691.

CAS Registry No. 1082413-02-2; STN Entry Date Dec. 9, 2008.
CAS Registry No. 1090672-47-1; STN Entry Date Dec. 28, 2008.
CAS Registry No. 1099264-80-8; STN Entry Date Feb. 2, 2009.
CAS Registry No. 1223264-74-1; STN Entry Date May 14, 2010.

(Continued)

*Primary Examiner* — Taofiq A Solola
(74) *Attorney, Agent, or Firm* — McBee Moore & Vanik IP, LLC

(57) ABSTRACT

Disclosed herein are a series of modafinil analogue compounds that bind with moderate to high affinity to the dopamine (DA) transporter (DAT) and several analogues also having affinity for the serotonin (5-HT) transporter (SERT) and/or sigma-1 receptor. Employing aminopiperidine, piperidineamino, spirobicyclodiaza, or substituted piperazine functional groups, desired dopamine transporter affinity has been retained along with improved metabolic stability over unsubstituted piperazine ring analogues. Importantly, these compounds have no predicted addictive liability. Also disclosed are methods for treating substance use disorders as well as other neuropsychiatric disorders such as ADHD, depression, narcolepsy, and cognitive impairment.

17 Claims, 1 Drawing Sheet

(56) References Cited

FOREIGN PATENT DOCUMENTS

| | | | |
|---|---|---|---|
| EP | 0097071 A1 | 12/1983 | |
| EP | 0097546 B1 | 9/1985 | |
| EP | 0256909 A1 | 2/1988 | |
| EP | 0318093 A2 | 11/1988 | |
| EP | 0399818 A1 | 11/1990 | |
| EP | 0458387 A1 | 11/1991 | |
| EP | 0528172 A1 | 2/1993 | |
| GB | 890732 | 3/1962 | |
| NL | 105432 | 7/1963 | |
| WO | 9501171 A1 | 1/1995 | |
| WO | 2003037853 A1 | 5/2003 | |
| WO | 03066035 A2 | 8/2003 | |
| WO | 2006010627 A1 | 2/2006 | |
| WO | 2007071035 A1 | 6/2007 | |
| WO | WO-2007071035 A1 * | 6/2007 | ........... C07D 211/62 |
| WO | WO-2007117961 A2 * | 10/2007 | ........... C07D 403/06 |
| WO | 2011026240 A1 | 3/2011 | |
| WO | 2013007698 A1 | 1/2013 | |
| WO | 2014138518 A2 | 9/2014 | |
| WO | WO-2014138518 A2 * | 9/2014 | ........... C07C 323/60 |

OTHER PUBLICATIONS

CAS Registry No. 1280997-84-3; STN Entry Date Apr. 17, 2011.
CAS Registry No. 1281038-18-3; STN Entry Date Apr. 17, 2011.
CAS Registry No. 1288696-95-6; STN Entry Date May 1, 2011.
CAS Registry No. 1295343-48-4; STN Entry Date May 16, 2011.
CAS Registry No. 1301333-25-4; STN Entry Date May 27, 2011.
CAS Registry No. 1333942-87-2; STN Entry Date Sep. 29, 2011.
CAS Registry No. 1349277-69-5; STN Entry Date Dec. 5, 2011.
CAS Registry No. 1350210-59-1; STN Entry Date Dec. 7, 2011.
CAS Registry No. 1371367-22-4; STN Entry Date Apr. 30, 2012.
CAS Registry No. 1371384-62-1; STN Entry Date Apr. 30, 2012.
CAS Registry No. 1385862-91-8; STN Entry Date Aug. 8, 2012.
CAS Registry No. 1386713-46-7; STN Entry Date Aug. 6, 2012.
CAS Registry No. 1387276-96-1; STN Entry Date Aug. 7, 2012.
CAS Registry No. 1388402-86-5; STN Entry Date Aug. 9, 2012.
CAS Registry No. 1388517-81-4; STN Entry Date Aug. 9, 2012.
CAS Registry No. 1389532-00-6; STN Entry Date Aug. 12, 2012.
CAS Registry No. 1389931-46-7; STN Entry Date Aug. 12, 2012.
CAS Registry No. 1389994-56-2; STN Entry Date Aug. 12, 2012.
CAS Registry No. 1390017-95-4; STN Entry Date Aug. 12, 2012.
CAS Registry No. 1390603-82-3; STN Entry Date Aug. 13, 2012.
CAS Registry No. 145701-76-4; STN Entry Date Feb. 4, 1993.
CAS Registry No. 15515-59-0; STN Entry Date Nov. 16, 1984.
CAS Registry No. 1581413-06-0; STN Entry Date Apr. 7, 2014.
CAS Registry No. 1838248-96-6; STN Entry Date Dec. 29, 2015.
Darwish, M. et al.; "Investigation of a Possible Interaction Between Quetiapine and Armodafinil in Patients with Schizophrenia: An Open-Label, Multiple-Dose Study"; J Clin Pharmacol, 2012, vol. 52:9, p. 1399-1409.
Hiraide, S. et al.; "Behavioral effects on monoamine reuptake inhibitors on symptomatic domains in an animal model of attention-deficit/ hyperactivity disorder", 2013, vol. 105, pp. 89-97.
International Search Report for International Application No. PCT/US2018/060260, International Filing Date Nov. 12, 2018, dated Mar. 26, 2019, 9 pages.
JP05148222A; 19930615; English Abstract Only (1 page).
JP39012646 B4; 19640704; English Abstract Only (1 page).
JP39015839 B4; 19640805; English Abstract Only (1 page).
JP39019655 B4; 19640911; English Abstract Only (1 page).
JP39026553 B4; 19641121; English Abstract Only (1 page).
JP43013468 B4; 19680607; English Abstract Only (1 page).
Jung et al., "Simple Synthesis of Modafinil Derivatives and Their Anti-Inflammatory Activity", Molecules 2012, 17, 10446-10458.
Kharul et al., "Convenient Synthesis of Structurally Novel 1,3-Distributed Azetidine Derivatives", Synthetic Communications 2008, 38(11), 1703-1717.
Loland Claus J et al: "R-modafinil (armodafinil): a unique dopamine uptake inhibitor and potential medication for psychostimulant abuse", Biological Psychiatry, USA, vol. 72, No. 5, Sep. 1, 2012, pp. 405-413.
Mahler et al., "Modafinil attenuates reinstatement of cocaine seeking: role for cystine-glutamate exchange and metabrotropic glutamate receptors", Addiction Biology, Sep. 27, 2012, 1369-1600.
Matsushima et al., Osaka-shiritsu Daigaku Igaku Zasshi (1962), 11 379-92 English Abstract Only (1 page).
Metysova, J. et al.; "Farmakologicke vlasnosti nekolika analogu kaptodiaminu", Cesko-Slovenska Farmacie, 1963, vol. 12, pp. 448-450.
Minzenberg et al., "Modafinil: A Review of Neurochemical Actions and Effects on Cognition", Neuropsychopharmacology (2008) 33, 1477-1502.
Okunola et al., "Is Modafinil an Atypical Dopamine Uptake Inhibitor? ", Gordon Research Conference Catecholamines, Bates College, Lewiston, ME Aug. 2011, Abstract Only (2 pages).
Newman et al., "Atypical Dopamine Uptake Inhibitors that Provide Clues About Cocaine's Mechanism at the Dopamine Transporter", Top Med Chem (2009) 4: 95-129.
Patel et al., "Antimicrobial Activity of Piperazine Derivatives & Related Compounds"; Indian Journal of Experimental Biology (1971), 9(1), 117-119.
Reichel et al., "Chronic modafinil effects on drug-seeking following methamphetamine self-administration in rats", International Journal of Neuropsychopharmacology (2012), 15, 919-929.
Reichel et al., "Modafinil effects on reinstatement of methamphetamine seeking in a rat model of relapse", Psychopharmacology (2010) 210:337-346.
Schmitt et al., "The Atypical Stimulant and Nootropic Modafinil Interacts with the Dopamine Transporter in a Different Manner than Classical Cocaine-Like Inhibitors", PLoS ONE 2011, 6(10), e25790 (13 pages).
SciFinder Search Results; 2013; 13 pages.
Scoriels et al., "Modafinil effects on cognition and emotion in schizophrenia and is neurochemical modulation in the brain", Neuropharmacology 64 (2013) 168-184.
Sonurlikar et al., "Antifilarial Activity of N1, N4-Disubstituted Piperazine Derivatives", Bull Haff Instt, vol. 5, No. 3, 1977, 90-93.
Tahsili-Fahadan et al., Modafinil: an anti-relapse medication, Neuropharmacology Reviews, 2010, 35, 343-344.
Vaccari, A et al.; "Prenylamine derivatives as blockers of the vesicular transporter for dopamine. A quantitative structure-activity study"; European Journal of Medicinal Chemistry, vol. 32, 1997, p. 53-57.
Vadodaria et al., "Synthesis and Central Nervous System Depressant Activity of New Piperazine Derivatives and Related Compounds", CNS-Active Piperazines. III, Sep. 1969, pp. 860-865.
Written Opinion for International Application No. PCT/US2018/060260, International Filing Date Nov. 12, 2018, dated Mar. 26, 2019, 12 pages.
Zhang et al: "Synthesis and biological evaluation of (R)-N-(diarylmethylthio/sulfinyl)ethyl/propyl-piperidine-3-carboxylic acid hydrochlorides as novel GABA uptake inhibitors", Bioorganic & Med. Chem. Letters, vol. 17, No. 13, Jul. 1, 2007, pp. 3769-3773.
Zou et al., Journal of Medicinal Chemistry, 2006,49, 6391-6399.

* cited by examiner

ATYPICAL INHIBITORS OF MONOAMINE TRANSPORTERS; METHOD OF MAKING; AND USE THEREOF

CROSS-REFERENCE TO RELATED APPLICATIONS

This application is a National Stage application of PCT/US2018/060260 filed Nov. 12, 2018 and is related to, and claims the benefit of priority of, U.S. Provisional Patent Application No. 62/585,058 filed Nov. 13, 2017, the contents of each are incorporated herein by reference in their entirety for all purposes.

FIELD OF THE DISCLOSURE

The present disclosure is directed to modafinil analogue compounds useful as inhibitors of monoamine transporters.

BACKGROUND

The rapid reuptake of the monoaminergic neurotransmitters, dopamine (DA), serotonin (5-HT), and norepinephrine (NE) is described as the terminal step in the synaptic signaling. The reuptake of DA, 5-HT and NE into the presynaptic neuron is mediated by the dopamine transporter (DAT), serotonin transporter (SERT) and norepinephrine transporter (NET), respectively. Inhibition of DA reuptake is proposed to be the underlying mechanism of addictive psychostimulant drugs such as cocaine and methamphetamine.

Cocaine and methamphetamine are highly addictive psychostimulants, yet to date no pharmacological treatment has been FDA-approved for cocaine- or methamphetamine-use disorders. Like cocaine, the clinically available and wake-promoting drug modafinil (2-[(diphenylmethyl)sulfinyl]acetamide) binds to the dopamine transporter and blocks dopamine reuptake; however, unlike cocaine, it has low addictive potential. Methamphetamine also blocks DAT-mediated DA reuptake; however, similar to DA and dissimilar to cocaine, methamphetamine is a substrate for the DAT, and thus is taken into the cell and ultimately binds to the vesicular monoamine transporter (VMAT), releasing DA into the cell and reversing the DAT to efflux DA into the synaptic cleft. Although modafinil can compete with either cocaine or methamphetamine for binding to the DAT, it has been evaluated for the treatment of cocaine- or methamphetamine use disorders with mixed results.

Recently, a series of modafinil analogues have been synthesized and tested on intravenous methamphetamine self-administration in rats that were allowed short access (1 h; ShA) or long access (6 h; LgA) exposure to the drug. Although several analogues were effective, the analogue with highest binding affinity (Ki=2.6 nM) and selectivity for DAT had low efficacy in these models of methamphetamine taking, possibly due to its poor pharmacokinetics. More recently, this compound has demonstrated a behavioral profile that is psychostimulant-like and may thus have addictive liability, precluding its further development for the treatment of substance use disorders. Thus, there remains a need for high affinity DAT inhibitors with enhanced metabolic stability, but with no addictive liability, such that the compounds can be used for preclinical behavioral evaluation and development toward pharmacotherapeutic treatment of psychostimulant use disorders.

SUMMARY

In an embodiment is a compound of Formula I

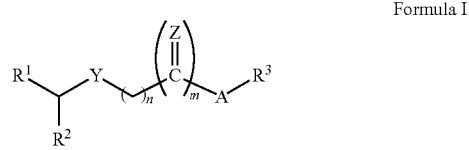

Formula I or a pharmaceutically acceptable salt thereof,
wherein $R^1$ and $R^2$ each independently is $C_6$-$C_{12}$ aryl, monocyclic heteroaryl, or bicyclic heteroaryl, each of which may be optionally substituted with 1, 2, or 3 substituents, each substituent independently selected from halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, or di-$C_1$-$C_2$ alkylamino;

Y is S, S(O), or S(O)$_2$;

n is 1, 2, or 3;

Z is O, S, or 2H;

m is 0 or 1;

A is one of A1 to A4

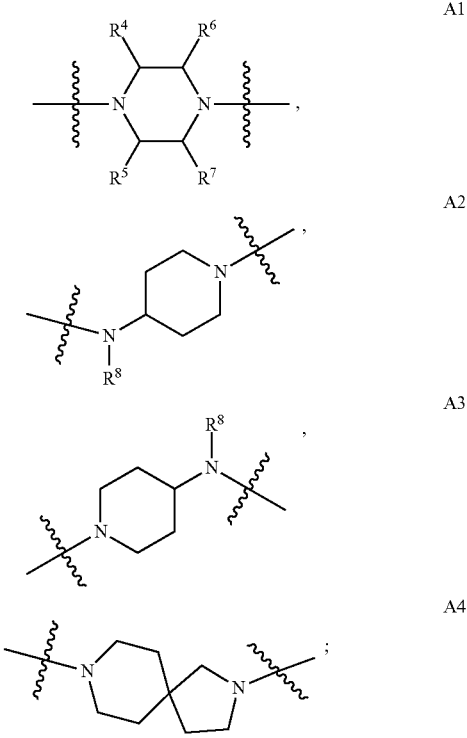

$R^4$, $R^5$, $R^6$, and $R^7$ each independently is hydrogen, $C_1$-$C_6$ alkyl, $C_2$-$C_6$ alkenyl, $C_1$-$C_6$ haloalkyl, or $C_2$-$C_6$ alkanoyl, with the proviso that at least one of $R^4$, $R^5$, $R^6$, and $R^7$ is other than hydrogen;

$R^8$ is hydrogen, $C_1$-$C_6$ alkyl, $C_1$-$C_6$ haloalkyl, or $C_2$-$C_6$ alkanoyl; and $R^3$ is hydrogen, $C_1$-$C_8$ alkyl, $C_1$-$C_6$ haloalkyl, $C_2$-$C_6$ alkenyl, $C_3$-$C_7$ cycloalkyl, $C_2$-$C_6$ alkanoyl, aryl-(C=O)—, monocyclic heteroaryl-(C=O)—, bicyclic heteroaryl-(C=O)—, (C$_3$-C$_7$ cycloalkyl)C$_0$-C$_6$ alkyl, (C$_3$-C$_7$ cycloalkenyl)C$_0$-C$_6$ alkyl, (heterocycloalkyl)C$_0$-C$_6$ alkyl, (heterocycloalkenyl)C$_0$-C$_6$ alkyl, (aryl)C$_0$-C$_6$ alkyl, (monocyclic heteroaryl)C$_0$-C$_6$ alkyl, (bicyclic heteroaryl)C$_0$-C$_6$ alkyl, or (C$_2$-C$_6$ alkanoyl)C$_0$-C$_6$ alkyl, wherein each alkyl independently can optionally be substituted with 1 or 2 substituents and each aryl and heteroaryl independently can optionally be substituted with 1, 2, or 3 substituents, wherein each substituent is independently selected from halogen, hydroxyl, amino, nitro, cyano, C$_1$-C$_6$ alkyl, C$_2$-C$_6$ alkenyl, C$_1$-C$_6$ alkoxy, C$_1$-C$_6$ haloalkyl, C$_1$-C$_6$ haloalkoxy, —COOH, —CHO, —CONH$_2$, C$_2$-C$_6$ alkanoyl, mono-C$_1$-C$_2$ alkylamino, di-C$_1$-C$_2$ alkylamino, or phenyl, wherein the phenyl can optionally be substituted with halogen, hydroxyl, amino, nitro, cyano, C$_1$-C$_6$ alkyl, C$_2$-C$_6$ alkenyl, C$_1$-C$_6$ alkoxy, C$_1$-C$_6$ haloalkyl, C$_1$-C$_6$ haloalkoxy, —COOH, —CHO, —CONH$_2$, C$_2$-C$_6$ alkanoyl, mono-C$_1$-C$_2$ alkylamino, or di-C$_1$-C$_2$ alkylamino;

with the proviso that when A is A2, R$^1$ and R$^2$ are each phenyl, Y is S, n is 1, m is 1, Z is O, and R$^8$ is methyl, then either i) R$^3$ is other than hydrogen or unsubstituted C$_1$-C$_8$ alkyl, or ii) both R$^1$ and R$^2$ have at least one substituent.

In an embodiment, a pharmaceutical composition comprises a compound of Formula I or a salt thereof and at least one pharmaceutically acceptable carrier.

In an embodiment, a method for eliciting a wake-promoting, cognition-enhancing or mood-enhancing effect comprises providing a therapeutically effective amount of a compound of Formula I or salt thereof, optionally in the form of a pharmaceutical composition, to a patient in need of such treatment.

In an embodiment, a method for treating substance use disorders, attention deficit (hyperactivity) disorder, depressive disorders, sleep disorders or cognitive impairment comprises providing a therapeutically effective amount of a compound of Formula I or salt thereof to a patient in need of such treatment.

DETAILED DESCRIPTION

Figure 1:
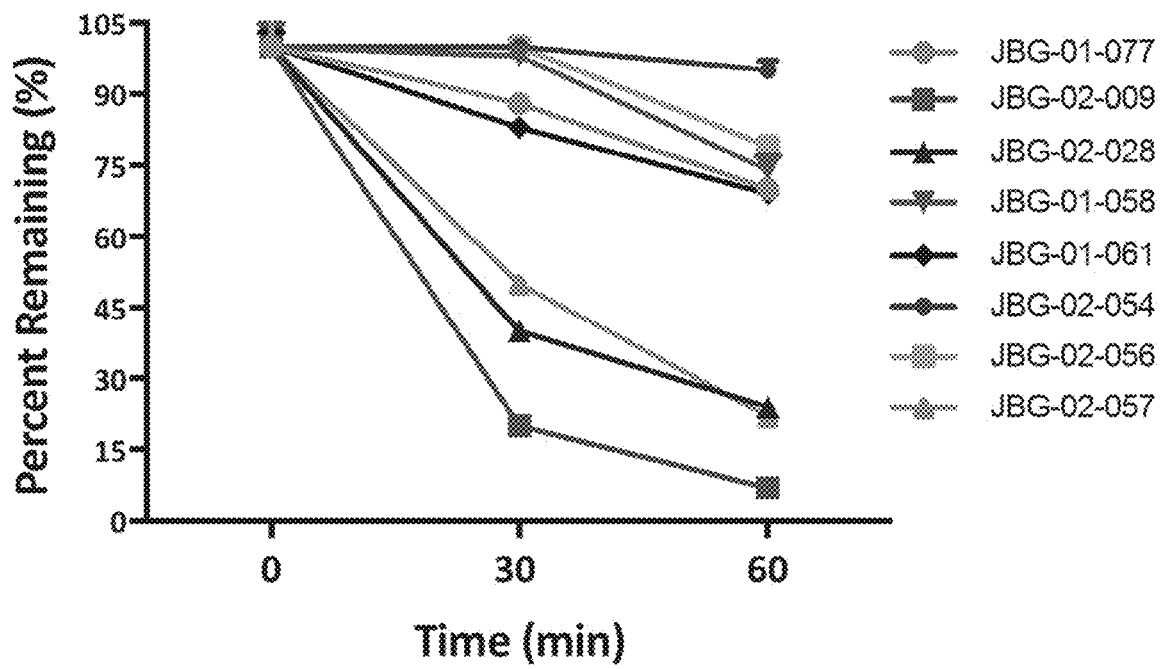
FIG. 1: Phase I metabolic stability assay results for aminopiperidine and piperidineamino analogues.

Disclosed herein are a series of novel and atypical inhibitors of monoamine transporters. These compounds bind with moderate to high affinity to the DAT and several analogues also have affinity for the serotonin transporter (SERT) and/or sigma-1 receptor. Employing aminopiperidine, piperidineamino, spirobicyclodiaza, or substituted piperazine functional groups, desired DAT affinity has been retained along with improved metabolic stability over unsubstituted piperazine ring analogues. The increase in sigma-1 receptor and SERT affinities may improve the efficacy of these compounds in attenuating substance use disorders and preventing relapse. Because these compounds stabilize the DAT in a conformation unlike cocaine, they do not produce cocaine-like behavioral effects, which limit their addictive liability and improves their therapeutic potential for treatment of substance use disorders, as well as other neuropsychiatric disorders such as ADHD, depression, cognitive impairment, and narcolepsy. In addition, many patients who suffer from depressive disorders do not benefit from the clinically available selective serotonin reuptake inhibitors (SSRIs) or tricyclic antidepressants (TCAs). It has been suggested that these patients may experience a hypodopaminergic state that prevents this typical treatment regimen from being effective. Compounds such as those according to Formula I will, in addition to elevating serotonin levels through inhibition of the SERT, elevate dopamine levels through inhibition of the DAT may be extremely useful for this patient population.

Also provided are pharmaceutical compositions comprising a compound of Formula I and a pharmaceutically acceptable carrier. Such pharmaceutical compositions may contain a compound of Formula I as the only active agent or may contain a combination of a compound of Formula I and another pharmaceutically active agent. Also provided are methods for eliciting a wake-promoting, cognition-enhancing or mood-enhancing effect and for treating substance use disorders, attention deficit (hyperactivity) disorder, depressive disorders, sleep disorders or cognitive impairment to a patient in need of such treatment by administration of a compound of Formula I or a pharmaceutical composition comprising a compound of Formula I.

A compound of Formula I:

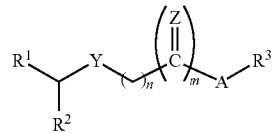

Formula I or a pharmaceutically acceptable salt thereof, wherein

R$^1$ and R$^2$ each independently are C$_6$-C$_{12}$ aryl, monocyclic heteroaryl, or bicyclic heteroaryl, each of which may be optionally substituted with 1, 2, or 3 substituents, each substituent independently selected from halogen, hydroxyl, amino, nitro, cyano, C$_1$-C$_6$ alkyl, C$_2$-C$_6$ alkenyl, C$_1$-C$_6$ alkoxy, C$_1$-C$_6$ haloalkyl, C$_1$-C$_6$ haloalkoxy, —COOH, —CHO, —CONH$_2$, C$_2$-C$_6$ alkanoyl, mono-C$_1$-C$_2$ alkylamino, or di-C$_1$-C$_2$ alkylamino;

Y is S, S(O), or S(O)$_2$;

n is 1, 2, or 3;

Z is O, S, or 2H;

m is 0 or 1;

A is one of A1 to A4

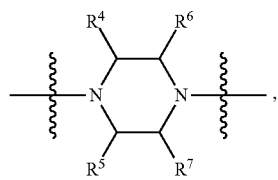

A1

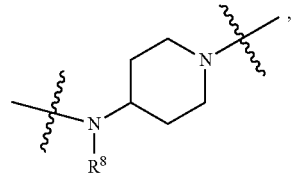

A2

-continued

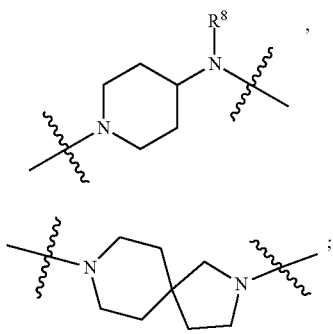

R$^4$, R$^5$, R$^6$, and R$^7$ each independently are hydrogen, C$_1$-C$_6$ alkyl, C$_2$-C$_6$ alkenyl, C$_1$-C$_6$ haloalkyl, or C$_2$-C$_6$ alkanoyl, with the proviso that at least one of R$^4$, R$^5$, R$^6$, and R$^7$ is other than hydrogen;

R$^8$ is hydrogen, C$_1$-C$_6$ alkyl, C$_1$-C$_6$ haloalkyl, or C$_2$-C$_6$ alkanoyl; and R$^3$ is hydrogen, C$_1$-C$_8$ alkyl, C$_1$-C$_6$ haloalkyl, C$_2$-C$_6$ alkenyl, C$_3$-C$_7$ cycloalkyl, C$_2$-C$_6$ alkanoyl, aryl-(C=O)—, monocyclic heteroaryl-(C=O)—, bicyclic heteroaryl-(C=O)—, (C$_3$-C$_7$ cycloalkyl)C$_0$-C$_6$ alkyl, (C$_3$-C$_7$ cycloalkenyl)C$_0$-C$_6$alkyl, (heterocycloalkyl)C$_0$-C$_6$ alkyl, (heterocycloalkenyl)C$_0$-C$_6$ alkyl, (aryl)C$_0$-C$_6$ alkyl, (monocyclic heteroaryl)C$_0$-C$_6$ alkyl, (bicyclic heteroaryl)C$_0$-C$_6$ alkyl, or (C$_2$-C$_6$ alkanoyl)C$_0$-C$_6$ alkyl, wherein each alkyl independently can optionally be substituted with 1 or 2 substituents and each aryl and heteroaryl independently can optionally be substituted with 1, 2, or 3 substituents, wherein each substituent is independently selected from halogen, hydroxyl, amino, nitro, cyano, C$_1$-C$_6$ alkyl, C$_2$-C$_6$ alkenyl, C$_1$-C$_6$ alkoxy, C$_1$-C$_6$ haloalkyl, C$_1$-C$_6$ haloalkoxy, —COOH, —CHO, —CONH$_2$, C$_2$-C$_6$ alkanoyl, mono-C$_1$-C$_2$ alkylamino, di-C$_1$-C$_2$ alkylamino, or phenyl, wherein the phenyl can optionally be substituted with halogen, hydroxyl, amino, nitro, cyano, C$_1$-C$_6$ alkyl, C$_2$-C$_6$ alkenyl, C$_1$-C$_6$ alkoxy, C$_1$-C$_6$ haloalkyl, C$_1$-C$_6$ haloalkoxy, —COOH, —CHO, —CONH$_2$, C$_2$-C$_6$ alkanoyl, mono-C$_1$-C$_2$ alkylamino, or di-C$_1$-C$_2$ alkylamino;

with the proviso that when A is A2, R$^1$ and R$^2$ are each phenyl, Y is S, n is 1, m is 1, Z is O, and R$^8$ is methyl, then either i) R$^3$ is other than hydrogen or unsubstituted C$_1$-C$_8$ alkyl, or ii) both R$^1$ and R$^2$ have at least one substituent.

In an embodiment, a compound of Formula I where Y is S or S(O). When Y is S(O), i.e. a sulfoxide, the sulfoxide fragment can be racemic, have an (R)-configuration, or an (S)-configuration.

In an embodiment, a compound of Formula I wherein R$^1$ and R$^2$ independently is an optionally substituted phenyl; more specifically substituted phenyl with 1, 2, or 3 substituents, specifically 1 or 2, and more specifically 1 substituent; each substituent independently selected from halogen, hydroxyl, amino, nitro, cyano, C$_1$-C$_6$ alkyl, C$_2$-C$_6$ alkenyl, C$_1$-C$_6$ alkoxy, C$_1$-C$_6$ haloalkyl, C$_1$-C$_6$ haloalkoxy, —COOH, —CHO, —CONH$_2$, C$_2$-C$_6$ alkanoyl, mono-C$_1$-C$_2$ alkylamino, or di-C$_1$-C$_2$ alkylamino, specifically the substituent is halogen or C$_1$-C$_6$ haloalkyl, and more specifically fluoro.

In an embodiment, a compound of Formula I wherein m is 1 and Z is O or 2H. The substituent "2H" means two hydrogens, each singly bonded to the adjacent carbon atom, to result in a methylene —CH$_2$— group.

In an embodiment, a compound of Formula I wherein n is 2 and m is 0.

In another embodiment, a compound of Formula I wherein R$^3$ is C$_1$-C$_5$ alkyl, C$_1$-C$_6$ haloalkyl, aryl-(C=O)—, monocyclic heteroaryl-(C=O)—, bicyclic heteroaryl-(C=O)—, (C$_3$-C$_7$ cycloalkyl)C$_0$-C$_6$alkyl, (heterocycloalkyl)C$_0$-C$_6$ alkyl, (heterocycloalkenyl)C$_0$-C$_6$ alkyl, (aryl)C$_0$-C$_6$ alkyl, (monocyclic heteroaryl)C$_0$-C$_6$ alkyl, (bicyclic heteroaryl)C$_0$-C$_6$ alkyl, or (C$_2$-C$_6$ alkanoyl)C$_0$-C$_6$ alkyl, wherein each alkyl independently can optionally be substituted with 1 or 2 substituents, specifically substituted with 1 hydroxyl, and each aryl and heteroaryl independently can optionally be substituted with 1, 2, or 3 substituents. In an embodiment, the compound of Formula I wherein R$^3$ is a group substituted with hydroxyl, the compound is isolated predominantly or entirely as a single enantiomer or diastereomer where the hydroxyl group is in the R or S configuration.

In an embodiment, a compound of Formula I wherein A is

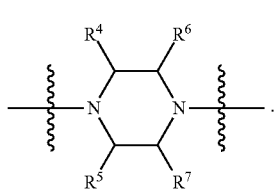

Within this embodiment, R$^4$, R$^5$, R$^6$, and R$^7$ each independently is hydrogen, C$_1$-C$_3$ alkyl, C$_2$-C$_3$ alkenyl, C$_1$-C$_3$ haloalkyl, or C$_2$-C$_3$ alkanoyl, with the proviso that at least one of R$^4$, R$^5$, R$^6$, and R$^7$ is other than hydrogen. In a specific embodiment, R$^4$, R$^5$, R$^6$, and R$^7$ each independently is hydrogen or C$_1$-C$_3$ alkyl (e.g., methyl), with the proviso that at least one of R$^4$, R$^5$, R$^6$, and R$^7$ is other than hydrogen. In an embodiment, R$^6$ and R$^7$ are other than hydrogen, and R$^6$ and R$^7$ can be identical or different. In another embodiment, R$^4$ and R$^5$ are other than hydrogen, and R$^4$ and R$^5$ can be identical or different. In yet another embodiment, R$^4$ and R$^7$ are other than hydrogen, and R$^4$ and R$^7$ can be identical or different. In still yet another embodiment, R$^5$ and R$^6$ are other than hydrogen, and R$^5$ and R$^6$ can be identical or different. In a specific embodiment, at least one of, specifically at least two of R$^4$, R$^5$, R$^6$, and R$^7$ is/are methyl. Depending upon the groups for R$^4$, R$^5$, R$^6$, and R$^7$, A1 may contain one or more stereogenic centers and can exist as single enantiomers, single diastereomers, racemates, or mixtures of diastereomers.

In another embodiment, a compound of Formula I wherein A is

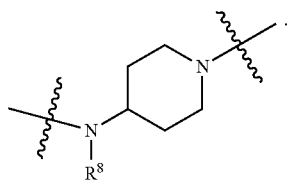

Within this embodiment, R$^8$ can be hydrogen, C$_1$-C$_3$ alkyl, C$_1$-C$_3$ haloalkyl, or C$_2$-C$_3$ alkanoyl; and more specifically R$^8$ can be hydrogen.

In another embodiment, a compound of Formula I wherein A is

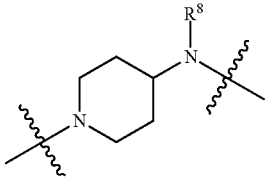

A3

Within this embodiment, $R^8$ can be hydrogen, $C_1$-$C_3$ alkyl, $C_1$-$C_3$ haloalkyl, or $C_2$-$C_3$ alkanoyl; and more specifically $R^8$ can be hydrogen.

In another embodiment, a compound of Formula I wherein A is

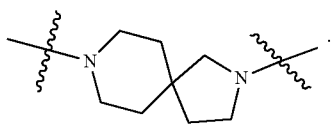

A4

In addition to compounds of Formula I as described above, this disclosure also includes compounds of Formulae IA1, IA2, IA3, and IA4, which are subgeneric compounds of Formula I that carry any combination of the variable definitions set forth below that result in a stable compound.

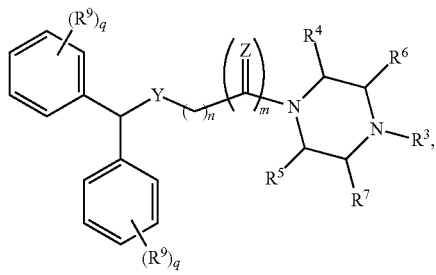

IA1

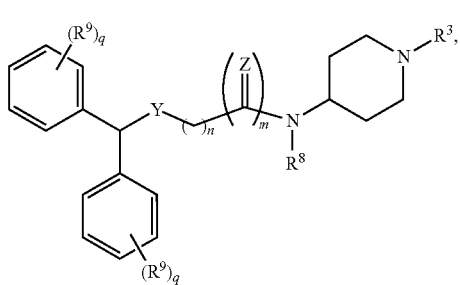

IA2

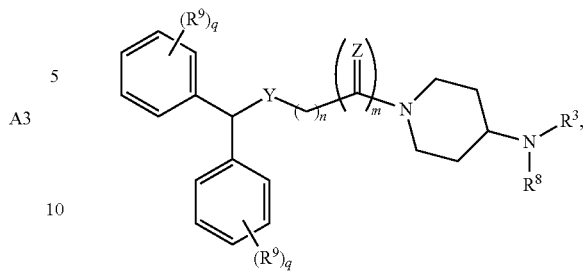

IA3

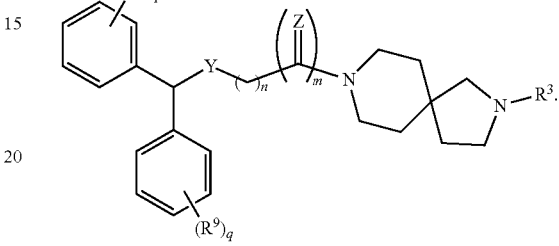

IA4

The definitions of Y, n, Z, m, $R^3$, $R^4$, $R^5$, $R^6$, R, and R, are the same as defined above for Formula I. Each instance of q is 0, 1, 2, or 3; and each instance of $R^9$ is halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, or di-$C_1$-$C_2$ alkylamino. In an embodiment, a compound of Formula IA1, IA2, IA3, or IA4 wherein q is 1 or 2 and $R^9$ is halogen, hydroxyl, amino, nitro, cyano, $C_1$-$C_3$ alkyl, $C_2$-$C_3$ alkenyl, $C_1$-$C_3$ alkoxy, $C_1$-$C_3$ haloalkyl, $C_1$-$C_3$ haloalkoxy, —COOH, —CHO, —CONH$_2$, $C_2$-$C_3$ alkanoyl, mono-$C_1$-$C_2$ alkylamino, or di-$C_1$-$C_2$ alkylamino; more specifically halogen, e.g. fluoro. Unless indicated, each $R^9$ independently can be located at the ortho, meta, or para positions of the ring, specifically the meta or para positions.

Also included in this disclosure are compounds of Formula I, as set out in Table 1 and Table 2 in its free form (e.g. free base form), or as a pharmaceutically acceptable salt thereof.

In addition to compounds of Formula I as described above, this disclosure also includes compounds of Formula I wherein a sulfoxide fragment (i.e., where Y is S(O)) has an (R)- or (S)-configuration.

The compounds are described using standard nomenclature. Unless defined otherwise, all technical and scientific terms used herein have the same meaning as is commonly understood by one of skill in the art to which this disclosure belongs. Unless clearly contraindicated by the context each compound name includes the free acid or free base form of the compound as well hydrates of the compound and all pharmaceutically acceptable salts of the compound.

The term "Formula I", as used herein, encompasses all compounds that satisfy Formula I, including any enantiomers, racemates and stereoisomers as well as all pharmaceutically acceptable salts, solvates, and hydrates of such compounds. The phrase "a compound of Formula I" includes all subgeneric groups of Formula I including Formula IA1, IA2, IA3, or IA4, and so forth, as well as all forms of such compounds, including salts and hydrates, unless clearly contraindicated by the context in which this phrase is used.

Formula I includes all subformulae thereof. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In these situations, single enantiomers, i.e., optically active forms, can be obtained by asymmetric synthesis, synthesis from optically pure precursors, or by resolution of the racemates or racemic intermediates. Resolution of the racemates can also be accomplished, for example, by conventional methods such as crystallization in the presence of a resolving agent, or chromatography, using, for example, a chiral HPLC column.

Where a compound exists in various tautomeric forms, the compound is not limited to any one of the specific tautomers, but rather includes all tautomeric forms. All isotopes of atoms occurring in the present compounds are contemplated. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $R^1$-$R^9$, Y, Z, etc. Unless otherwise specified, each variable within such a formula is defined independently of other variables. Thus, if a group is said to be substituted, e.g., with 0-2 $R_1$, then the group may be substituted with up to two $R_1$ groups and $R_1$ at each occurrence is selected independently from the definition of $R_1$. Also, combinations of substituents and/or variables are permissible only if such combinations result in a stable compound.

The term "active agent", as used herein, means a compound (including a compound of Formula I), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. All forms are contemplated herein regardless of the methods used to obtain them.

A dash ("-") that is not between two letters or symbols is used to indicate a point of attachment for a substituent. For example, —($CH_2$)$C_3$-$C_8$ cycloalkyl is attached through carbon of the methylene ($CH_2$) group.

"Alkanoyl" is an alkyl group as defined herein, covalently bound to the group it substitutes by a keto (—(C═O)—) bridge. Alkanoyl groups have the indicated number of carbon atoms, with the carbon of the keto group being included in the numbered carbon atoms. For example a $C_2$alkanoyl group is an acetyl group having the formula $CH_3(C═O)$—. A $C_4$alkanoyl group or greater can include a cycloalkyl group (e.g. cyclopropane group) as well as linear or branched groups.

The term "alkyl", as used herein, means a branched or straight chain saturated aliphatic hydrocarbon group having the specified number of carbon atoms, generally from 1 to about 12 carbon atoms. The term $C_1$-$C_6$ alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_6$ alkyl, $C_1$-$C_4$ alkyl, and $C_1$-$C_2$ alkyl. When $C_0$-$C_n$ alkyl is used herein in conjunction with another group, for example, (cycloalkyl)$C_0$-$C_4$ alkyl, the indicated group, in this case cycloalkyl, is either directly bound by a single covalent bond ($C_0$), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

The term "cycloalkyl", as used herein, indicates a saturated hydrocarbon ring group, having only carbon ring atoms and having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

The term "heterocycloalkyl", as used herein, indicates a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized.

The term "alkenyl", as used herein, means straight and branched hydrocarbon chains comprising one or more unsaturated carbon-carbon bonds, which may occur in any stable point along the chain. Alkenyl groups described herein typically have from 2 to about 12 carbon atoms. Exemplary alkenyl groups are lower alkenyl groups, those alkenyl groups having from 2 to about 8 carbon atoms, e.g. $C_2$—C, $C_2$-$C_6$, and $C_2$-$C_4$ alkenyl groups. Examples of alkenyl groups include ethenyl, propenyl, and butenyl groups.

The term "cycloalkenyl", as used herein, means a saturated hydrocarbon ring group, comprising one or more unsaturated carbon-carbon bonds, which may occur in any stable point of the ring, and having the specified number of carbon atoms. Monocyclic cycloalkenyl groups typically have from 3 to about 8 carbon ring atoms or from 3 to 7 (3, 4, 5, 6, or 7) carbon ring atoms. Cycloalkenyl substituents may be pendant from a substituted nitrogen or carbon atom, or a substituted carbon atom that may have two substituents may have a cycloalkenyl group, which is attached as a spiro group. Examples of cycloalkenyl groups include cyclopropenyl, cyclobutenyl, cyclopentenyl, or cyclohexenyl as well as bridged or caged saturated ring groups such as norbornene.

The term "heterocycloalkenyl", as used herein, refers to a 3- to 10-membered, including 4- to 8-membered, non-aromatic ring structure having one or more double bonds, and wherein one or more of the ring atoms is a heteroatom, e.g., N, O, or S.

The terms "(cycloalkyl)$C_0$-$C_n$ alkyl", as used herein, means a substituent in which the cycloalkyl and alkyl are as defined herein, and the point of attachment of the (cycloalkyl)alkyl group to the molecule it substitutes is either a single covalent bond, ($C_0$alkyl) or on the alkyl group. (Cycloalkyl)alkyl encompasses, but is not limited to, cyclopropylmethyl, cyclobutylmethyl, and cyclohexylmethyl.

The term "(heterocycloalkyl)$C_0$-$C_n$ alkyl", as used herein, means a substituent in which the heterocycloalkyl and alkyl are as defined herein, and the point of attachment of the (heterocycloalkyl)alkyl group to the molecule it substitutes is either a single covalent bond, ($C_0$alkyl) or on the alkyl group. (Heterocycloalkyl)alkyl encompasses, but is not limited to, morpholinylmethyl, piperazinylmethyl, piperidinylmethyl, and pyrrolidinylmethyl groups.

The term "(heterocycloalkenyl)$C_0$-$C_6$ alkyl", as used herein, means a substituent in which the heterocycloalkenyl and alkyl are as defined herein, and the point of attachment of the (heterocycloalkenyl)alkyl group to the molecule it substitutes is either a single covalent bond, ($C_0$alkyl) or on the alkyl group.

The term "aryl", as used herein, means aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Bicyclic aryl groups may be further substituted with carbon or non-carbon atoms or groups. Bicyclic aryl groups may contain two fused aromatic rings (naphthyl) or an aromatic ring fused to a 5- to 7-membered non-aromatic cyclic group that optionally contains 1 or 2 heteroatoms independently chosen from N, O, and S, for example, a 3,4-methylenedioxy-phenyl group. Aryl groups include, for example, phenyl, naphthyl, including 1-naphthyl and 2-naphthyl, and bi-phenyl.

The term "mono- or bicyclic heteroaryl", as used herein, indicates a stable 5- to 7-membered monocyclic or 7- to 10-membered bicyclic heterocyclic ring which contains at least 1 aromatic ring that contains from 1 to 4, or specifically from 1 to 3, heteroatoms chosen from N, O, and S, with remaining ring atoms being carbon. When the total number of S and O atoms in the heteroaryl group exceeds 1, theses heteroatoms are not adjacent to one another. Specifically, the total number of S and O atoms in the heteroaryl group is not more than 2, more specifically the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. In certain embodiments 5- to 6-membered heteroaryl groups are used. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Haloalkyl" includes both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined herein attached through an oxygen bridge (oxygen of an alcohol radical).

"Halo" or "halogen" is any of fluoro, chloro, bromo, and iodo.

"Mono- and/or di-alkylamino" is a secondary or tertiary alkyl amino group, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

The term "substituted", as used herein, means that any one or more hydrogens on the designated atom or group is replaced with a selection from the indicated group, provided that the designated atom's normal valence is not exceeded. When the substituent is oxo (i.e., $=O$) then 2 hydrogens on the atom are replaced. When an oxo group substitutes aromatic moieties, the corresponding partially unsaturated ring replaces the aromatic ring. For example, a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Unless otherwise specified substituents are named into the core structure. For example, it is to be understood that when (cycloalkyl)alkyl is listed as a possible substituent the point of attachment of this substituent to the core structure is in the alkyl portion, or when arylalkyl is listed as a possible substituent the point attachment to the core structure is the alkyl portion.

Suitable groups that may be present on a "substituted" or "optionally substituted" position include, but are not limited to, halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylsulfenyl groups including those having one or more sulfenyl linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

The term "dosage form", as used herein, means a unit of administration of an active agent. Examples of dosage forms include tablets, capsules, injections, suspensions, liquids, emulsions, creams, ointments, suppositories, inhalable forms, transdermal forms, and the like. Exemplary dosage form is a solid oral dosage form.

The term "pharmaceutical compositions", as used herein, are compositions comprising at least one active agent, such as a compound or salt of Formula I, and at least one other substance, such as a carrier. Pharmaceutical compositions meet the U.S. FDA's GMP (good manufacturing practice) standards for human or non-human drugs. The pharmaceutical compositions can be formulated into a dosage form.

The term "pharmaceutically acceptable salt", as used herein, includes derivatives of the disclosed compounds in which the parent compound is modified by making inorganic and organic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier", as used herein, applied to pharmaceutical compositions refers to a diluent, excipient, or vehicle with which an active compound is provided.

The term "patient", as used herein, is a human or non-human animal in need of medical treatment. Medical treatment can include treatment of an existing condition, such as a disease or disorder, prophylactic or preventative treatment, or diagnostic treatment. In some embodiments the patient is a human patient.

The term "providing", as used herein, means giving, administering, selling, distributing, transferring (for profit or not), manufacturing, compounding, or dispensing.

The term "providing a compound of Formula I with at least one additional therapeutic agent", as used herein, means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

The term "treatment", as used herein, includes providing a compound of Formula I, either as the only active agent or together with at least one additional active agent sufficient to: (a) prevent a disease or a symptom of a disease from occurring in a patient who may be predisposed to the disease but has not yet been diagnosed as having it; (b) inhibiting the disease, i.e. arresting its development; and (c) relieving the disease, i.e., causing regression of the disease. "Treating" and "treatment" also means providing a therapeutically effective amount of a compound of Formula I, as the only active agent or together with at least one additional active agent to a patient suffering from substance use disorders, attention deficit hyperactive disorder (ADHD), depressive disorders, sleep disorders or cognitive impairment or in order to elicit a wake-promoting, cognition-enhancing or mood-enhancing effect(s) in a patient.

The term "therapeutically effective amount" of a pharmaceutical composition, as used herein, means an amount effective, when administered to a patient, to provide a therapeutic benefit such as an amelioration of symptoms, e.g., to treat a patient suffering from substance use disorders, attention deficit hyperactive disorder (ADHD), depressive disorders, sleep disorders or cognitive impairment or in order to elicit a wake-promoting, cognition-enhancing or mood-enhancing effect in a patient.

The compounds can be administered as the neat chemical, or administered as a pharmaceutical composition. Accordingly, an embodiment provides pharmaceutical compositions comprising a compound or pharmaceutically acceptable salt of Formula I, IA1, IA2, IA3, or IA4, together with a pharmaceutically acceptable carrier. The pharmaceutical composition may contain a compound or salt of Formula I, IA1, IA2, IA3, or IA4 as the only active agent, or may contain one or more additional active agents.

The compounds may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the compound of Formula I.

The pharmaceutical compositions can be formulated for oral administration. These compositions contain between 0.1 and 99 weight percent ("wt. %") of a compound of Formula I, IA1, IA2, IA3, or IA4 and usually at least about 5 wt. %. Some embodiments contain from about 25 wt. % to about 50 wt. % or from about 5 wt. % to about 75 wt. % of a compound of Formula I, IA1, IA2, IA3, or IA4.

The pharmaceutical composition can be formulated in a package comprising the pharmaceutical composition of Formula I, IA1, IA2, IA3, or IA4 in a container and further comprising instructions for using the composition in order to elicit a therapeutic effect (e.g. wake-promoting, cognition-enhancing or mood-enhancing effect) in a patient.

The pharmaceutical composition can also be formulated in a package comprising the pharmaceutical composition of Formula I, IA1, IA2, IA3, or IA4 in a container and further comprising instructions for using the composition to treat a patient suffering from, for example, substance use disorders, attention deficit (hyperactivity) disorder, depressive disorders, sleep disorders or cognitive impairment.

In an embodiment, a method of eliciting a wake-promoting, cognition-enhancing or mood-enhancing effect comprises providing an effective amount of a compound or salt of Formula I, IA1, IA2, IA3, or IA4 to a patient in need of such treatment. Alternatively, the compound may be provided in the form of a pharmaceutical composition.

In an embodiment, a method for treating substance use disorders (e.g. cocaine, methamphetamine, opioids, and the like), attention deficit hyperactive disorder, sleep disorders or cognitive impairment including cognitive impairment in psychostimulant abuse, schizophrenia and NeuroAIDS, Alzheimer's disease, depression, nicotine abuse (e.g., for smoking cessation), cancer-associated fatigue, multiple sclerosis-associated fatigue, jet-lag, post-operative grogginess, age-related memory decline, obesity (as an anorectic agent), attention, bipolar disorder, anxiety, sleep disorders, or obsessive-compulsive disorders comprises providing an effective amount of a compound or salt of Formula I, IA, IA2, IA3, or IA4 to a patient in need of such treatment. Alternatively, the compound may be provided in the form of a pharmaceutical composition.

This invention is further illustrated by the following examples that should not be construed as limiting.

EXAMPLES

Examples 1-3 are directed to the synthetic methods for preparing the analogue compounds of Formula I and sub-formula IA1, IA2, IA3, and IA4. Reaction conditions and yields were not optimized.

Example 1. Synthesis of Aminopiperidine and Piperidineamino Analogues

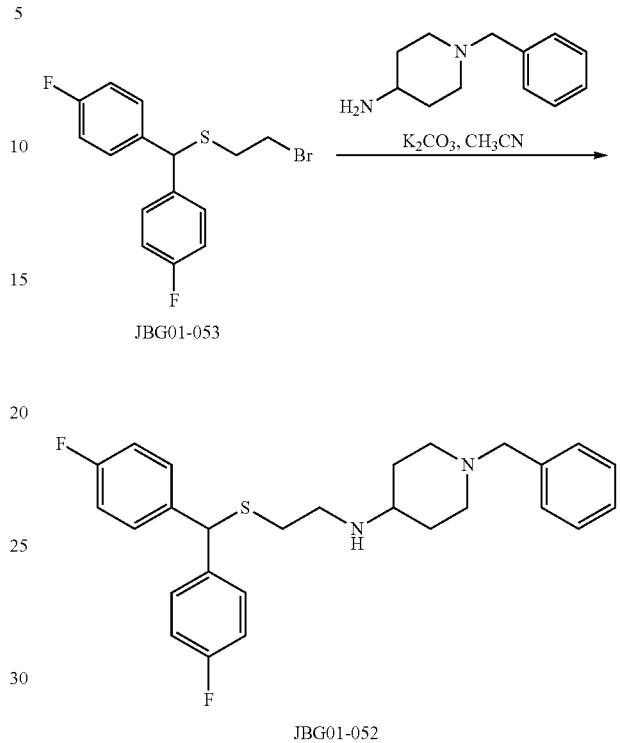

JBG01-053

JBG01-052

Synthesis of JBG01-052 [1-Benzyl-N-(2-((bis(4-fluorophenyl)methyl)thio)ethyl)piperidin-4-amine]

To a 10 mL round bottom flask equipped with a stir bar and a condenser was added (bis(4-fluorophenyl)methyl)(2-bromoethyl)sulfane (200 mg, 0.583 mmol; Cao, J. et al., J. Med. Chem. 2016, 59 (23), 10676-10691) and dry $K_2CO_3$ (644 mg, 4.66 mmol). Anhydrous acetonitrile (2.33 mL) was added via syringe under an argon atmosphere, and the reaction mixture was permitted to stir. Commercially available 1-benzylpiperidin-4-amine (0.143 mL, 0.70 mmol) was added dropwise via syringe and was stirred for 4.5 hours at reflux. The reaction mixture was filtered to remove residual $K_2CO_3$, washed with cold acetonitrile, and the filtrate was concentrated under reduced pressure. The crude oil was purified by flash column chromatography (0-5% MeOH/0-0.125% $NH_4OH$ in $CH_2Cl_2$) to afford JBG01-052 (181 mg, 0.400 mmol, 69% yield) as a yellow oil. The free base was converted to the corresponding HCl salt and recrystallized from hot isopropyl alcohol to give a colorless crystalline solid. $^1H$ NMR (400 MHz, $CDCl_3$) δ 7.41-7.22 (m, 9H), 7.00 (m, 4H), 5.17 (s, 1H), 3.51 (s, 2H), 2.85 (m, 2H), 2.77 (t, J=6.6 Hz, 2H), 2.56 (t, J=6.5 Hz, 2H), 2.42 (m, 1H), 2.03 (m, 2H), 1.98-1.86 (m, 1H), 1.86-1.77 (m, 2H), 1.47-1.34 (m, 2H); $^{13}C$ NMR (100 MHz, $CDCl_3$) δ 163.11, 160.66, 138.35, 137.01, 136.97, 129.86, 129.83, 129.78, 129.75, 129.12, 128.20, 127.00, 115.62, 115.40, 63.00, 54.51, 52.56, 52.26, 45.11, 32.90, 32.57; Anal. ($C_{27}H_{30}F_2N_2S\cdot2HCl\cdot0.5H_2O$) C, H, N. The c Log P of JBG01-052 is 5.80.

General Method for Reductive Amination:

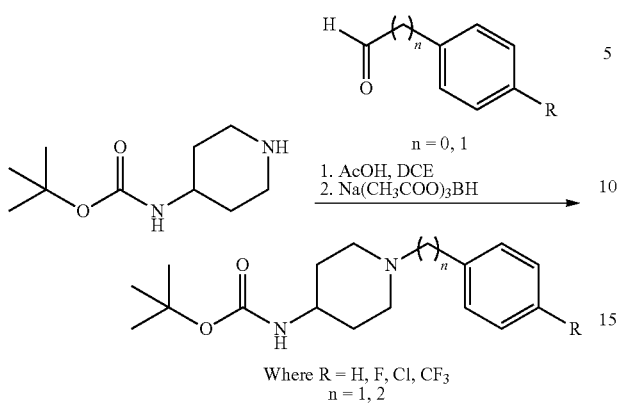

Where R = H, F, Cl, CF$_3$
n = 1, 2

To an appropriately size round bottom flask equipped with a stir bar was added the appropriate commercially available amine (1 eq) and dissolved in dichloroethane (0.03 M), and the reaction was permitted to stir until dissolved. Acetic acid (catalytic) was added dropwise via syringe under an argon atmosphere. The appropriate aldehyde (1 eq) was added dropwise via syringe and was permitted to stir for 15 minutes. Sodium triacetoxyborohydride (1.5 eq) was added in one portion, and the reaction was stirred overnight at room temperature. Solvent was removed under reduced pressure, and the residue was resuspended in CH$_2$Cl$_2$. The combined organics were washed with NaHCO$_3$ then brine, and dried with MgSO$_4$. The organics were concentrated in vacuo and purified via flash column chromatography to afford the desired N-alkyl product.

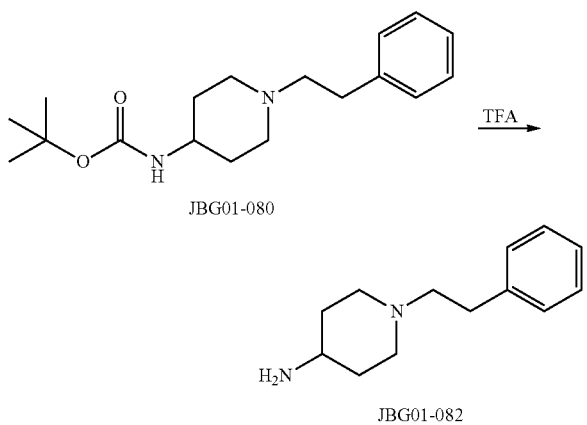

Synthesis of JBG01-082
[1-Phenethylpiperidin-4-amine]

To a 15 mL round bottom flask equipped with a stir bar was added the JBG01-080 (175 mg, 0.575 mmol; Nguyen, T. et al., Eur. J. Med. Chem. 2011, 46 (7), 2917-2929) and trifluoroacetic acid (TFA, 1.2 mL). The reaction was permitted to stir for 1 hr at room temperature under an argon atmosphere. Solvent was removed under reduced pressure, and the residue was resuspended in CH$_2$Cl$_2$ (30 mL). The organics were washed with NaHCO$_3$ (3×10 mL, pH=8) and rinsed with brine (3×10 mL). The combined aqueous layers were concentrated and extracted with CH$_2$Cl$_2$. The combined organics were dried with MgSO$_4$ and concentrated in vacuo to yield JBG01-082 (165 mg, quantitative yield) as a yellow amorphous solid, which was immediately used in the next step.

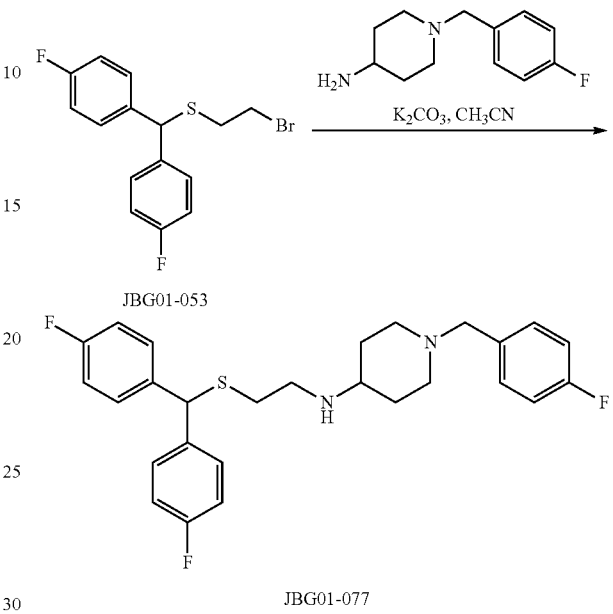

Synthesis of JBG01-077 [N-(2-((Bis(4-fluorophenyl)methyl)thio)ethyl)-1-(4-fluorobenzyl)piperidin-4-amine]

To a 15 mL round bottom flask equipped with a stir bar and a condenser was added (bis(4-fluorophenyl)methyl)(2-bromoethyl)sulfane (JBG01-053, 92 mg, 0.27 mmol) and K$_2$CO$_3$ (297 mg, 2.14 mmol). Anhydrous acetonitrile (0.5 mL) was added via syringe under an argon atmosphere, and the reaction mixture was permitted to stir. A solution of 1-(4-fluorobenzyl)piperidin-4-amine (67 mg, 0.322 mmol; Shum, P. et al., Nucleosides, Nucleotides and Nucleic Acids 2001, 20 (4-7), 1067-1078) in anhydrous acetonitrile (0.6 mL) was added dropwise via syringe, and the reaction was stirred for 4.5 hours at reflux. The reaction mixture was cooled to 0° C. and filtered to remove residual K$_2$CO$_3$, washed with cold acetonitrile, and the filtrate was concentrated under reduced pressure. The crude oil was purified by flash column chromatography (0-5% MeOH/0-0.125% NH$_4$OH in CH$_2$Cl$_2$) to afford JBG01-077 (53 mg, 0.11 mmol, 42% yield). The free base was converted to the corresponding HCl salt and was recrystallized from hot isopropyl alcohol to give a colorless crystalline solid. $^1$H NMR (400 MHz, CDCl$_3$) δ 7.36 (m, 4H), 7.26 (m, 2H), 6.99 (m, 6H), 5.15 (s, 1H), 3.44 (s, 2H), 2.78 (m, 4H), 2.54 (m, 2H), 2.39 (m, 1H), 1.98 (m, 2H), 1.78 (m, 2H), 1.48-1.29 (m, 3H); $^{13}$C NMR (100 MHz, CDCl$_3$) δ 163.12, 163.10, 160.69, 160.65, 136.98, 136.95, 134.28, 134.25, 130.47, 130.39, 129.82, 129.79, 129.74, 129.71, 115.65, 115.59, 115.44, 115.38, 115.02, 114.81, 62.18, 54.53, 52.55, 52.24, 45.12, 33.01, 32.72; FT-IR (ATR, υ, cm$^{-1}$) 2932, 2797, 1602, 1506, 1466, 1222, 1156, 1092, 1015, 827; Anal. (C$_{27}$H$_{29}$F$_3$N$_2$S.2HCl.0.5H$_2$O) C, H, N. The c Log P of JBG01-077 is 5.94.

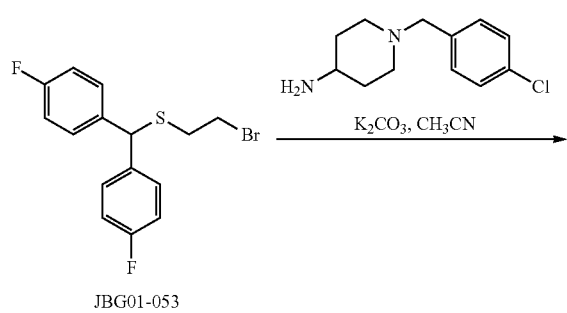
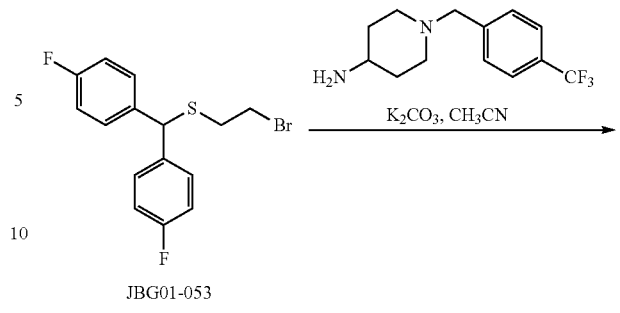

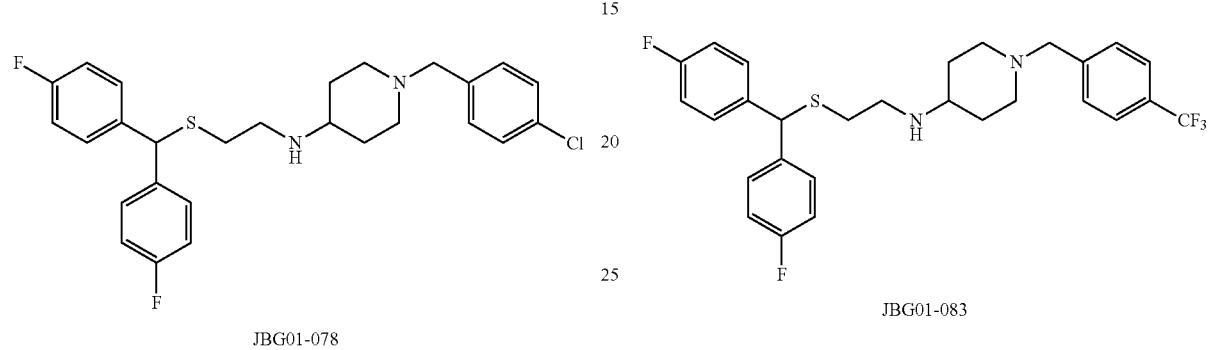

Synthesis of JBG01-078 [N-(2-((Bis(4-fluorophenyl)methyl)thio)ethyl)-1-(4 chlorobenzyl)piperidin-4-amine]

To a 15 mL round bottom flask equipped with a stir bar and a condenser was added (bis(4-fluorophenyl)methyl)(2-bromoethyl)sulfane (98 mg, 0.29 mmol) and $K_2CO_3$ (317 mg, 2.29 mmol). Anhydrous acetonitrile (0.6 mL) was added via syringe under an argon atmosphere, and the reaction mixture was permitted to stir. A solution of 1-(4-chlorobenzyl)piperidin-4-amine (77 mg, 0.34 mmol) in anhydrous acetonitrile (0.6 mL) was added dropwise via syringe, and the reaction was stirred for 4.5 hours at reflux. The reaction mixture was cooled to 0° C. and filtered to remove residual $K_2CO_3$, washed with cold acetonitrile, and the filtrate was concentrated under reduced pressure. The crude oil was purified by flash column chromatography (0-5% MeOH/0-0.125% $NH_4OH$ in $CH_2Cl_2$) to afford JBG01-078 (75 mg, 0.15 mmol, 54% yield). The free base was converted to the corresponding HCl salt and was recrystallized from hot isopropyl alcohol to give a colorless crystalline solid. $^1H$ NMR (400 MHz, $CDCl_3$) δ 7.36 (m, 4H), 7.24 (m, 4H), 7.00 (m, 4H), 5.15 (s, 1H), 3.44 (s, 2H), 2.77 (m, 4H), 2.54 (t, J=6.5 Hz, 2H), 2.39 (m, 1H), 1.98 (m, 2H), 1.78 (m, 2H), 1.54-1.29 (m, 3H); $^{13}C$ NMR (101 MHz, $CDCl_3$) δ 163.10, 160.65, 137.19, 136.98, 136.95, 132.56, 130.26, 129.80, 129.72, 128.29, 115.60, 115.38, 62.21, 54.49, 52.56, 52.28, 45.13, 33.00, 32.70; FT-IR (ATR, υ, $cm^{-1}$) 2934, 2804, 1725, 1602, 1505, 1366, 1225, 1156, 1096, 835; Anal. ($C_{27}H_{29}CF_2N_2S\cdot2HCl\cdot0.5H_2O$) C, H, N. The c Log P of JBG01-078 is

Synthesis of JBG01-083 [N-(2-((Bis(4-fluorophenyl)methyl)thio)ethyl)-1-(4-(trifluoromethyl)benzyl)piperidin-4-amine]

To a 15 mL round bottom flask equipped with a stir bar and a condenser was added (bis(4-fluorophenyl)methyl)(2-bromoethyl)sulfane (155 mg, 0.452 mmol) and $K_2CO_3$ (500 mg, 3.6 mmol). Anhydrous acetonitrile (0.9 mL) was added via syringe under an argon atmosphere, and the reaction mixture was permitted to stir. A solution of 1-(4-(trifluoromethyl)benzyl)piperidin-4-amine (140 mg, 0.542 mmol) in anhydrous acetonitrile (0.9 mL) was added dropwise via syringe, and the reaction was stirred for 3 hours at reflux. The reaction mixture was cooled to 0° C. and filtered to remove residual $K_2CO_3$, washed with cold acetonitrile, and the filtrate was concentrated under reduced pressure. The crude oil was purified by flash column chromatography (0-5% MeOH/0-0.125% $NH_4OH$ in $CH_2Cl_2$) to afford JBG01-083 (73 mg, 0.14 mmol, 31% yield). The free base was converted to the corresponding HCl salt and was recrystallized from hot isopropyl alcohol to give a colorless crystalline solid. $^1H$ NMR (400 MHz, $CDCl_3$) δ 7.56 (m, 2H), 7.43 (m, 2H), 7.36 (m, 4H), 6.99 (m, 4H), 5.15 (s, 1H), 3.52 (s, 2H), 2.78 (m, 4H), 2.55 (t, J=6.5 Hz, 2H), 2.40 (m, 1H), 2.02 (m, 2H), 1.79 (m, 2H), 1.61 (s, 1H), 1.46-1.31 (m, 2H); $^{13}C$ NMR (100 MHz, $CDCl_3$) δ 163.11, 160.66, 142.98, 136.96, 136.93, 129.78, 129.70, 129.03, 125.15, 125.11, 125.08, 125.04, 115.60, 115.39, 62.42, 54.45, 52.57, 52.38, 45.10, 32.97, 32.67; FT-IR (ATR, υ, $cm^{-1}$) 2935, 2800, 1726, 1602, 1505, 1467, 1418, 1325, 1225, 1157, 824; Anal. ($C_{28}H_{29}F_5N_2S\cdot2HCl\cdot0.5H_2O$) C, H, N. The c Log P of JBG01-083 is 6.68.

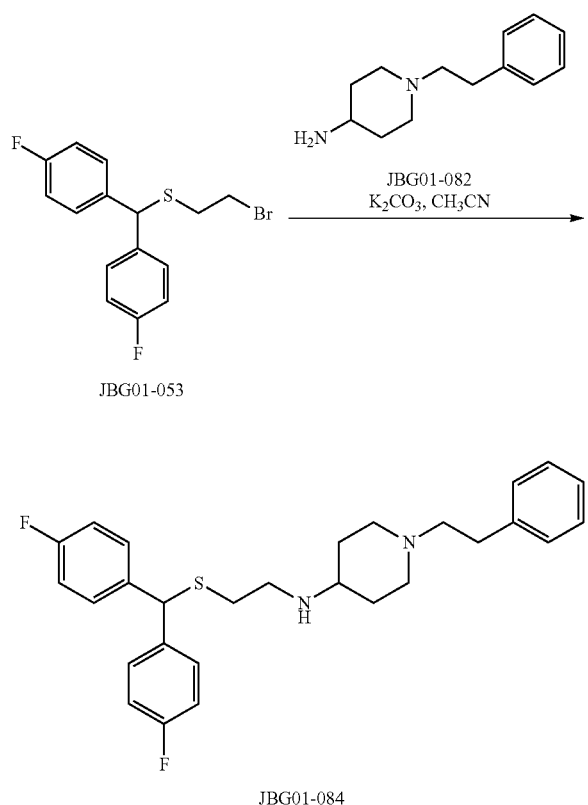

JBG01-053

JBG01-084

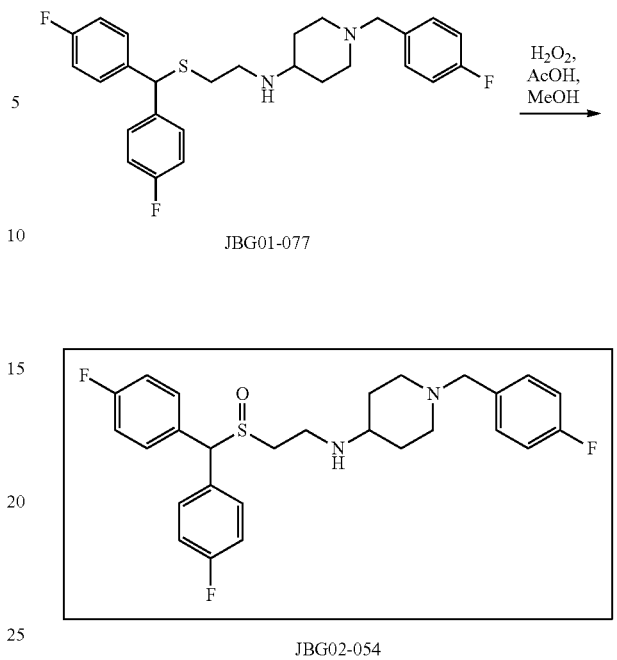

JBG01-077

JBG02-054

Synthesis of JBG01-084 [N-(2-((Bis(4-fluorophenyl)methyl)thio)ethyl)-1-phenethylpiperidin-4-amine]

To a 25 mL round bottom flask equipped with a stir bar and a condenser was added (bis(4-fluorophenyl)methyl)(2-bromoethyl)sulfane (165 mg, 0.481 mmol) and $K_2CO_3$ (532 mg, 3.85 mmol). Anhydrous acetonitrile (1.0 mL) was added via syringe under an argon atmosphere, and the reaction mixture was permitted to stir. A solution of JBG01-082 (118 mg, 0.578 mmol) in anhydrous acetonitrile (0.9 mL) was added dropwise via syringe, and the reaction was stirred for 3 hours at 70° C. The reaction mixture was cooled to 0° C. and filtered to remove residual $K_2CO_3$, washed with cold acetonitrile, and the filtrate was concentrated under reduced pressure. The crude oil was purified by flash column chromatography (0-5% MeOH/0-0.125% $NH_4OH$ in $CH_2Cl_2$) to afford JBG01-084 (42 mg, 0.09 mmol, 19% yield). The free base was converted to the corresponding HCl salt and was recrystallized from hot isopropyl alcohol to give a colorless crystalline solid. $^1H$ NMR (400 MHz, $CDCl_3$) δ 7.36 (m, 4H), 7.27 (m, 2H), 7.20 (d, J=7.3 Hz, 3H), 7.00 (m, 4H), 5.16 (s, 1H), 2.96 (m, 2H), 2.86-2.72 (m, 4H), 2.63-2.51 (m, 4H), 2.42 (m, 1H), 2.07 (m, 2H), 1.93-1.74 (m, 3H), 1.48-1.33 (m, 2H); $^{13}C$ NMR (100 MHz, $CDCl_3$) δ 163.11, 160.66, 140.36, 136.97, 136.94, 129.80, 129.75, 129.72, 128.68, 128.37, 126.01, 115.61, 115.39, 60.54, 54.42, 52.56, 52.37, 45.10, 33.77, 32.98, 32.63; FT-IR (ATR, υ, $cm^{-1}$) 2930, 1737, 1602, 1505, 1454, 1225, 1156, 1115, 835; Anal. ($C_{28}H_{32}F_2N_2S \cdot 2HCl \cdot 0.25H_2O$) C, H, N. The c Log P of JBG01-084 is 5.94.

Synthesis of JBG02-054 [N-(2-((Bis(4-fluorophenyl)methyl)sulfinyl)ethyl)-1-(4-fluorobenzyl)piperidin-4-amine]

To a 50 mL round bottom flask equipped with a stir bar and a condenser was added JBG01-077 (189 mg, 0.402 mmol) and methanol (1.5 mL), and the reaction was permitted to stir until dissolved. Acetic acid (0.5 mL) was added dropwise via syringe under an argon atmosphere and was stirred for 5 minutes. $H_2O_2$ (30% in $H_2O$, 0.035 mL, 0.40 mmol) was added dropwise via syringe, and the reaction was stirred overnight at 40° C. The reaction was quenched with $H_2O$ (5 mL), and solvent was removed in vacuo. The aqueous layer was made basic (pH=8) by the addition of saturated $NaHCO_3$ (25 mL), and the reaction was extracted with $CH_2Cl_2$ (4×50 mL). Combined organics were dried with $MgSO_4$ and the crude oil was purified by flash column chromatography (0-5% MeOH/0-0.125% $NH_4OH$ in $CH_2C_2$) to afford JBG02-054 (87 mg, 0.179 mmol, 45% yield). The free base was converted to the corresponding HCl salt and recrystallized from hot isopropyl alcohol to give a colorless crystalline solid. $^1H$ NMR (400 MHz, $CDCl_3$) δ 7.41 (m, 4H), 7.25 (m, 2H), 7.08 (m, 4H), 6.97 (t, J=8.6 Hz, 2H), 4.91 (s, 1H), 3.43 (s, 2H), 3.06 (t, J=6.3 Hz, 2H), 2.78 (m, 2H), 2.59 (t, J=6.4 Hz, 2H), 2.42 (m, 1H), 1.98 (t, J=11.4 Hz, 2H), 1.86-1.75 (m, 2H), 1.66 (s, 1H), 1.34 (m, 2H); $^{13}C$ NMR (100 MHz, $CDCl_3$) δ 163.99, 163.75, 163.10, 161.52, 161.27, 160.67, 134.21, 134.18, 131.62, 131.59, 131.05, 130.97, 130.50, 130.47, 130.44, 130.42, 130.36, 130.28, 116.42, 116.20, 115.86, 115.64, 115.01, 114.79, 70.34, 62.16, 54.83, 52.14, 51.55, 40.24, 32.66, 32.50; FT-IR (ATR, υ, $cm^{-1}$) 2936, 2799, 1602, 1505, 1467, 1415, 1221, 1159, 1042, 826; Anal. ($C_{27}H_{29}F_3N_2OS \cdot 2HCl$) C, H, N. The c Log P of JBG02-054 is 4.09.

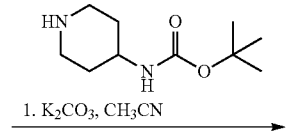 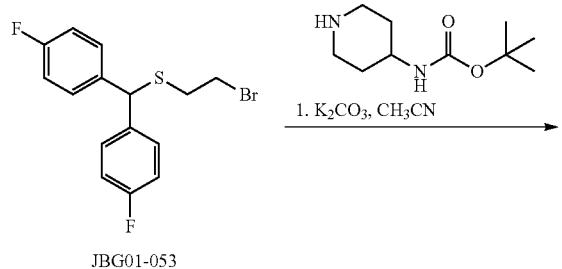 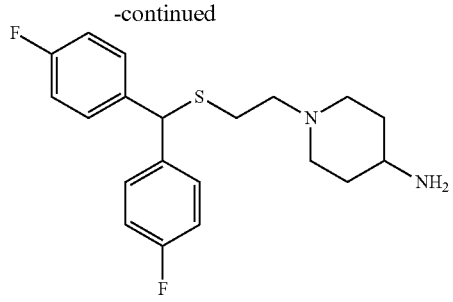

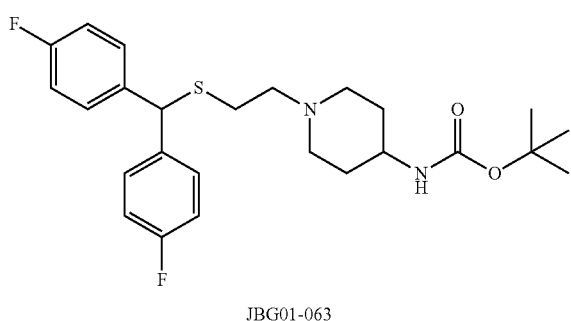

JBG01-063

Synthesis of JBG01-063 [1-(2-((Bis(4-fluorophenyl)methyl)thio)ethyl)piperidin-4-amine]

To a 50 mL round bottom flask equipped with a stir bar and a condenser was added (bis(4-fluorophenyl)methyl)(2-bromoethyl)sulfane (1.50 g, 4.37 mmol) and $K_2CO_3$ (4.83 g, 35.0 mmol). Anhydrous acetonitrile (17.5 mL) was added via syringe under an argon atmosphere, and the reaction mixture was permitted to stir. Commercially available tert-butyl piperidin-4-ylcarbamate (1.05 g, 5.24 mmol) was added dropwise via syringe and was stirred for 4.5 hours at reflux. The reaction mixture was cooled to 0° C. and filtered to remove residual $K_2CO_3$, washed with cold acetonitrile, and the filtrate was concentrated under reduced pressure. The crude oil was purified by flash column chromatography (0-10% MeOH/0-0.125% $NH_4H$ in $CH_2C_2$) to afford JBG01-063 (1.79 g, 3.87 mmol, quantitative yield) as a yellow oil. $^1$H NMR (400 MHz, CDCl$_3$) δ 7.35 (m, 4H), 6.99 (m, 4H), 5.18 (s, 1H), 4.39 (s, 1H), 3.50-3.34 (m, 1H), 2.72 (d, J=11.6 Hz, 2H), 2.56-2.43 (m, 4H), 2.02 (td, J=11.6, 2.6 Hz, 2H), 1.88 (d, J=12.6 Hz, 2H), 1.50-1.31 (m, 11H).

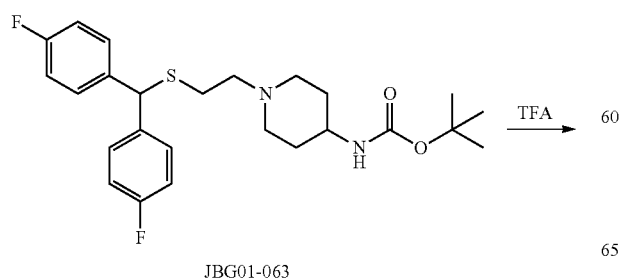

JBG01-063

→ TFA

Synthesis of JBG01-085 [1-(2-((Bis(4 fluorophenyl)methyl)thio)ethyl)piperidin-4-amine]

To a 10 mL round bottom flask equipped with a stir bar and a condenser was added JBG01-063 (0.150 g, 0.324 mmol) and trifluoroacetic acid (2.5 mL). The reaction was permitted to stir for 1 hr at room temperature under an argon atmosphere. Solvent was removed under reduced pressure, and the residue was resuspended in $CH_2Cl_2$ (100 mL). The organics were washed with $NaHCO_3$ (3×50 mL, pH=8) and rinsed with brine (2×50 mL). The combined organics were dried with $MgSO_4$ and concentrated in vacuo to yield JBG01-085 (117 mg, 0.323 mmol, quantitative yield) as a yellow oil. $^1$H NMR (400 MHz, CDCl$_3$) δ 7.36 (m, 4H), 6.99 (m, 4H), 5.20 (s, 1H), 2.77 (d, J=11.8 Hz, 2H), 2.64 (m, 1H), 2.59-2.44 (m, 4H), 1.99 (t, J=11.3 Hz, 2H), 1.78 (d, J=12.8 Hz, 2H), 1.56 (s, 2H), 1.44-1.28 (m, 2H).

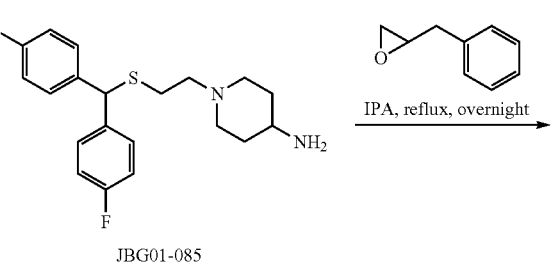

JBG01-085

IPA, reflux, overnight →

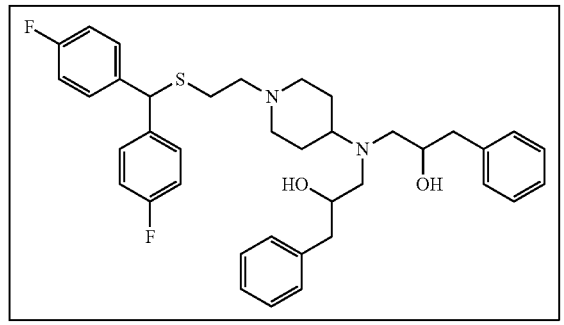

JBG01-056

Synthesis of JBG01-056 [3,3'-((1-(2-((Bis(4-fluorophenyl)methyl)thio)ethyl)piperidin-4-yl)azanediyl)bis(1-phenylpropan-2-ol)]

To a 15 mL oven dried round bottom flask equipped with a stir bar and a condenser was added JBG01-085 (0.130 g, 0.359 mmol) and commercially available 2-benzyloxirane (0.047 mL, 0.36 mmol) under an argon atmosphere. Isopropyl alcohol (3.8 mL) was added via syringe, and the reaction was stirred at reflux overnight, upon which time TLC indicated consumption of starting material. Solvent was removed under reduced pressure, and the crude oil was purified by flash column chromatography (0-5% MeOH/0-0.125% NH$_4$OH in CH$_2$C$_2$) to afford JBG01-056 (105 mg, 0.166 mmol, 46% yield) as a colorless oil. The free base was converted to the corresponding HCl salt to give a colorless solid. $^1$H NMR (400 MHz, CDCl$_3$) δ 7.44-7.15 (m, 14H), 7.01 (m, 4H), 5.17 (s, 1H), 3.86-3.73 (m, 2H), 2.85 (d, J=11.2 Hz, 2H), 2.77-2.37 (m, 13H), 1.96-1.77 (m, 2H), 1.73-1.59 (m, 2H), 1.52 (m, 1H), 1.43-1.32 (m, 1H); $^{13}$C NMR (100 MHz, CDCl$_3$) δ 163.11, 160.66, 138.31, 138.30, 136.99, 136.96, 129.83, 129.75, 129.29, 129.26, 128.47, 128.45, 126.38, 115.59, 115.38, 71.18, 69.48, 60.15, 59.23, 58.11, 57.69, 56.55, 53.34, 52.91, 41.61, 41.47, 29.75, 29.71, 29.69, 28.18, 26.31; FT-IR (ATR, υ, cm$^{-1}$) 3384, 3035, 1673, 1507, 1457, 1234, 1200, 1181, 1136, 1045, 800 Anal. (C$_{38}$H$_{44}$F$_2$N$_2$O$_2$S.2HCl.H$_2$O) C, H, N.

purified by flash column chromatography (0-5% MeOH/0-0.125% NH$_4$OH in CH$_2$Cl$_2$) to afford JBG01-061 (62 mg, 0.125 mmol, 23% yield) as a yellow oil. The free base was converted to the corresponding HCl salt and was recrystallized with hot isopropyl alcohol to give a yellow crystalline solid. $^1$H NMR (400 MHz, CDCl$_3$) δ 7.35-7.17 (m, 9H), 6.98 (t, J=8.4 Hz, 4H), 5.19 (s, 1H), 3.80 (m, 1H), 2.84-2.64 (m, 5H), 2.60-2.42 (m, 6H), 2.42-2.32 (m, 1H), 1.93 (m, 2H), 1.85-1.73 (m, 2H), 1.32 (m, 3H); $^{13}$C NMR (101 MHz, CDCl$_3$) δ 163.08, 160.63, 138.32, 137.06, 137.03, 129.82, 129.74, 129.32, 128.41, 126.33, 115.55, 115.34, 70.75, 57.95, 54.66, 52.86, 52.33, 51.53, 41.71, 32.94, 32.51, 29.64; FT-IR (ATR, υ, cm$^{-1}$) 3294, 2921, 1622, 1506, 1440, 1467, 1225, 1159, 1042, 1015, 844; Anal. (C$_{29}$H$_{34}$F$_2$N$_2$OS.2HCl.H$_2$O) C, H, N. The c Log P of JBG01-061 is 5.22.

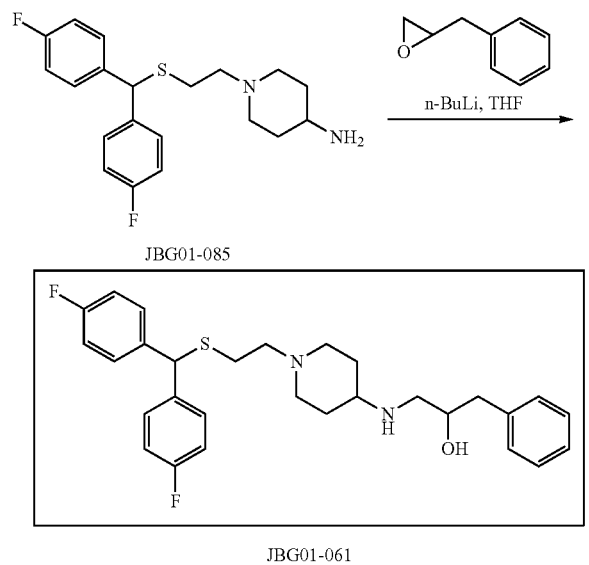

JBG01-085

JBG01-061

Synthesis of JBG01-061 [1-((1-(2-((Bis(4-fluorophenyl)methyl)thio)ethyl)piperidin-4-yl)amino)-3-phenylpropan-2-ol]

To a 25 mL pear shaped flask equipped with a stir bar was added JBG01-085 (0.200 g, 0.552 mmol) and THF (2.75 mL) under an argon atmosphere, and the reaction was permitted to stir until dissolved. The solution was cooled to 0° C. n-Butyllithium (0.43 mL, 1.15 M) was added dropwise via syringe and was permitted to stir for 15 minutes at 0° C. A precooled solution of 2-benzyloxirane (0.066 mL, 0.49 mmol) in THF (0.2 mL) was added via cannula, and the reaction was stirred at 0° C. for 2 hours. The reaction was slowly warmed to room temperature and was stirred overnight, after which time it was heated to reflux for 5.5 hours. The reaction was cooled to 0° C. and quenched with a saturated solution of NH$_4$C$_1$ (15 mL). THF was removed under reduced pressure, and deionized H$_2$O was added to the reaction (60 mL). The aqueous layer was extracted with CH$_2$Cl$_2$ (3×30 mL). Combined organics were washed with brine (2×15 mL) and dried with MgSO$_4$. The crude oil was

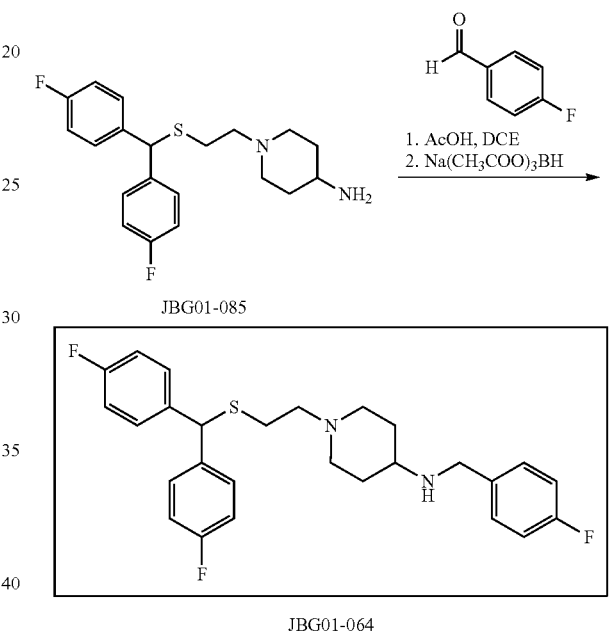

JBG01-085

JBG01-064

Synthesis of JBG01-064 [1-(2-((Bis(4-fluorophenyl)methyl)thio)ethyl)-N-(4-fluorobenzyl)piperidin-4-amine]

JBG01-064 was prepared from JBG01-085 (0.117 g, 0.323 mmol) and commercially available 4-fluorobenzaldehyde (0.035 mL, 0.323 mmol) according to the general reductive amination procedure. The crude product was purified via flash chromatography (0-5% MeOH/0-0.125% NH$_4$OH in CH$_2$Cl$_2$) to afford JBG01-064 (62 mg, 0.132 mmol, 41% yield) as a yellow oil. The free base was converted to the corresponding HCl salt and was recrystallized with hot methanol to give a colorless crystalline solid. $^1$H NMR (400 MHz, CDCl$_3$) δ 7.35 (m, 4H), 7.27 (m, 2H), 6.99 (m, 6H), 5.21 (s, 1H), 3.76 (s, 2H), 2.77 (m, 2H), 2.57-2.41 (m, 5H), 1.96 (m, 2H), 1.85 (m, 2H), 1.48-1.22 (m, 3H); $^{13}$C NMR (100 MHz, CDCl$_3$) δ 163.07, 163.04, 160.63, 160.62, 137.06, 137.03, 136.43, 136.40, 129.81, 129.73, 129.52, 129.44, 115.54, 115.33, 115.24, 115.03, 58.05, 54.04, 52.86, 52.32, 50.05, 32.66, 29.63; FT-IR (ATR, υ, cm$^{-1}$) 2928, 2803, 1724, 1602, 1505, 1466, 1293, 1221, 1156, 1097, 825; Anal. (C$_{27}$H$_{29}$F$_3$N$_2$S.2HC) C, H, N. The c Log P of JBG01-064 is 5.99.

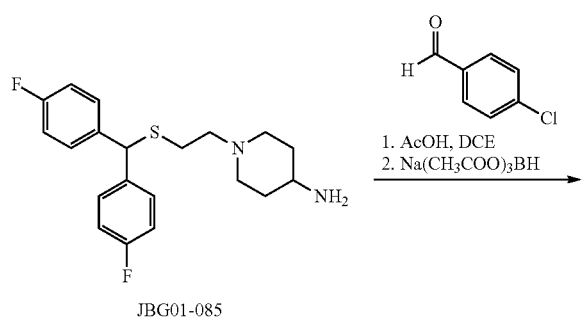
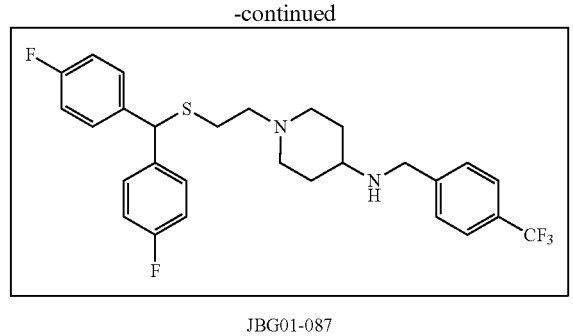

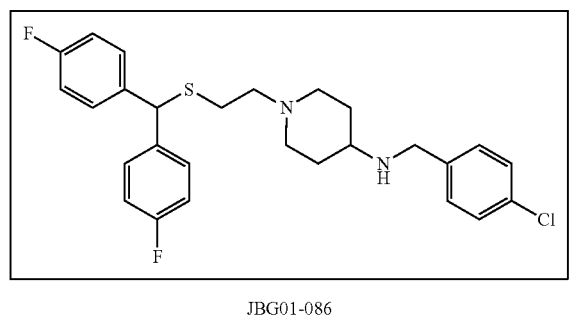

JBG01-086

Synthesis of JBG01-086 [1-(2-((Bis(4-fluorophenyl)methyl)thio)ethyl)-N-(4-chlorobenzyl)piperidin-4-amine]

JBG01-086 was prepared from JBG01-085 (0.175 g, 0.483 mmol) and commercially available 4-chlorobenzaldehyde (68 mg, 0.48 mmol) according to the general reductive amination procedure. The crude product was purified via flash chromatography (0-5% MeOH/0-0.125% NH$_4$OH in CH$_2$Cl$_2$) to afford JBG01-086 (133 mg, 0.273 mmol, 57% yield) as a yellow oil. The free base was converted to the corresponding HCl salt and was recrystallized with hot methanol to give a colorless crystalline solid. $^1$H NMR (400 MHz, CDCl$_3$) δ 7.35 (m, 4H), 7.26 (m, 4H), 6.98 (m, 4H), 5.21 (s, 1H), 3.75 (s, 2H), 2.76 (m, 2H), 2.56-2.40 (m, 5H), 1.95 (m, 2H), 1.84 (m, 2H), 1.45-1.32 (m, 2H); $^{13}$C NMR (100 MHz, CDCl$_3$) δ 163.07, 160.62, 139.20, 137.09, 137.06, 132.49, 129.83, 129.75, 129.35, 128.47, 128.45, 115.54, 115.33, 58.04, 54.02, 52.85, 52.29, 50.02, 32.62, 29.63; FT-IR (ATR, 1, cm$^{-1}$) 2925, 2802, 1712, 1601, 1504, 1466, 1358, 1221, 1156, 1095, 990, 825; Anal. (C$_{27}$H$_{29}$ClF$_2$N$_2$S.2HCl) C, H, N. The c Log P of JBG01-086 is 6.69.

Synthesis of JBG01-087 [1-(2-((Bis(4-fluorophenyl)methyl)thio)ethyl)-N-(4-(trifluoromethyl)benzyl)piperidin-4-amine]

JBG01-087 was prepared from JBG01-085 (175 mg, 0.483 mmol) and commercially available 4-(trifluoromethyl)benzaldehyde (0.066 mL, 0.48 mmol) according to the general reductive amination procedure. The crude product was purified via flash chromatography (0-5% MeOHO-0.125% NH$_4$OH in CH$_2$Cl$_2$) to afford JBG01-087 (179 mg, 0.344 mmol, 71% yield) as a yellow oil. The free base was converted to the corresponding HCl salt and was recrystallized with hot isopropyl alcohol to give a colorless crystalline solid. $^1$H NMR (400 MHz, CDCl$_3$) δ 7.56 (d, J=8.1 Hz, 2H), 7.43 (d, J=8.0 Hz, 2H), 7.35 (m, 4H), 6.98 (m, 4H), 5.22 (s, 1H), 3.85 (s, 2H), 2.77 (m, 2H), 2.57-2.40 (m, 5H), 1.96 (m, 2H), 1.85 (m, 2H), 1.39 (m, 2H), 1.31-1.22 (m, 1H); $^{13}$C NMR (100 MHz, CDCl$_3$) δ 163.07, 160.63, 145.03, 145.02, 137.10, 137.06, 129.83, 129.75, 128.16, 125.31, 125.27, 125.23, 125.20, 115.54, 115.33, 58.02, 54.13, 52.86, 52.28, 50.24, 32.69, 29.66; FT-IR (ATR, υ, cm$^{-1}$) 2936, 2904, 1713, 1602, 1505, 1323, 1222, 1157, 1119, 1017, 825; Anal. (C$_{28}$H$_{29}$F$_5$N$_2$S.2HCl) C, H, N. The c Log P of JBG01-087 is 6.86.

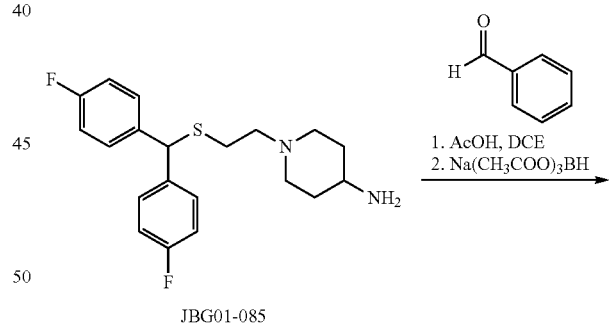
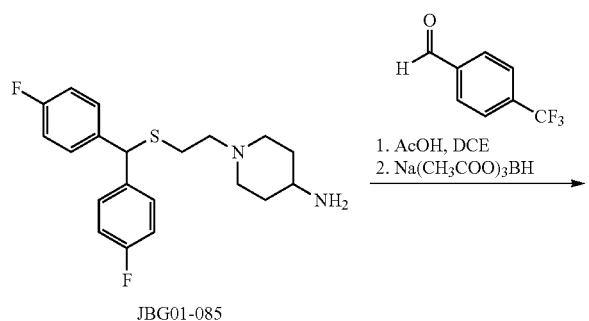
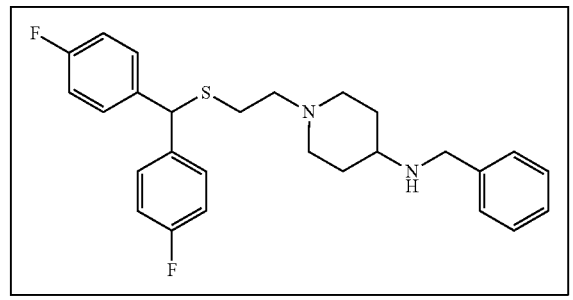

Synthesis of JBG01-057 [N-Benzyl-1-(2-((bis(4-fluorophenyl)methyl)thio)ethyl)piperidin-4-amine]

JBG01-057 was prepared from JBG01-085 (165 mg, 0.455 mmol) and commercially available benzaldehyde (0.046 mL, 0.46 mmol) according to the general reductive amination procedure. The crude product was purified via flash chromatography (0-5% MeOH/0-0.125% NH$_4$OH in CH$_2$Cl$_2$) to afford JBG01-057 (131 mg, 0.289 mmol, 64% yield) as a yellow oil. The free base was converted to the corresponding HCl salt and was recrystallized with hot methanol to give a colorless crystalline solid. $^1$H NMR (400 MHz, CDCl$_3$) δ 7.36 (m, 8H), 7.25 (m, 1H), 7.00 (m, 4H), 5.24 (s, 1H), 3.81 (s, 2H), 2.78 (m, 2H), 2.61-2.43 (m, 5H), 1.98 (m, 2H), 1.87 (m, 2H), 1.49-1.33 (m, 2H); $^{13}$C NMR (100 MHz, CDCl$_3$) δ 163.08, 160.63, 140.75, 137.12, 137.09, 129.85, 129.77, 128.41, 128.02, 126.86, 115.56, 115.34, 58.12, 54.04, 52.85, 52.35, 50.82, 32.69, 29.64; FT-IR (ATR, υ, cm$^{-1}$) 2933, 2802, 1602, 1505, 1224, 1156, 1113, 835, 745, 699; Anal. (C$_{27}$H$_{30}$F$_2$N$_2$S.2HCl.0.33H$_2$O) C, H, N. The c Log P of JBG01-057 is 5.98.

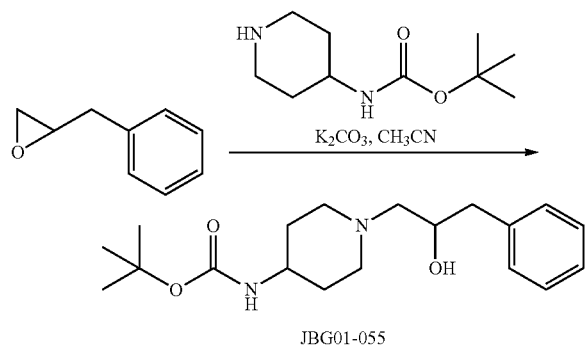

Synthesis of JBG01-055 [tert-butyl (1-(2-Hydroxy-3-phenylpropyl)piperidin-4-yl)carbamate]

To a 15 mL round bottom flask equipped with a stir bar and a condenser was added the commercially available 2-benzyloxirane (263 mg, 1.86 mmol) and K$_2$CO$_3$ (2.17 g, 14.9 mmol). Anhydrous acetonitrile (7.8 mL) was added via syringe under an argon atmosphere, and the reaction mixture was permitted to stir. Commercially available tert-butyl piperidin-4-ylcarbamate (471 mg, 2.24 mmol) was added dropwise via syringe and was refluxed overnight. The reaction mixture was cooled to 0° C. and filtered to remove residual K$_2$CO$_3$, washed with cold acetonitrile, and the filtrate was concentrated under reduced pressure. The crude oil was purified by flash column chromatography (0-5% MeOH0-0.125% NH$_4$OH in CH$_2$Cl$_2$) to afford JBG01-055 (205 mg, 0.613 mmol, 31% yield) as a colorless powder. $^1$H NMR (400 MHz, CDCl$_3$) δ 7.40-7.15 (m, 5H), 4.42 (s, 1H), 3.89 (m, 1H), 3.45 (s, 2H), 3.01-2.84 (m, 2H), 2.84-2.79 (m, 2H), 2.43-2.22 (m, 3H), 2.11-1.81 (m, 3H), 1.44 (m, 11H).

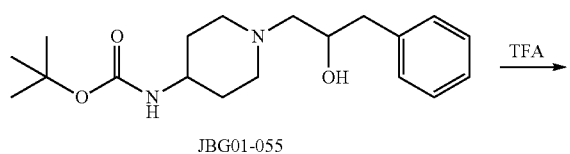

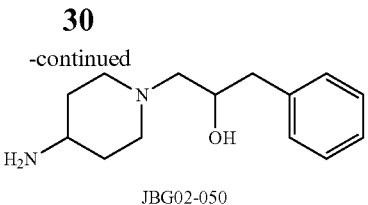

Synthesis of JBG02-050 [1-(4-Aminopiperidin-1-yl)-3-phenylpropan-2-ol]

To a 5 mL round bottom flask equipped with a stir bar and a condenser was added JBG01-055 (205 mg, 0.613 mmol) and trifluoroacetic acid (1.2 mL). The reaction was permitted to stir for 1.5 hr at room temperature under an argon atmosphere. Solvent was removed under reduced pressure, and the residue was resuspended in CH$_2$Cl$_2$ (30 mL). The organics were washed with a 30% aqueous solution of NH$_4$OH (3×5 mL, pH=9) and rinsed with brine (2×20 mL). The combined organics were dried with MgSO$_4$ and concentrated in vacuo to yield JBG02-050 (100 mg, 0.427 mmol, 70% yield). $^1$H NMR (400 MHz, CDCl$_3$) δ 7.25 (m, 5H), 3.89 (m, 1H), 3.08-2.86 (m, 1H), 2.86-2.76 (m, 1H), 3.76-2.54 (m, 4H), 2.43-2.22 (m, 3H), 2.22-1.85 (m, 2H), 1.85-1.69 (m, 2H), 1.53-1.17 (m, 3H).

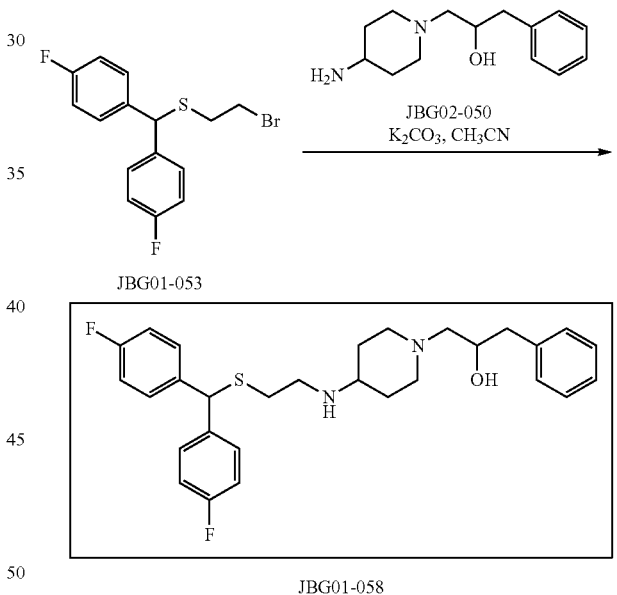

Synthesis of JBG01-058 [1-(4-((2-((Bis(4-fluorophenyl)methyl)thio)ethyl)amino)piperidin-1-yl)-3-phenylpropan-2-ol]

To a 10 mL round bottom flask equipped with a stir bar and a condenser was added (bis(4-fluorophenyl)methyl)(2-bromoethyl)sulfane (122 mg, 0.355 mmol) and K$_2$CO$_3$ (394 mg, 2.85 mmol). Anhydrous acetonitrile (1.4 mL) was added via syringe under an argon atmosphere, and the reaction mixture was permitted to stir. JBG02-050 (100 mg, 0.427 mmol) was added dropwise via syringe and was stirred for 4.5 hours at reflux. The reaction mixture was cooled to 0° C. and filtered to remove residual K$_2$CO$_3$, washed with cold acetonitrile, and the filtrate was concentrated under reduced pressure. The crude oil was purified by flash column chromatography (0-10% MeOH/0-0.25% NH$_4$OH in CH$_2$Cl$_2$) to afford JBG01-058 (120 mg, 0.242 mmol, 68% yield) as a yellow oil. The free base was converted to the corresponding HCl salt to give a colorless crystalline solid. $^1$H NMR (400 MHz, CDCl$_3$) δ 7.42-7.32 (m, 4H), 7.32-7.25 (m, 2H), 7.25-7.18 (m, 3H), 7.00 (m, 4H), 5.14 (s, 1H), 3.89 (m, 1H), 2.92 (m, 1H), 2.82 (dd, J=13.7, 7.0 Hz, 1H), 2.74 (t, J=6.5 Hz, 3H), 2.66 (dd, J=13.7, 5.6 Hz, 1H), 2.62-2.49 (m, 2H), 2.48-2.21 (m, 4H), 1.92 (m, 1H), 1.78 (m, 2H), 1.44-1.22 (m, 2H); $^{13}$C NMR (100 MHz, CDCl$_3$) δ 163.11, 160.66, 138.36, 136.97, 136.94, 129.82, 129.78, 129.74, 129.70, 129.29, 128.31, 126.24, 115.60, 115.39, 67.38, 63.41, 54.35, 53.88, 52.61, 50.92, 45.14, 41.41, 33.04, 32.98, 32.68; FT-IR (ATR, υ, cm$^{-1}$) 3027, 2922, 2805, 1602, 1505, 1453, 1293, 1223, 1156, 1097, 1015, 835; Anal. (C$_{29}$H$_{34}$F$_2$N$_2$OS.2HCl.0.5H$_2$O) C, H, N. The c Log P of JBG01-058 is 5.31.

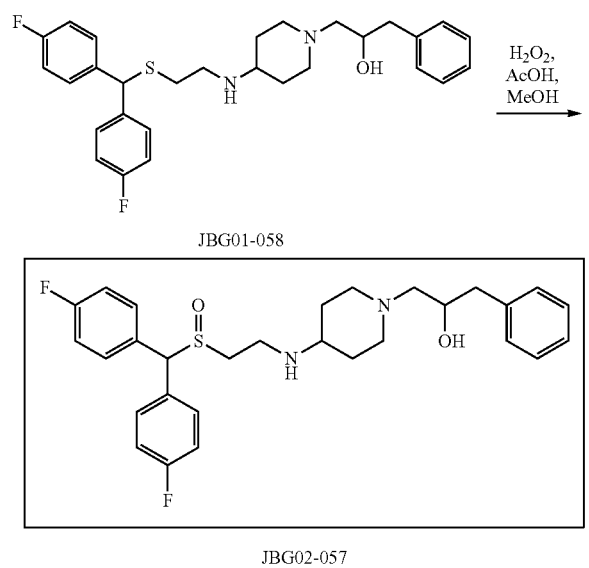

Synthesis of JBG02-057 [1-(4-((2-(((Bis(4-fluorophenyl)methyl)sulfinyl)ethyl)amino)piperidin-1-yl)-3-phenylpropan-2-ol]

To a 15 mL round bottom flask equipped with a stir bar and a condenser was added JBG01-058 (100 mg, 0.201 mmol) and methanol (0.76 mL), and the reaction mixture was permitted to stir until dissolved. Acetic acid (0.25 mL) was added dropwise via syringe under an argon atmosphere and was stirred for 5 minutes. H$_2$O$_2$ (30% in H$_2$O, 0.020 mL, 0.20 mmol) was added dropwise via syringe, and the reaction was stirred overnight at 40° C. The reaction was quenched with deionized H$_2$O (5 mL) and solvent was removed in vacuo. The aqueous layer was made basic (pH=8) by the addition of NaHCO$_3$ (25 mL), and the reaction was extracted with CH$_2$Cl$_2$ (3×50 mL). Combined organics were dried with MgSO$_4$ and the crude oil was purified by flash column chromatography (0-5% MeOH/0-0.125% NH$_4$OH in CH$_2$C$_2$) to afford JBG02-057 (47 mg, 0.092 mmol, 46% yield). The free base was converted to the corresponding HCl salt to give a yellow solid. $^1$H NMR (400 MHz, CDCl$_3$) δ 7.40 (m, 4H), 7.28 (m, 2H), 7.21 (m, 3H), 7.08 (m, 4H), 4.89 (s, 1H), 3.93 (m, 1H), 3.07-3.03 (m, 2H), 2.97-2.94 (m, 1H), 2.85-2.71 (m, 2H), 2.70-2.56 (m, 3H), 2.48 (m, 1H), 2.41-2.30 (m, 3H), 2.10-1.96 (m, 1H), 1.85 (m, 2H), 1.50-1.17 (m, 2H); $^{13}$C NMR (100 MHz, CDCl$_3$) δ 164.01, 163.78, 161.55, 161.31, 138.12, 131.47, 131.44, 131.03, 130.94, 130.41, 130.37, 130.34, 130.26, 129.28, 128.36, 126.32, 116.47, 116.26, 115.90, 115.78, 115.68, 70.54, 67.31, 63.35, 54.07, 53.38, 51.29, 51.28, 50.87, 41.44, 40.29, 32.28, 32.02, 31.76, 29.68; FT-IR (ATR, υ, cm$^{-1}$) 3384, 3062, 2924, 2808, 1603, 1506, 1454, 1226, 1159, 1040, 837; Anal. (C$_{29}$H$_{34}$F$_2$N$_2$O$_2$S.3HCl.H$_2$O.0.33NH$_4$OH) C, H, N; HRMS (ESI in positive mode) calculated 513.23818, found 513.23752 (+H+). The c Log P of JBG02-057 is 3.46.

General Method for Amidation:

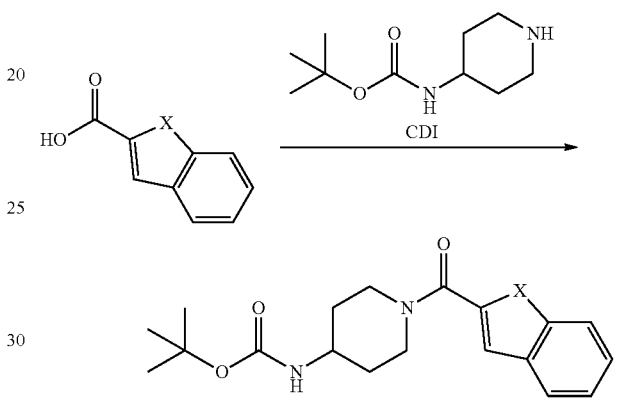

To an appropriately size round bottom flask equipped with a stir bar was added the carboxylic acid (1 eq) in anhydrous THF (0.125 M) under an argon atmosphere, and the reaction mixture was permitted to stir until dissolved. CDI (1.2 eq) was added in one portion, and the reaction was stirred for 3 hr at room temperature. The amine (1 eq) was dissolved in THF (0.2 M) and added dropwise via syringe, and the reaction was stirred overnight at room temperature. Solvent was removed, and the residue was purified via flash column chromatography to afford the desired amide product.

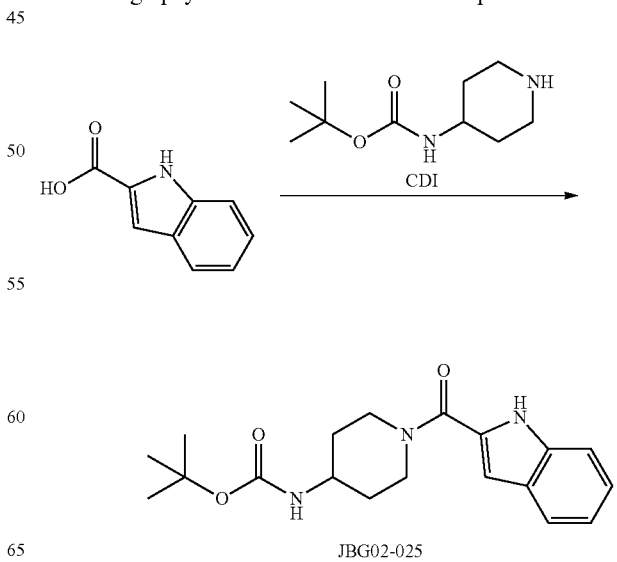

JBG02-025

Synthesis of JBG02-025 [tert-Butyl(1-(1H-indole-2-carbonyl)piperidin-4-Yl)carbamate]

JBG02-025 was prepared from commercially available 1H-indole-2-carboxylic acid (0.30 g, 1.86 mmol) and commercially available tert-butyl piperidin-4-ylcarbamate (0.373 g, 1.86 mmol) according to the general amidation procedure. The crude product was purified via flash chromatography (0-5% MeOH/0-0.125% NH$_4$OH in CH$_2$C$_2$) to afford JBG02-025 (0.528 mg, 1.54 mmol, 83% yield) as a colorless solid. $^1$H NMR (400 MHz, CDCl$_3$) δ 9.29 (s, 1H), 7.65 (m, 1H), 7.43 (m, 1H), 7.38 (m, 2H), 7.14 (m, 1H), 6.77 (m, 1H), 4.63 (d, J=13.7 Hz, 2H), 4.52 (s, 1H), 3.79 (s, 1H), 3.22 (s, 1H), 2.09 (d, J=12.9 Hz, 2H), 1.58-1.35 (m, 11H).

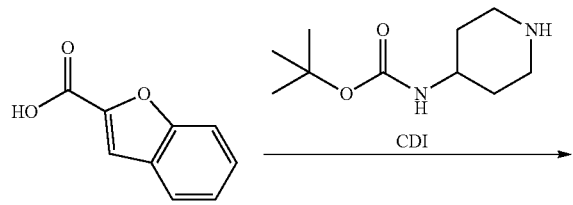

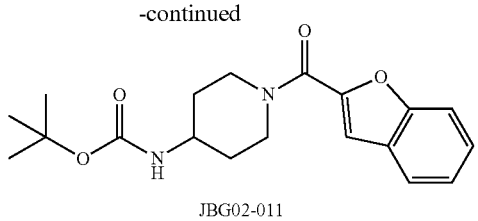

JBG02-011

Synthesis of JBG02-011 [tert-Butyl (1-(benzofuran-2-carbonyl)piperidin-4-Yl)carbamate]

JBG02-011 was prepared from commercially available benzofuran-2-carboxylic acid (500 mg, 3.08 mmol) and commercially available tert-butyl piperidin-4-ylcarbamate (618 mg, 3.08 mmol) according to the general amidation procedure. The crude product was purified via flash chromatography (0-5% MeOH/0-0.125% NH$_4$OH in CH$_2$Cl$_2$) to afford JBG02-011 (815 mg, 2.37 mmol, 77% yield) as a colorless solid. $^1$H NMR (400 MHz, CDCl$_3$) δ 7.65 (m, 1H), 7.52 (dt, J=8.4, 0.8 Hz, 1H), 7.40 (tt, J=7.6, 0.9 Hz, 1H), 7.28 (m, 3H), 4.49 (s, 3H), 3.76 (s, 1H), 3.15 (s, 1H), 2.08 (m, 2H), 1.46 (s, 11H).

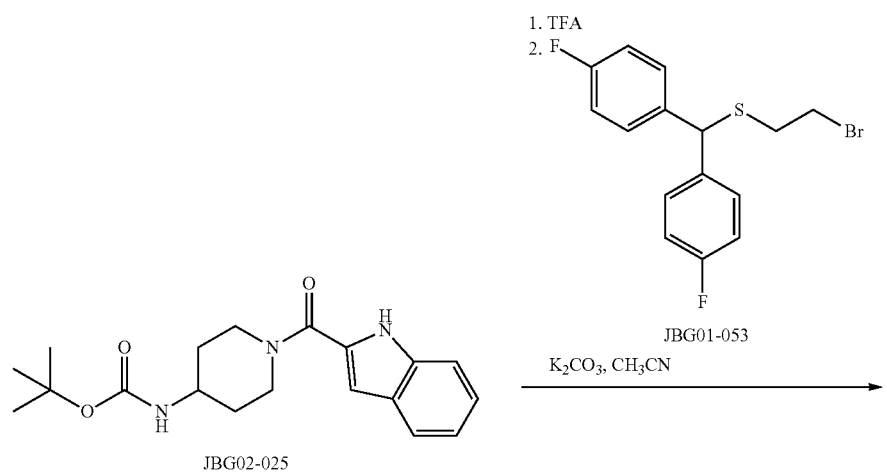

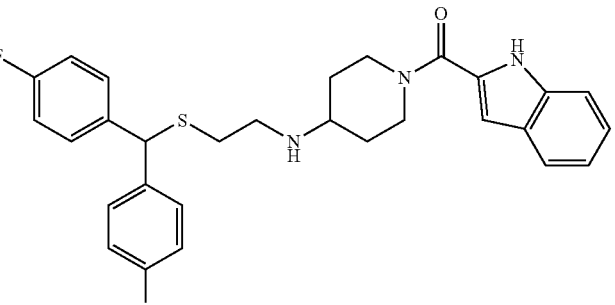

JBG02-029

Synthesis of JBG02-029 [(4-((2-((Bis(4-fluorophenyl)methyl)thio)ethyl)amino)piperidin-1-yl)(1H-indol-2-yl)methanone]

To a 15 mL round bottom flask equipped with a stir bar was added JBG02-025 (125 mg, 0.364 mmol) and trifluoroacetic acid (5 mL). The reaction was permitted to stir for 1 hr at room temperature under an argon atmosphere. Solvent was removed under reduced pressure, and the crude amine trifluoroacetic acid salt was used directly in the next step. To a 50 mL round bottom flask equipped with a stir bar and a condenser was added (bis(4-fluorophenyl)methyl)(2-bromoethyl)sulfane (125 mg, 0.364 mmol) and $K_2CO_3$ (503 mg, 3.64 mmol). Anhydrous acetonitrile (2 mL) was added via syringe at room temperature under an argon atmosphere, and the reaction mixture was permitted to stir. The crude amine salt was dissolved in anhydrous acetonitrile (5 mL) and was added dropwise via syringe at room temperature, and the reaction was stirred for 3 hours at 70° C. The reaction mixture was cooled to 0° C. and filtered to remove residual $K_2CO_3$, washed with cold acetonitrile, and the filtrate was concentrated under reduced pressure. The crude oil was purified by flash column chromatography (0-5% MeOH/0-0.125% $NH_4OH$ in $CH_2C_2$) to afford JBG02-029 (20 mg, 0.040 mmol, 11% yield) over two steps as a yellow oil. The free base was converted to the corresponding HCl salt and recrystallized from hot isopropyl alcohol to give a colorless crystalline solid. $^1H$ NMR (400 MHz, $CDCl_3$) δ 9.89 (s, 1H), 7.62 (d, J=8.1 Hz, 1H), 7.43 (d, J=8.3 Hz, 1H), 7.29 (m, 5H), 7.12 (t, J=7.5 Hz, 1H), 6.98 (td, J=8.7, 2.0 Hz, 4H), 6.70 (s, 1H), 5.11 (s, 1H), 4.56 (d, J=13.5 Hz, 2H), 3.09 (s, 2H), 2.84 (q, J=8.7, 6.6 Hz, 3H), 2.59 (t, J=6.8 Hz, 2H), 1.93 (d, J=12.9 Hz, 2H), 1.53-1.33 (m, 3H); $^{13}C$ NMR (100 MHz, $CDCl_3$) δ 163.16, 162.66, 160.71, 136.66, 136.62, 135.91, 129.78, 129.69, 129.01, 127.27, 124.38, 121.73, 120.57, 115.67, 115.46, 111.91, 105.07, 54.52, 52.76, 44.68, 31.41; FT-IR (ATR, υ, $cm^{-1}$) 3259, 1676, 1599, 1505, 1442, 1223, 1014, 828, 747, 572; Anal. ($C_{29}H_{29}F_2N_3OS \cdot 2HCl \cdot H_2O$) C, H, N. The c Log P of JBG02-029 is 4.35.

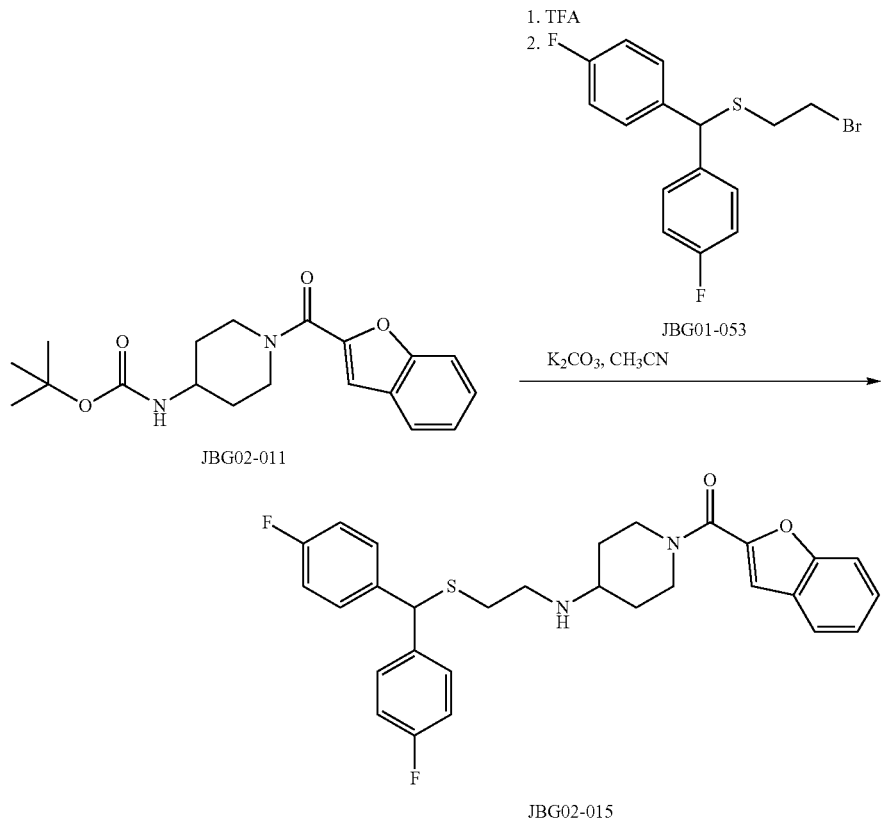

Synthesis of JBG02-015 [Benzofuran-2-yl(4-((2-((bis(4-fluorophenyl)methyl)thio)ethyl)amino)piperidin-1-yl)methanone]

To a 15 mL round bottom flask equipped with a stir bar was added JBG02-011 (200 mg, 0.581 mmol) and trifluoroacetic acid (1.2 mL). The reaction was permitted to stir for 3 hr at room temperature under an argon atmosphere. Solvent was removed under reduced pressure, and the crude amine trifluoroacetic acid salt was used directly in the next step. To a 50 mL round bottom flask equipped with a stir bar and a condenser was added (bis(4-fluorophenyl)methyl)(2-bromoethyl)sulfane (354 mg, 1.03 mmol) and $K_2CO_3$ (1.43 g, 10.3 mmol). Anhydrous acetonitrile (2 mL) was added via syringe at room temperature under an argon atmosphere, and the reaction mixture was permitted to stir. The crude amine salt was dissolved in anhydrous acetonitrile (5 mL) and was added dropwise via syringe at room temperature and was stirred for 3 hours at 70° C. The reaction mixture was cooled to 0° C. and filtered to remove residual $K_2CO_3$, washed with cold acetonitrile, and the filtrate was concentrated under reduced pressure. The crude oil was purified by flash column chromatography (0-5% MeOH/0-0.125% $NH_4OH$ in CH$_2$Cl$_2$) to afford JBG02-015 (86 mg, 0.17 mmol, 29% yield) over two steps as a yellow oil. The free base was converted to the corresponding HCl salt and recrystallized from hot isopropyl alcohol to give a to give a colorless crystalline solid. $^1$H NMR (400 MHz, CDCl$_3$) δ 7.64 (m, 1H), 7.52 (m, 1H), 7.42-7.32 (m, 5H), 7.31-7.23 (m, 2H), 7.05-6.96 (m, 4H), 5.15 (s, 1H), 4.42 (s, 2H), 3.40-2.89 (m, 2H), 2.81-2.78 (t, J=6.4 Hz, 2H), 2.73-2.71 (m, 1H), 2.56 (t, J=6.4 Hz, 2H), 1.92 (m, 2H), 1.50-1.28 (m, 3H); $^{13}$C NMR (100 MHz, CDCl$_3$) δ 222.21, 163.13, 160.68, 159.82, 154.52, 149.19, 136.92, 136.89, 129.78, 129.70, 127.01, 126.29, 123.52, 122.15, 115.64, 115.42, 111.83, 111.38, 54.26, 52.69, 45.16, 33.04; FT-IR (ATR, υ, cm$^{-1}$) 2920, 2853, 1627, 1562, 1504, 1435, 1361, 1256, 1221, 1156, 1111, 826; Anal. (C$_{29}$H$_{28}$F$_2$N$_2$O$_2$S.HCl.H$_2$O) C, H, N. The c Log P of JBG02-015 is 4.99.

colorless oil. The free base was converted to the corresponding HCl salt and recrystallized from hot isopropyl alcohol to give a colorless crystalline solid. $^1$H NMR (400 MHz, CDCl$_3$) δ 7.51 (d, J=7.5 Hz, 1H), 7.47 (d, J=8.0 Hz, 1H), 7.41-7.29 (m, 4H), 7.22 (m, 2H), 6.99 (m, 4H), 6.57 (s, 1H), 5.14 (s, 1H), 3.67 (s, 2H), 2.92 (d, J=11.2 Hz, 2H), 2.74 (t, J=6.6 Hz, 2H), 2.52 (t, J=6.5 Hz, 2H), 2.38 (m, 1H), 2.12 (t, J=11.4 Hz, 2H), 1.88-1.74 (m, 2H), 1.42 (m, 3H); $^{13}$C NMR (100 MHz, CDCl$_3$) δ 163.10, 160.65, 155.03, 154.86, 136.96, 136.93, 129.79, 129.71, 128.30, 123.84, 122.61, 120.64, 115.64, 115.60, 115.43, 115.38, 111.28, 105.45, 55.46, 54.29, 52.53, 52.52, 52.29, 45.11, 32.98, 32.60; FT-IR (ATR, υ, cm$^{-1}$) 2936, 2807, 1602, 1505, 1454, 1371, 1224, 1156, 1098, 829, 751; Anal. (C$_{29}$H$_{30}$F$_2$N$_2$OS.2HCl.H$_2$O) C, H, N. The c Log P of JBG02-018 is 6.36.

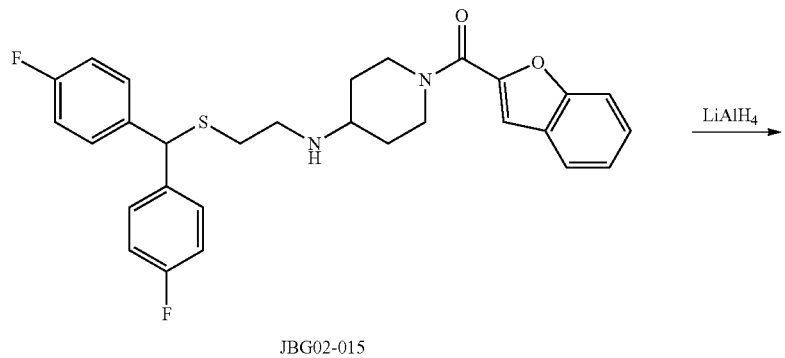

JBG02-015

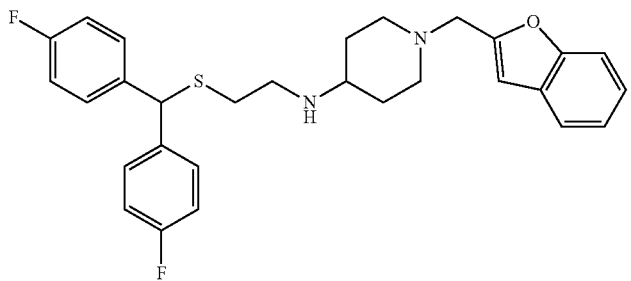

JBG02-018

Synthesis of JBG02-018 [1-(Benzofuran-2-ylmethyl)-N-(2-((bis(4-fluorophenyl)methyl)thio)ethyl)piperidin-4-amine]

To an oven-dried 25 mL round bottom flask equipped with a stir containing a suspension of LiAlH$_4$ (24 mg, 0.63 mmol) in anhydrous THF (2.5 mL) was added a solution of JBG02-015 (112 mg, 0.221 mmol) in anhydrous THF (2.5 mL) at 0° C. The reaction was permitted to slowly warm to room temperature and stirred for 6 hours, upon which time the reaction was quenched with a solution of MeOH/2N NaOH (1:1, 2 mL). The reaction mixture was filtered over a pad of celite, and the filtrate was concentrated under reduced pressure. The crude oil was purified by flash column chromatography (0-5% MeOH/0-0.125% NH$_4$OH in CH$_2$Cl$_2$) to afford JBG02-018 (49 mg, 0.099 mmol, 45% yield) as a

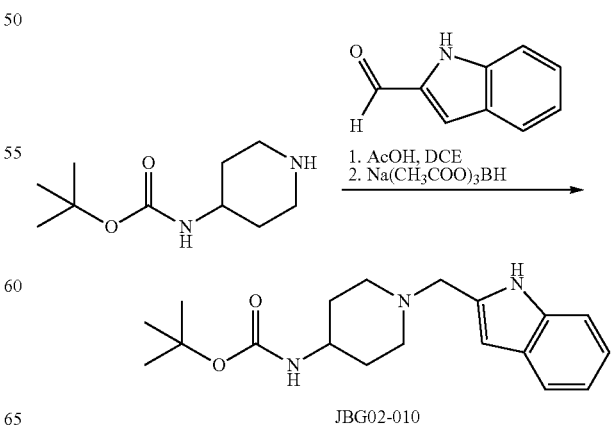

JBG02-010

Synthesis of JBG02-010 [tert-butyl (1-((1H-Indol-2-yl)methyl)piperidin-4-yl)carbamate]

JBG02-010 was prepared from commercially available tert-butyl piperidin-4-ylcarbamate (500 mg, 2.50 mmol) and commercially available 1H-indole-2-carbaldehyde (362 mg, 2.50 mmol) according to the general reductive amination procedure. The crude product was purified via flash chromatography (0-5% MeOH/0-0.125% NH$_4$OH in CH$_2$Cl$_2$) to afford JBG02-010 (738 mg, 2.24 mmol, 90% yield) as a purple amorphous solid. $^1$H NMR (400 MHz, CDCl$_3$) δ 8.51 (s, 1H), 7.54 (m, 1H), 7.33 (d, J=8.1 Hz, 1H), 7.14 (m, 1H), 7.07 (m, 1H), 6.34 (d, J=1.9 Hz, 1H), 4.43 (s, 1H), 3.65 (s, 2H), 3.49 (s, 1H), 2.82 (d, J=11.5 Hz, 2H), 2.16 (t, J=11.4 Hz, 2H), 1.93 (d, J=12.7 Hz, 2H), 1.44 (s, 9H).

stirred for 4 hours at 55° C. The reaction mixture was cooled to 0° C. and filtered to remove residual K$_2$CO$_3$, washed with cold acetonitrile, and the filtrate was concentrated under reduced pressure. The crude oil was purified by flash column chromatography (0-5% MeOH/0-0.125% NH$_4$OH in CH$_2$C$_2$) to afford JBG02-014 (47 mg, 0.0956 mmol, 16% yield) over two steps as a brown semi-solid. The free base was converted to the corresponding HCl salt to give a colorless solid. $^1$H NMR (400 MHz, CDCl$_3$) δ 8.84 (s, 1H), 7.54 (d, J=7.5 Hz, 1H), 7.33 (m, 5H), 7.13 (m, 1H), 7.06 (m, 1H), 6.99 (m, 4H), 6.32 (d, J=2.0 Hz, 1H), 5.12 (s, 1H), 3.61 (d, J=7.2 Hz, 2H), 2.83 (m, 2H), 2.74 (t, J=6.5 Hz, 2H), 2.66-2.48 (m, 2H), 2.40 (m, 1H), 2.12-1.93 (m, 2H), 1.87-1.72 (m, 2H), 1.45-1.17 (m, 3H); $^{13}$C NMR (100 MHz, CDCl$_3$) δ 172.80, 163.11, 160.66, 136.97, 136.94, 136.20,

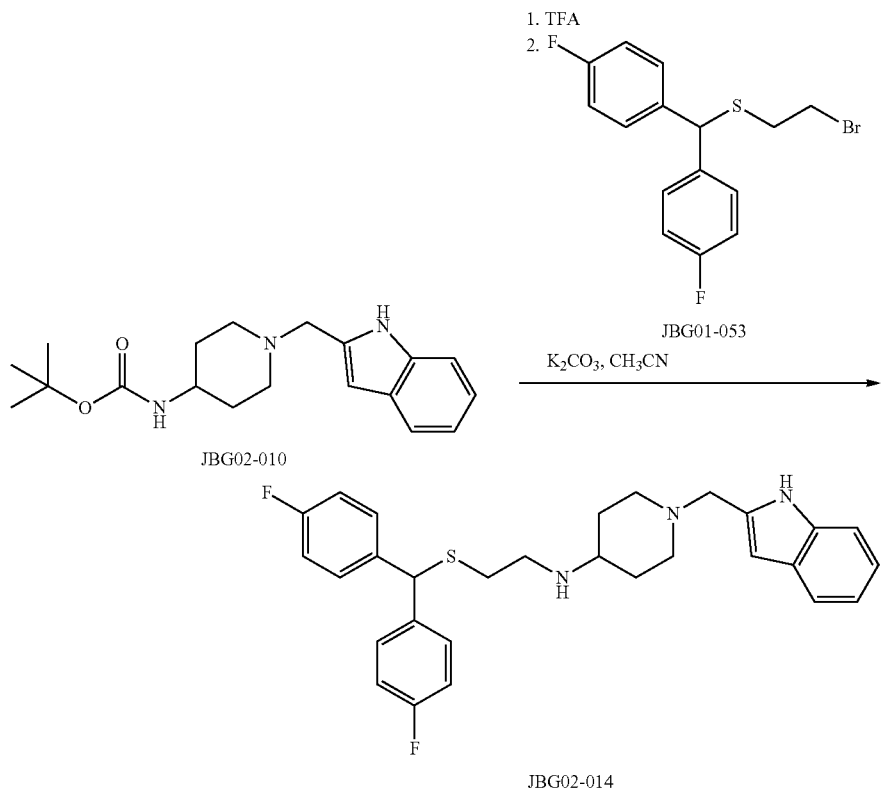

Synthesis of JBG02-014 [1-((1H-Indol-2-yl)methyl)-N-(2-((bis(4-fluorophenyl)methyl)thio)ethyl)piperidin-4-amine]

To a 15 mL round bottom flask equipped with a stir bar was added JBG02-010 (200 mg, 0.607 mmol) and trifluoroacetic acid (1.2 mL). The reaction was permitted to stir for 1 hr at room temperature under an argon atmosphere. Solvent was removed under reduced pressure, and the crude amine trifluoroacetic acid salt was used directly in the next step. To a 50 mL round bottom flask equipped with a stir bar and a condenser was added (bis(4-fluorophenyl)methyl)(2-bromoethyl)sulfane (297 mg, 0.865 mmol) and K$_2$CO$_3$ (1.20 g, 8.65 mmol). Anhydrous acetonitrile (2 mL) was added via syringe at room temperature under an argon atmosphere, and the reaction mixture was permitted to stir. The crude amine salt was dissolved in anhydrous acetonitrile (5 mL) and was added dropwise via syringe at room temperature and was 136.16, 129.79, 129.71, 128.33, 121.42, 120.06, 119.49, 115.61, 115.40, 110.76, 101.32, 55.84, 54.48, 52.58, 52.47, 45.14, 33.00, 32.70, 31.96, 22.66; FT-IR (ATR, υ, cm$^{-1}$) 3187, 2920, 2808, 1670, 1602, 1504, 1456, 1415, 1456, 1223, 1156, 1097, 826; Anal. (C$_{29}$H$_{31}$F$_2$N$_3$S.2HCl.2H$_2$O) C, H, N. The c Log P of JBG02-014 is 5.33.

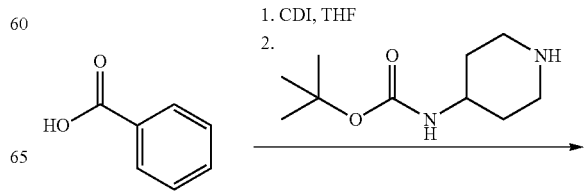

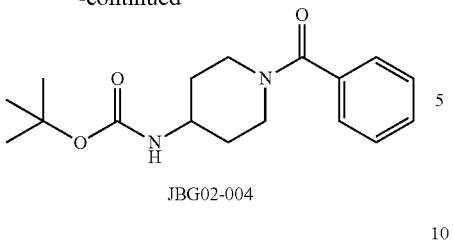

JBG02-004

Synthesis of JBG02-004 [tert-butyl (1-Benzoylpiperidin-4-yl)carbamate]

JBG02-004 was prepared from commercially available benzoic acid (500 mg, 4.09 mmol) and commercially available tert-butyl piperidin-4-ylcarbamate (820 mg, 4.09 mmol) according to the general amidation procedure. The crude product was purified via flash chromatography (0-5% MeOH/0-0.125% NH$_4$OH in CH$_2$Cl$_2$) to afford JBG02-004 (1.27 g, 4.17 mmol, quantitative yield) as a colorless solid. $^1$H NMR (400 MHz, CDCl$_3$) δ 7.45-7.33 (m, 5H), 4.55 (m, 2H), 3.71 (broad s, 2H), 3.03 (m, 2H), 2.00 (m, 2H), 1.52-1.21 (s, 11H).

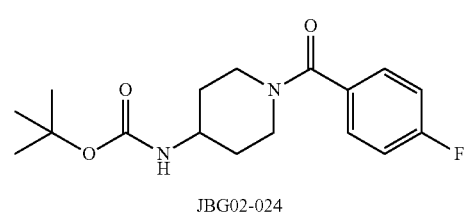

JBG02-024

Synthesis of JBG02-024 [tert-Butyl (1-(4-fluorobenzoyl)piperidin-4-yl)carbamate]

JBG02-024 was prepared from commercially available 4-fluorobenzoic acid (500 mg, 3.57 mmol) and commercially available tert-butyl piperidin-4-ylcarbamate (715 mg, 3.57 mmol) according to the general amidation procedure. The crude product was purified via flash chromatography (0-5% MeOH/0-0.125% NH$_4$OH in CH$_2$Cl$_2$) to afford JBG02-004 (982 mg, 3.05 mmol, 85% yield) as a colorless solid. $^1$H NMR (400 MHz, CDCl$_3$) δ 7.39 (m, 2H), 7.09 (m, 2H), 4.51 (broads, 2H), 3.71 (s, 2H), 3.03 (broad s, 2H), 2.11-1.85 (m, 2H), 1.45 (m, 11H).

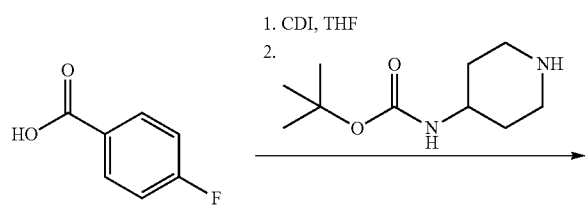

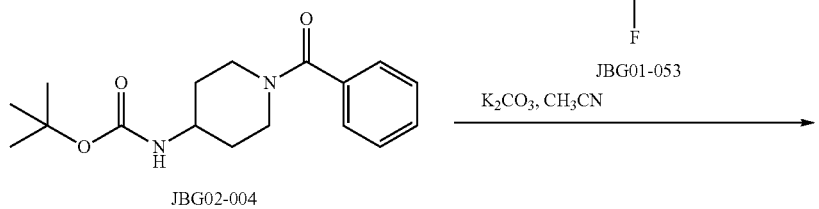

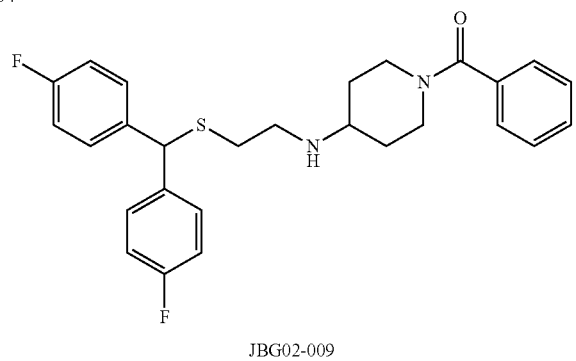

JBG02-009

Synthesis of JBG02-009 [(4-((2-((Bis(4-fluorophenyl)methyl)thio)ethyl)amino)piperidin-1-yl)(phenyl)methanone]

To a 25 mL round bottom flask equipped with a stir bar was added JBG02-004 (200 mg, 0.657 mmol) and trifluoroacetic acid (1.3 mL). The reaction was permitted to stir for 1 hr at room temperature under an argon atmosphere. Solvent was removed under reduced pressure, and the crude amine trifluoroacetic acid salt was used directly in the next step. To a 50 mL round bottom flask equipped with a stir bar and a condenser was added the crude amine salt and K$_2$CO$_3$ (1.04 g, 7.51 mmol). Anhydrous acetonitrile (1 mL) was added via syringe under an argon atmosphere, and the reaction mixture was permitted to stir at room temperature. (bis(4-fluorophenyl)methyl)(2-bromoethyl)sulfane (258 mg, 0.751 mmol) was dissolved in anhydrous acetonitrile (2 mL) and was added dropwise via syringe at room temperature and was stirred for 3 hours at reflux. The reaction mixture was cooled to 0° C. and filtered to remove residual K$_2$CO$_3$, washed with cold acetonitrile, and the filtrate was concentrated under reduced pressure. The crude oil was purified by flash column chromatography (0-5% MeOH/0-0.125% NH$_4$OH in CH$_2$Cl$_2$) to afford JBG02-009 (74 mg, 0.159 mmol, 24% yield) over two steps. The free base was converted to the corresponding HCl salt and recrystallized from hot isopropyl alcohol to give a colorless crystalline solid. $^1$H NMR (400 MHz, CDCl$_3$) δ 7.41-7.33 (m, 9H), 7.00 (m, 4H), 5.14 (s, 1H), 4.54 (s, 1H), 3.82-3.60 (m, 1H), 2.99 (s, 2H), 2.77 (t, J=6.5 Hz, 2H), 2.72-2.58 (m, 1H), 2.55 (t, J=6.4 Hz, 2H), 2.01-1.67 (m, 2H), 1.57-1.16 (m, 3H); $^{13}$C NMR (100 MHz, CDCl$_3$) δ 170.29, 163.11, 160.66, 136.91, 136.88, 136.18, 129.81, 129.76, 129.74, 129.68, 129.51, 128.44, 126.76, 115.66, 115.62, 115.44, 115.41, 54.35, 52.67, 45.12; FT-IR (ATR, υ, cm$^{-1}$) 2921, 2853, 1712, 1625, 1601, 1504, 1434, 1275, 1221, 1156, 1098, 1074, 826; Anal. (C$_{27}$H$_{28}$F$_2$N$_2$OS.HCl.0.25H$_2$O) C, H, N. The c Log P of JBG02-009 is 4.43.

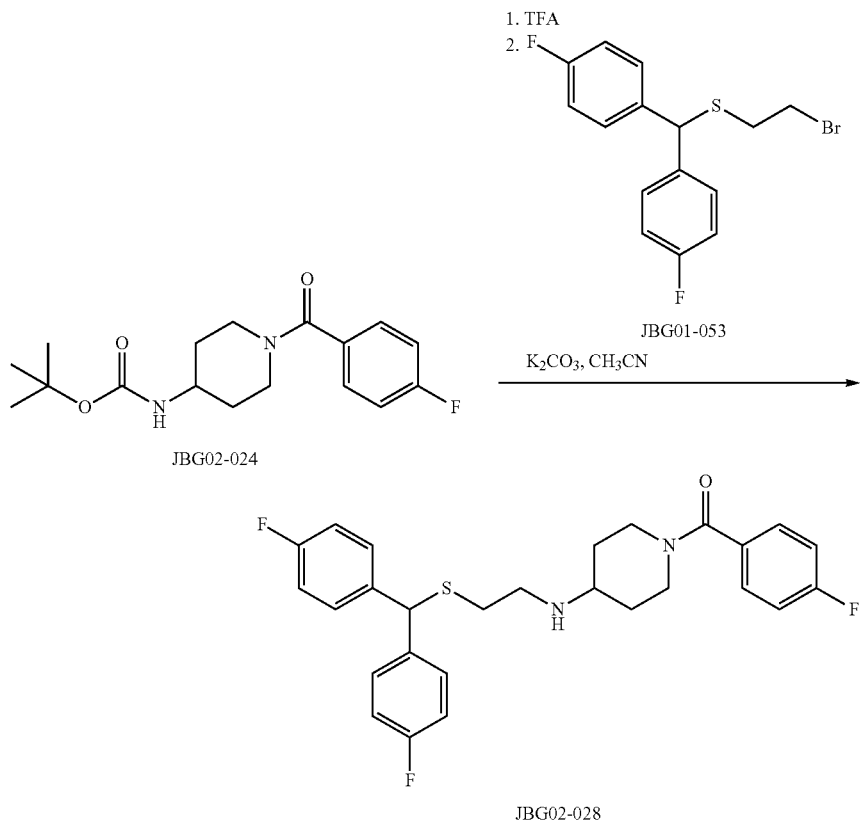

Synthesis of JBG02-028 [(4-((2-((Bis(4-fluorophenyl)methyl)thio)ethyl)amino)piperidin-1-yl)(4-fluorophenyl)methanone]

To a 25 mL round bottom flask equipped with a stir bar was added JBG02-024 (200 mg, 0.620 mmol) and trifluoroacetic acid (5 mL). The reaction was permitted to stir for 1 hr at room temperature under an argon atmosphere. Solvent was removed under reduced pressure, and the crude amine trifluoroacetic acid salt was used directly in the next step. To a 50 mL round bottom flask equipped with a stir bar and a condenser was added (bis(4-fluorophenyl)methyl)(2-bromoethyl)sulfane (213 mg, 0.621 mmol) and K$_2$CO$_3$ (858 mg, 6.21 mmol). Anhydrous acetonitrile (2 mL) was added via syringe at room temperature under an argon atmosphere, and the reaction mixture was permitted to stir. The crude amine salt was dissolved in anhydrous acetonitrile (5 mL) and was added dropwise via syringe at room temperature and was stirred for 3 hours at 70° C. The reaction mixture was cooled to 0° C. and filtered to remove residual K$_2$CO$_3$, washed with cold acetonitrile, and the filtrate was concentrated under reduced pressure. The crude oil was purified by flash column chromatography (0-5% MeOH/0-0.125% NH$_4$OH in CH$_2$Cl$_2$) to afford JBG02-028 (55 mg, 0.114 mmol, 18% yield) over two steps as a colorless solid. The free base was recrystallized from hot isopropyl alcohol to colorless crystalline solid. $^1$H NMR (400 MHz, CDC$_3$/MeOD) δ 7.38 (m, 6H), 7.11 (m, 2H), 7.02 (m, 4H), 5.19 (s, 1H), 4.60 (s, 1H), 3.77 (s, 3H), 3.21-2.75 (m, 2H), 2.87 (t, J=6.89 Hz, 2H), 2.63 (t, J=6.9 Hz, 2H), 2.00 (m, 2H), 1.42 (m, 2H); $^{13}$C NMR (100 MHz, CDCl$_3$/MeOD) δ 170.18, 164.95, 163.37, 162.46, 160.92, 136.74, 136.71, 131.46, 131.42, 129.95, 129.87, 129.31, 129.22, 115.98, 115.83, 115.77, 115.61, 54.59, 52.80, 44.38, 30.73; FT-IR (ATR, υ, cm$^{-1}$) 2923, 1673, 1602, 1505, 1440, 1371, 1222, 1131, 1014, 908, 827; Anal. (C$_{27}$H$_{27}$F$_3$N$_2$OS.CH$_2$Cl$_2$.0.5H$_2$O) C, H, N. The c Log P of JBG02-028 is 4.65.

mmol) was added dropwise via syringe, and the reaction was stirred overnight at 40° C. The reaction was quenched with deionized H$_2$O (5 mL) and solvent was removed in vacuo. The aqueous layer was made basic (pH=8) by the addition of NaHCO$_3$ (25 mL), and the reaction was extracted with CH$_2$Cl$_2$ (3×50 mL). Combined organics were dried with MgSO$_4$ and the crude oil was purified by flash column chromatography (0-5% MeOH/0-0.125% NH$_4$OH in CH$_2$C$_2$) to afford JBG02-055 (268 mg, 0.555 mmol, 60% yield). The free base was converted to the corresponding HCl salt to give a colorless solid. $^1$H NMR (400 MHz, CDCl$_3$) δ 7.40 (m, 9H), 7.09 (m, 4H), 4.88 (s, 1H), 4.50 (s,

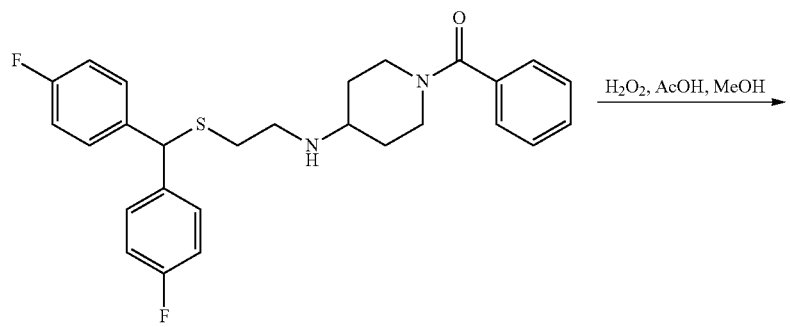

JBG02-009

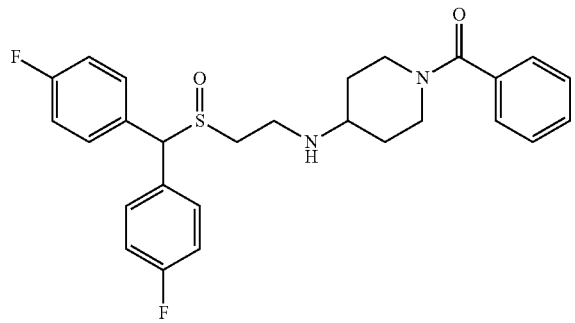

JBG02-055

Synthesis of JBG02-055 [(4-((2-((Bis(4-fluorophenyl)methyl)sulfinyl)ethyl)amino)piperidin-1-yl)(phenyl)methanone]

To a 15 mL round bottom flask equipped with a stir bar and a condenser was added JBG02-009 (431 mg, 0.924 mmol) and methanol (3.5 mL), and the reaction was permitted to stir until dissolved. Acetic acid (1.2 mL) was added dropwise via syringe under an argon atmosphere and was stirred for 5 minutes. H$_2$O$_2$ (30% in H$_2$O, 0.093 mL, 0.92

1H), 3.70 (s, 1H), 3.16-2.89 (m, 4H), 2.72 (tt, J=9.8, 3.9 Hz, 1H), 2.59 (m, 2H), 2.03-1.14 (m, 5H); $^{13}$C NMR (100 MHz, CDCl$_3$) δ 170.27, 164.00, 163.77, 161.54, 161.30, 136.13, 131.52, 131.49, 131.01, 130.93, 130.44, 130.41, 130.32, 130.24, 129.51, 128.42, 126.74, 116.45, 116.24, 115.87, 115.65, 70.58, 54.54, 51.49, 40.34; FT-IR (ATR, υ, cm$^{-1}$) 3294, 3060, 2921, 1621, 1506, 1445, 1362, 1225, 1159, 1042, 1015, 837; Anal. (C$_{27}$H$_{28}$F$_2$N$_2$O$_2$S.HCl.1.25H$_2$O) C, H, N. The c Log P of JBG02-055 is 2.58.

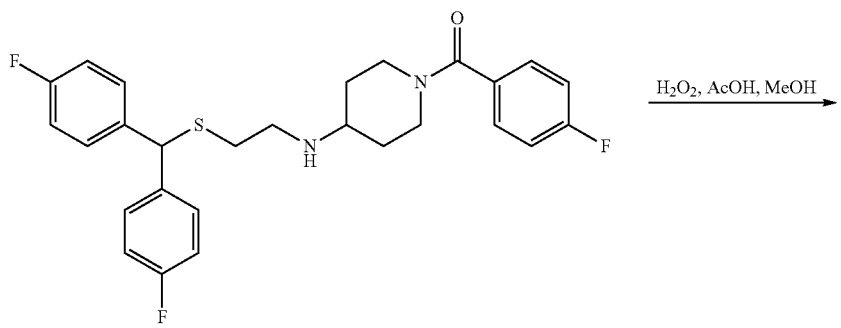

JBG02-028

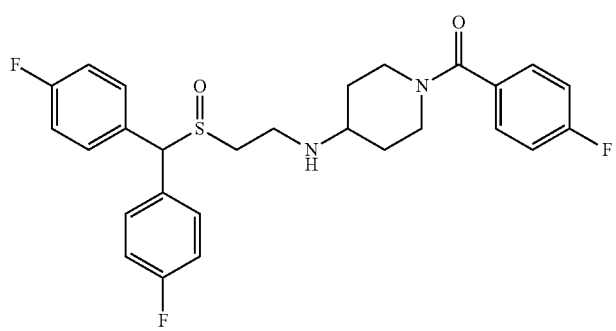

JBG02-056

Synthesis of JBG02-056 [(4-((2-((Bis(4-fluorophenyl)methyl)sulfinyl)ethyl)amino)piperidin-1-yl)(4-fluorophenyl)methanone]

To a 15 mL round bottom flask equipped with a stir bar and a condenser was added JBG02-028 (230 mg, 0.475 mmol) and methanol (1.8 mL), and the reaction was permitted to stir until dissolved. Acetic acid (0.6 mL) was added dropwise via syringe under an argon atmosphere and was stirred for 5 minutes. $H_2O_2$ (30% in $H_2O$, 0.048 mL, 0.48 mmol) was added dropwise via syringe, and the reaction was stirred overnight at 40° C. The reaction was quenched with deionized $H_2O$ (5 mL) and solvent was removed in vacuo. The aqueous layer was made basic (pH=8) by the addition of $NaHCO_3$ (25 mL), and the reaction was extracted with $CH_2Cl_2$ (3×50 mL). Combined organics were dried with $MgSO_4$ and the crude oil was purified by flash column chromatography (0-5% MeOH/0-0.125% $NH_4OH$ in $CH_2Cl_2$) to afford JBG02-056 (201 mg, 0.402 mmol, 85% yield). The free base was converted to the corresponding HCl salt to give a colorless solid. $^1H$ NMR (400 MHz, $CDCl_3$) δ 7.41 (m, 6H), 7.08 (m, 6H), 4.88 (s, 1H), 4.46 (s, 1H), 3.70 (s, 1H), 3.22-2.90 (m, 4H), 2.74 (m, 1H), 2.60 (m, 2H), 2.14-1.12 (m, 5H); $^{13}C$ NMR (100 MHz, $CDCl_3$) δ 169.38, 164.52, 164.02, 163.79, 162.04, 161.56, 161.32, 132.11, 132.07, 131.47, 131.44, 130.99, 130.91, 130.42, 130.38, 130.31, 130.23, 129.12, 129.04, 116.47, 116.26, 115.89, 115.68, 115.59, 115.38, 54.47, 51.49, 40.37; FT-IR (ATR, υ, $cm^{-1}$) 3294, 2921, 2855, 1622, 1604, 1506, 1440, 1467, 1363, 1225, 1159, 1042, 844; Anal. ($C_{27}H_{27}F_3N_2O_2S \cdot HCl \cdot 2H_2O$) C, H, N. The c Log P of JBG02-056 is 2.80.

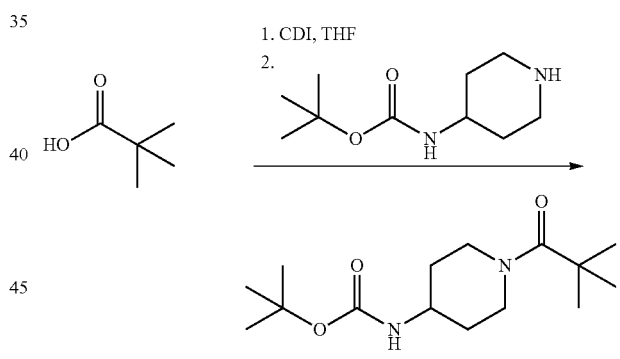

JBG02-069

Synthesis of JBG02-069 [tert-Butyl (1-pivaloylpiperidin-4-yl)carbamate]

To a 100 mL round bottom flask equipped with a stir bar was added commercially available pivalic acid (2.5 g, 24.5 mmol) and anhydrous $CH_2Cl_2$ (100 mL) under an argon atmosphere, and the reaction was permitted to stir until dissolved. EDC (7.04 g, 36.7 mmol) and HOBt (3.74 g, 27.7 mmol) were added in one portion. N,N-Diisopropylethylamine (12.8 mL) was added dropwise via syringe, and the reaction was permitted to stir for 1 hr at room temperature. Commercially available tert-butyl piperidin-4-ylcarbamate (2.0 g, 10 mmol) was added in one portion, and the reaction was stirred overnight at room temperature. The reaction was washed with $NaHCO_3$ (2×150 mL, pH=10) and rinsed with brine (1×150 mL). The organics were dried with $MgSO_4$, and the crude product was purified by flash column chromatography (0-30% ethyl acetate in hexanes) to afford JBG02-069 (2.78 g, 9.775 mmol, 98% yield) as a colorless powder. $^1$H NMR (400 MHz, CDCl$_3$) δ 4.47 (s, 1H), 4.32 (d, J=13.7 Hz, 2H), 3.68 (s, 1H), 2.92 (t, J=12.8 Hz, 2H), 1.99 (m, 2H), 1.45 (s, 9H), 1.27 (m, 11H).

(bis(4-fluorophenyl)methyl)(2-bromoethyl)sulfane (312 mg, 0.909 mmol) was dissolved in anhydrous acetonitrile (3 mL) and was added dropwise via syringe at room temperature and was stirred for 4 hours at 60° C. The reaction mixture was cooled to 0° C. and filtered to remove residual K$_2$CO$_3$, washed with cold acetonitrile, and the filtrate was concen-

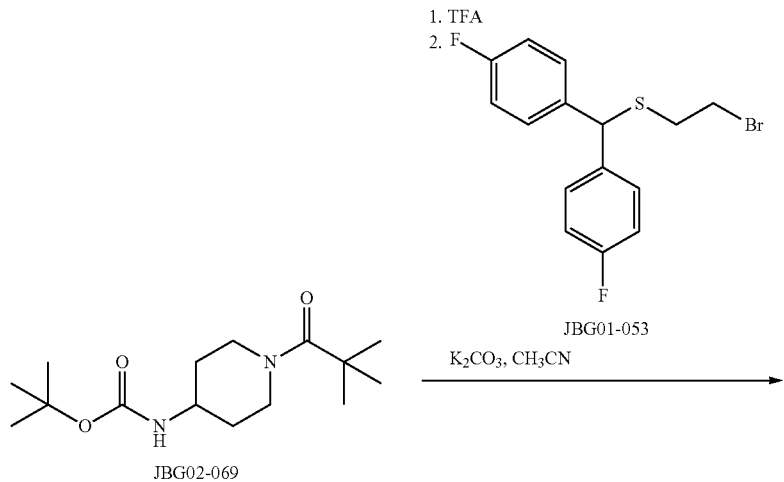

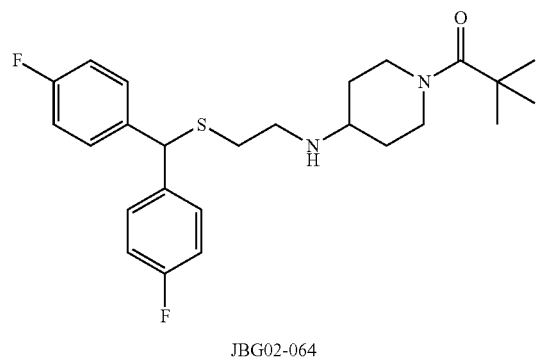

Synthesis of JBG02-064 [1-(4-((2-(((Bis(4-fluorophenyl)methyl)thio)ethyl)amino)piperidin-1-yl)-2,2-dimethylpropan-1-one]

To a 25 mL round bottom flask equipped with a stir bar was added JBG02-069 (258 mg, 0.907 mmol) and trifluoroacetic acid (2 mL). The reaction was permitted to stir for 1 hr at room temperature under an argon atmosphere. Solvent was removed under reduced pressure, and the crude amine trifluoroacetic acid salt was used directly in the next step. To a 100 mL round bottom flask equipped with a stir bar and a condenser was added the crude amine salt and K$_2$CO$_3$ (1.00 g, 7.23 mmol). Anhydrous acetonitrile (2 mL) was added via syringe at room temperature under an argon atmosphere, and the reaction mixture was permitted to stir.

trated under reduced pressure. The crude oil was purified by flash column chromatography (0-10% MeOH/0-0.25% NH$_4$OH in CH$_2$C$_2$) to afford JBG02-064 (119 mg, 0.266 mmol, 29% yield) over two steps as a colorless oil. The free base was converted to the corresponding HCl salt to give a yellow solid. $^1$H NMR (400 MHz, CDCl$_3$) δ 7.37 (m, 4H), 7.00 (t, J=8.6 Hz, 4H), 5.16 (s, 1H), 4.32 (d, J=13.5 Hz, 2H), 3.25 (s, 1H), 2.95-2.73 (m, 4H), 2.67 (m, 1H), 2.58 (t, J=6.6 Hz, 2H), 1.85 (d, J=12.8 Hz, 2H), 1.26 (s, 11H); $^{13}$C NMR (100 MHz, CDCl$_3$) δ 176.14, 163.09, 160.63, 136.89, 136.86, 129.77, 129.69, 115.59, 115.37, 54.52, 52.63, 44.84, 43.70, 38.64, 32.55, 32.42, 28.36; FT-IR (ATR, υ, cm$^{-1}$) 293, 1621, 1505, 1479, 1421, 1364, 1272, 1223, 1157, 1183, 1098, 1014, 835; Anal. (C$_{25}$H$_{32}$F$_2$N$_2$OS.HCl.H$_2$O) C, H, N. The c Log P of JBG02-064 is 3.85.

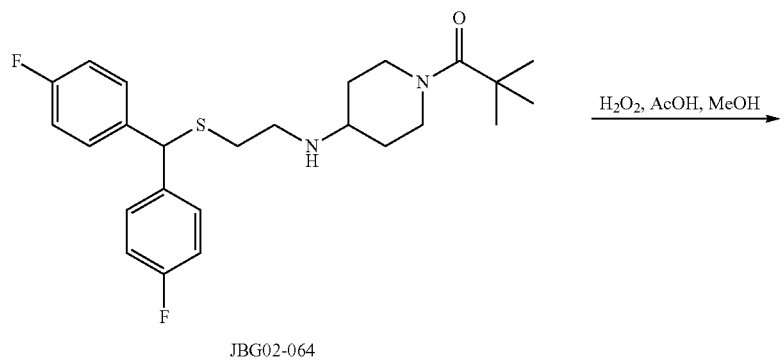

JBG02-064

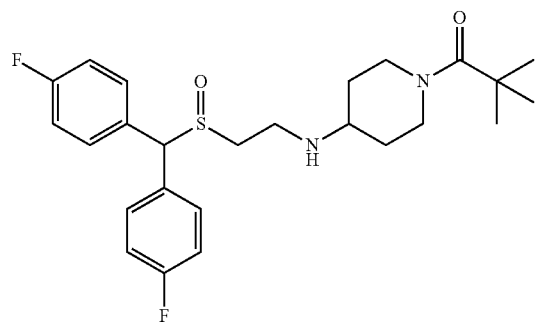

JBG02-072

Synthesis of JBG02-072 [1-(4-((2-((Bis(4-fluorophenyl)methyl)sulfinyl)ethyl)amino)piperidin-1-yl)-2,2-dimethylpropan-1-one]

To a 15 mL round bottom flask equipped with a stir bar was added JBG02-064 (200 mg, 0.448 mmol) and methanol (1.7 mL), and the reaction was permitted to stir until dissolved. Acetic acid (0.6 mL) was added dropwise via syringe and was stirred for 5 minutes. $H_2O_2$ (30% in $H_2O$, 0.045 mL, 0.45 mmol) was added dropwise via syringe, and the reaction was stirred for 60 hours at room temperature. The reaction was quenched with deionized $H_2O$ (1 mL) and solvent was removed in vacuo. $CH_2Cl_2$ (100 mL) was added, and the aqueous layer was made basic (pH=8) by the addition of $NaHCO_3$ (25 mL). The reaction was washed with $NaHCO_3$ (1×25). Organics were dried with $MgSO_4$ and the crude oil was purified by flash column chromatography (0-5% MeOH/0-0.125% $NH_4OH$ in $CH_2Cl_2$) to afford JBG02-072 (137 mg, 0.296 mmol, 66% yield) as a yellow oil. The free base was converted to the corresponding oxalate salt and recrystallized from hot acetone to give a colorless crystalline solid. $^1H$ NMR (400 MHz, $CDCl_3$) δ 7.41 (m, 4H), 7.09 (m, 4H), 4.90 (s, 1H), 4.27 (d, J=13.4 Hz, 2H), 3.18-3.01 (m, 2H), 2.90 (t, J=12.5 Hz, 2H), 2.74-2.66 (m, 1H), 2.65-2.54 (m, 2H), 1.88-1.84 (m, 3H), 1.84-1.62 (m, 1H), 1.26 (s, 11H); $^{13}C$ NMR (100 MHz, $CDCl_3$) δ 176.12, 163.98, 163.75, 161.51, 161.28, 131.50, 131.47, 131.00, 130.92, 130.43, 130.40, 130.31, 130.23, 116.43, 116.22, 115.85, 115.63, 70.55, 54.75, 51.48, 43.68, 43.56, 40.30, 38.63, 32.77, 32.56, 28.36; FT-IR (ATR, υ, $cm^{-1}$) 3297, 2933, 1604, 1506, 1480, 1423, 1364, 1225, 1160, 1042, 1015, 836; Anal. ($C_{25}H_{32}F_2N_2O_2S.C_2H_2O_4$) C, H, N. The c Log P of JBG02-072 is 2.00.

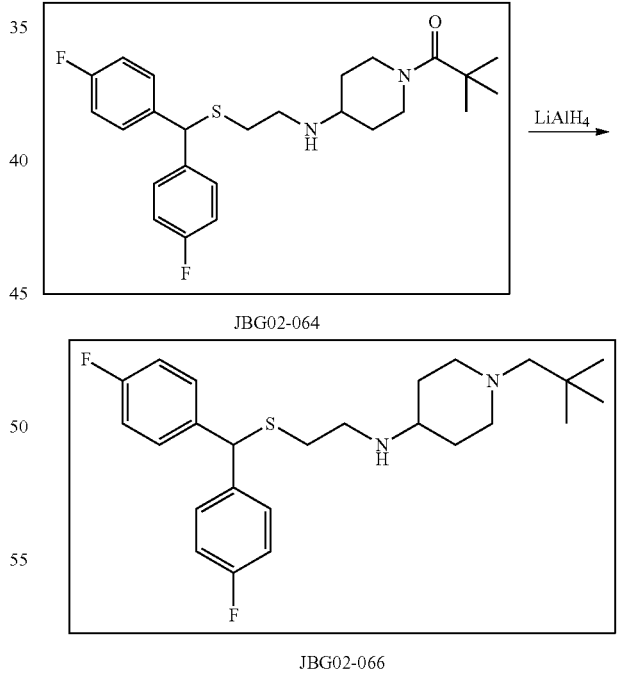

Synthesis of JBG02-066 [N-(2-((Bis(4-fluorophenyl)methyl)thio)ethyl)-1-neopentylpiperidin-4-amine]

To an oven-dried 25 mL round bottom flask equipped with a stir bar containing a suspension of $LiAlH_4$ (81 mg, 1.4 mmol) in anhydrous THF (2.5 mL) was added a solution of JBG02-064 (316 mg, 0.708 mmol) in anhydrous THF (2.5 mL) at 0° C. The reaction was permitted to slowly warm slowly to room temperature and stirred for 5 hours, upon which time it was quenched with a solution of MeOH/2N NaOH (1:1, 4 mL). The reaction mixture was filtered over a pad of celite, and the filtrate was concentrated under reduced pressure. The crude oil was purified by flash column chromatography (0-5% MeOH/0-0.125% NH$_4$OH in CH$_2$Cl$_2$) to afford JBG02-066 (142 mg, 0.328 mmol, 46% yield) as a pale yellow oil. The free base was converted to the corresponding oxalate salt to give a colorless solid. $^1$H NMR (400 MHz, CDCl$_3$) δ 7.36 (m, 4H), 6.99 (m, 4H), 5.15 (s, 1H), 2.83-2.68 (m, 4H), 2.54 (t, J=6.5 Hz, 2H), 2.33 (m, 1H), 2.21 (m, 2H), 2.02 (s, 2H), 1.79-1.64 (m, 2H), 1.50 (s, 1H), 1.34 (m, 2H), 0.84 (s, 9H); $^{13}$C NMR (100 MHz, CDCl$_3$) δ 163.09, 160.64, 137.02, 136.98, 129.82, 129.79, 129.71, 115.57, 115.36, 69.72, 55.12, 54.38, 52.55, 45.10, 33.23, 33.11, 33.05, 27.70; FT-IR (ATR, υ, cm$^{-1}$) 2949, 1603, 1505, 1466, 1381, 1225, 1156, 1108, 1015, 833, 793; Anal. (C$_{25}$H$_{34}$F$_2$N$_2$S.2C$_2$H$_2$O$_4$.0.25H$_2$O) C, H, N. The c Log P of JBG02-066 is 5.87.

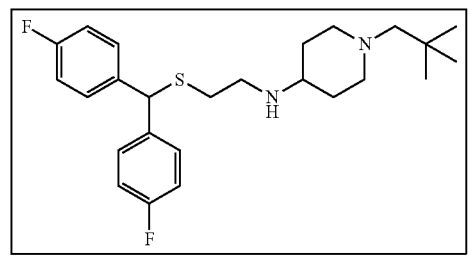

JBG02-066

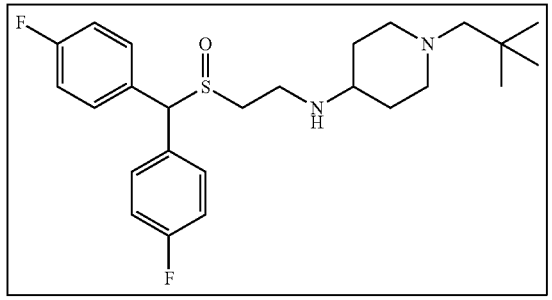

JBG02-074

Synthesis of JBG02-074 [N-(2-((Bis(4-fluorophenyl)methyl)sulfinyl)ethyl)-1-neopentylpiperidin-4-amine]

To a 15 mL round bottom flask equipped with a stir bar was added JBG02-066 (97 mg, 0.22 mmol) and methanol (0.84 mL), and the reaction was permitted to stir until dissolved. Acetic acid (0.3 mL) was added dropwise via syringe and was stirred for 5 minutes. H$_2$O$_2$ (30% in H$_2$O, 0.023 mL, 0.22 mmol) was added dropwise via syringe, and the reaction was stirred overnight at room temperature. The reaction was quenched with deionized H$_2$O (1 mL) and solvent was removed in vacuo. CH$_2$Cl$_2$ (100 mL) was added, and the aqueous layer was made basic (pH=8) by the addition of NaHCO$_3$ (25 mL). The reaction was washed with NaHCO$_3$ (2×25 mL). Organics were dried with MgSO$_4$ and the crude oil was purified by flash column chromatography (0-5% MeOH/0-0.125% NH$_4$OH in CH$_2$Cl$_2$) to afford JBG02-074 (72 mg, 0.16 mmol, 72% yield). The free base was converted to the corresponding oxalate salt and recrystallized from hot methanol to give a colorless crystalline solid. $^1$H NMR (400 MHz, CDCl$_3$) δ 7.42 (m, 4H), 7.09 (m, 4H), 4.92 (s, 1H), 3.07 (t, J=6.4 Hz, 2H), 2.74 (d, J=11.6 Hz, 2H), 2.60 (t, J=6.4 Hz, 2H), 2.37 (m, 1H), 2.21 (t, J=11.6 Hz, 2H), 2.01 (s, 2H), 1.84-1.64 (m, 3H), 1.45-1.21 (m, 2H), 0.83 (s, 9H); $^{13}$C NMR (100 MHz, CDCl$_3$) δ 164.00, 163.76, 161.53, 161.29, 131.65, 131.62, 131.05, 130.96, 130.48, 130.45, 130.36, 130.28, 116.40, 116.18, 115.84, 115.62, 70.33, 69.69, 55.01, 55.00, 54.65, 51.55, 40.16, 33.14, 33.08, 32.98, 27.68; FT-IR (ATR, υ, cm$^{-1}$) 2950, 1604, 1508, 1359, 1230, 1160, 1106, 1043, 837, 792, 573; Anal. (C$_{25}$H$_{34}$F$_2$N$_2$OS.2C$_2$H$_2$O$_4$) C, H, N. The c Log P of JBG02-074 is 4.02.

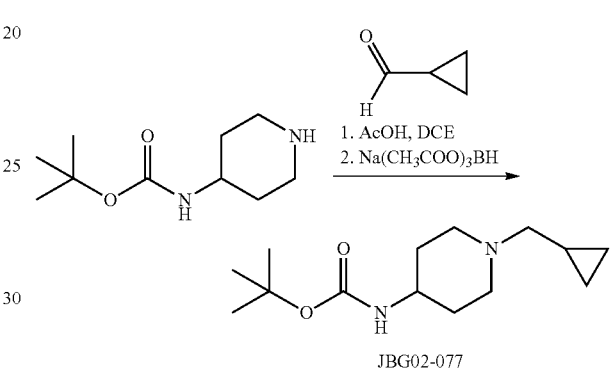

JBG02-077

Synthesis of JBG02-077 [tert-butyl (1-(cyclopropylmethyl)piperidin-4-yl)carbamate]

JBG02-077 was prepared from commercially available tert-butyl piperidin-4-ylcarbamate (400 mg, 2.00 mmol) and commercially available cyclopropanecarbaldehyde (0.149 mL, 2.00 mmol) according to the general reductive amination procedure. The crude product was purified via flash column chromatography (0-100% ethyl acetate in hexanes) to afford JBG02-077 (326 mg, 1.28 mmol, 64%). $^1$H NMR (400 MHz, CDCl$_3$) δ 4.43 (s, 1H), 3.46 (s, 1H), 2.97 (d, J=11.3 Hz, 2H), 2.23 (d, J=6.6 Hz, 2H), 2.07 (t, J=11.6 Hz, 2H), 1.94 (d, J=12.7 Hz, 2H), 1.65 (s, 1H), 1.45 (s, 10H), 0.51 (d, J=7.7 Hz, 2H), 0.09 (d, J=5.0 Hz, 2H).

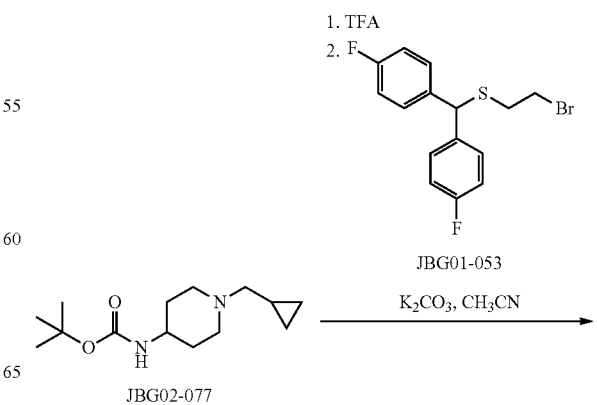

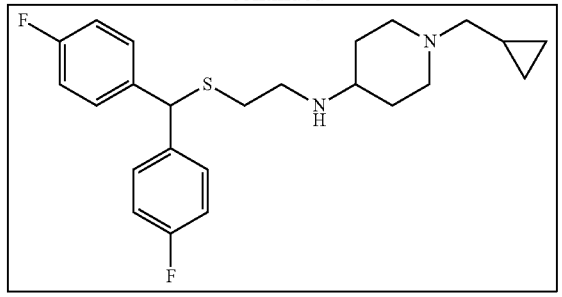

JBG02-080

Synthesis of JBG02-080 [N-(2-((bis(4-fluorophenyl)methyl)thio)ethyl)-1-(cyclopropylmethyl)piperidin-4-amine]

To a 25 mL round bottom flask equipped with a stir bar was added JBG02-077 (326 mg, 1.28 mmol) and trifluoroacetic acid (2.5 mL). The reaction was permitted to stir for 1 hr at room temperature under an argon atmosphere. Solvent was removed under reduced pressure, and the crude amine trifluoroacetic acid salt was used directly in the next step. To a 100 mL round bottom flask equipped with a stir bar and a condenser was added the crude amine salt and $K_2CO_3$ (1.42 g, 10.3 mmol). Anhydrous acetonitrile (2 mL) was added via syringe at room temperature under an argon atmosphere, and the reaction mixture was permitted to stir. (bis(4-fluorophenyl)methyl)(2-bromoethyl)sulfane (440 mg, 1.28 mmol) was dissolved in anhydrous acetonitrile (3 mL) and was added dropwise via syringe at room temperature and was stirred for 4.5 hours at 55° C. The reaction mixture was cooled to 0° C. and filtered to remove residual $K_2CO_3$, washed with cold acetonitrile, and the filtrate was concentrated under reduced pressure. The crude oil was purified by flash column chromatography (0-5% MeOH/0-0.125% $NH_4OH$ in $CH_2Cl_2$) to afford JBG02-080 (124 mg, 0.298 mmol, 23% yield) over two steps as a pale yellow oil. The free base was converted to the corresponding oxalate salt to give a colorless solid. Mp 213-218° C.; $^1H$ NMR (400 MHz, Chloroform-d) δ 7.35 (m, 4H), 7.00 (m, 4H), 5.15 (s, 1H), 3.02 (dd, J=11.6, 4.3 Hz, 2H), 2.76 (t, J=6.5 Hz, 2H), 2.54 (t, J=6.5 Hz, 2H), 2.39 (tt, J=10.3, 4.1 Hz, 1H), 2.24 (d, J=6.5 Hz, 2H), 2.01 (m, 2H), 1.90-1.76 (br m, 2H), 1.48-1.33 (m, 2H), 1.26 (s, 1H), 0.87 (dddd, J=9.6, 8.1, 5.7, 2.5 Hz, 1H), 0.51 (m, 2H), 0.10 (m, 2H); $^{13}C$ NMR (100 MHz, cdcl$_3$) δ 163.10, 160.65, 136.95, 136.92, 129.78, 129.70, 115.58, 115.37, 63.71, 54.44, 52.52, 52.39, 45.06, 32.98, 32.76, 32.57, 29.68, 8.43, 4.02, 3.97; FT-IR (ATR, υ, cm$^{-1}$) 3001, 2922, 1602, 1505, 1466, 1330, 1292, 1223, 1156, 1098, 1015, 826, 782, 572; Anal. ($C_{24}H_{30}F_2N_2S \cdot 2C_2H_2O_4 \cdot 0.5H_2O$) C, H, N. The c Log P of JBG02-080 is 4.81.

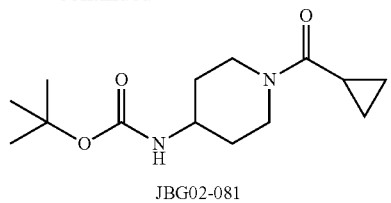

JBG02-081

Synthesis of JBG02-081 [tert-Butyl (1-(cyclopropanecarbonyl)piperidin-4-yl)carbamate]

To a 100 mL round bottom flask equipped with a stir bar was added commercially available cyclopropanecarboxylic acid (0.158 mL, 2.00 mmol) and anhydrous $CH_2Cl_2$ (50 mL) under an argon atmosphere, and the reaction was permitted to stir until dissolved. EDC (574 mg, 3.00 mmol) and HOBt (305 mg, 2.26 mmol) were added in one portion. N,N-Diisopropylethylamine (1.04 mL) was added dropwise via syringe, and the reaction was permitted to stir for 1 hr at room temperature. Commercially available tert-butyl piperidin-4-ylcarbamate (400 mg, 2.00 mmol) was added in one portion, and the reaction was stirred overnight at room temperature. The reaction was suspended with DCM (200 mL), washed with NaHCO$_3$ (2×50 mL, pH=10), and rinsed with brine (1×50 mL). The organics were dried with MgSO$_4$, and the crude product was purified by flash column chromatography (0-5% MeOH/0-0.125% NH$_4$OH in CH$_2$C$_2$) to afford JBG02-081 (535 mg, 2.00 mmol, quantitative yield) as a colorless crystalline solid. $^1H$ NMR (400 MHz, CDCl$_3$) δ 4.47 (s, 2H), 4.15 (d, J=13.1 Hz, 1H), 3.69 (s, 1H), 3.20 (t, J=12.9 Hz, 1H), 2.76 (t, J=12.4 Hz, 1H), 2.06 (dd, J=16.4, 3.5 Hz, 2H), 1.93 (d, J=12.9 Hz, 1H), 1.73 (q, J=7.8, 6.5 Hz, 1H), 1.45 (m, 9H), 1.25 (s, 1H), 1.03-0.91 (m, 2H), 0.75 (dt, J=7.6, 2.7 Hz, 2H).

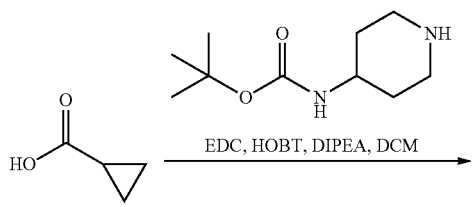

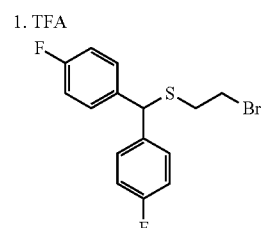

JBG01-053

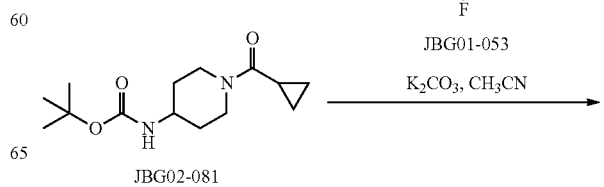

JBG02-081

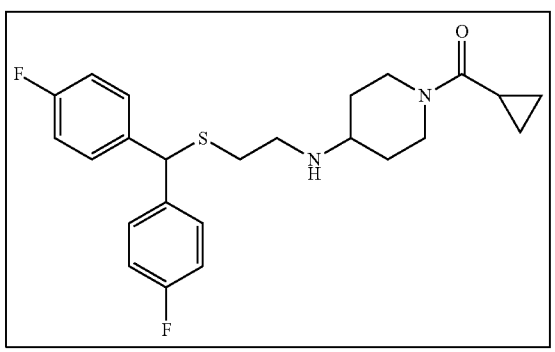

JBG02-083

Synthesis of JBG02-083 [(4-((2-((bis(4-fluorophenyl)methyl)thio)ethyl)amino)piperidin-1-yl)(cyclopropyl)methanone]

To a 25 mL round bottom flask equipped with a stir bar was added JBG02-081 (535 mg, 1.99 mmol) and trifluoroacetic acid (5 mL). The reaction was permitted to stir for 1 hr at room temperature under an argon atmosphere. Solvent was removed under reduced pressure, and the crude amine trifluoroacetic acid salt was used directly in the next step. To a 100 mL round bottom flask equipped with a stir bar and a condenser was added the crude amine salt and $K_2CO_3$ (1.794 g, 12.97 mmol). Anhydrous acetonitrile (3 mL) was added via syringe at room temperature under an argon atmosphere, and the reaction mixture was permitted to stir. (bis(4-fluorophenyl)methyl)(2-bromoethyl)sulfane (556 mg, 1.62 mmol) was dissolved in anhydrous acetonitrile (3.5 mL) and was added dropwise via syringe at room temperature and was stirred for 4.5 hours at 60° C. The reaction mixture was cooled to 0° C. and filtered to remove residual $K_2CO_3$, washed with cold acetonitrile, and the filtrate was concentrated under reduced pressure. The crude oil was purified by flash column chromatography (0-5% MeOH/0-0.125% $NH_4OH$ in $CH_2C_2$) to afford JBG02-083 (213 mg, 0.495 mmol, 31% yield) over two steps as a pale yellow oil. The free base was converted to the corresponding oxalate salt. Mp 167-172° C.; $^1$H NMR (400 MHz, $CDCl_3$) δ 7.36 (dd, J=8.3, 5.4 Hz, 4H), 7.01 (t, J=8.4 Hz, 4H), 5.15 (s, 1H), 4.43 (d, J=13.3 Hz, 1H), 4.14 (d, J=13.7 Hz, 1H), 3.15 (t, J=12.8 Hz, 1H), 2.78 (t, J=6.5 Hz, 3H), 2.65 (tt, J=10.2, 4.2 Hz, 1H), 2.56 (t, J=6.5 Hz, 2H), 1.84 (d, J=18.0 Hz, 3H), 1.74 (tt, J=8.3, 4.8 Hz, 1H), 1.50 (s, 1H), 1.38-1.14 (m, 1H), 0.95 (dd, J=5.3, 2.3 Hz, 2H), 0.74 (dq, J=7.1, 4.0 Hz, 2H); $^{13}$C NMR (100 MHz, $CDCl_3$) δ 171.74, 163.12, 160.67, 136.92, 136.89, 129.76, 129.68, 115.61, 115.39, 77.33, 77.22, 77.02, 76.70, 54.50, 52.67, 45.13, 44.08, 40.89, 33.21, 33.00, 32.18, 10.99, 7.17; FT-IR (ATR, υ, $cm^{-1}$) 2922, 2853, 1630, 1504, 1437, 1220, 1156, 1129, 1014, 825, 572; Anal. ($C_{24}H_{28}F_2N_2OS \cdot C_2H_2O_4 \cdot 0.25H_2O$) C, H, N. The c Log P of JBG02-083 is 3.19.

Additional aminopiperidine and piperidineamino analogue compounds are provided in Table 1.

Example 2. Synthesis of Substituted Piperazine Analogues

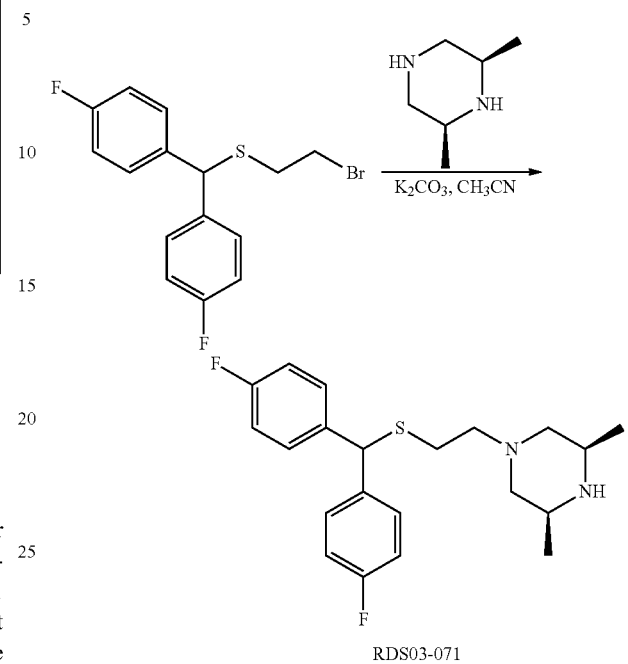

RDS03-071

Synthesis of (3S,5R)-1-(2-((Bis(4-fluorophenyl)methyl)thio)ethyl)-3,5-dimethylpiperazine (RDS03-071)

To an oven-dried 100 mL round bottom flask containing a solution of (bis(4-fluorophenyl)methyl)(2-bromoethyl)sulfane (750 mg, 2.19 mmol) in acetonitrile (43.8 mL) was added commercially available cis-2,6-dimethylpiperazine (1.00 g, 8.75 mmol) and K2CO3 (1.21 g, 8.76 mmol). The reaction was refluxed overnight until starting material was consumed, upon which time it was concentrated under reduced pressure, resuspended in CH2Cl2 (30 mL) and partitioned with water (20 mL). The aqueous layer was extracted with CH2Cl2 (3×8 mL), and the combined organics were dried with Na2SO4 and concentrated in vacuo. The crude oil was purified by flash column chromatography (0-15% of a solution of 10% $NH_4OHMeOH$ in CH2Cl2) to afford RDS3-071 (666 mg, 1.77 mmol) as a pale yellow oil in 81% yield.

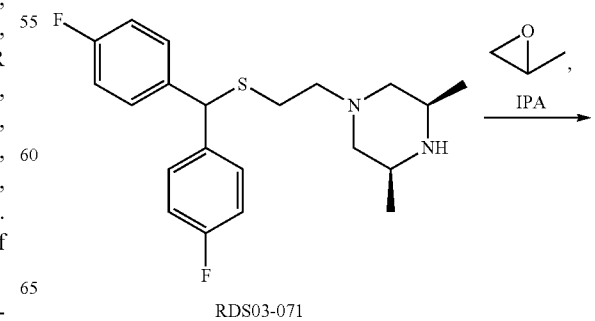

RDS03-071

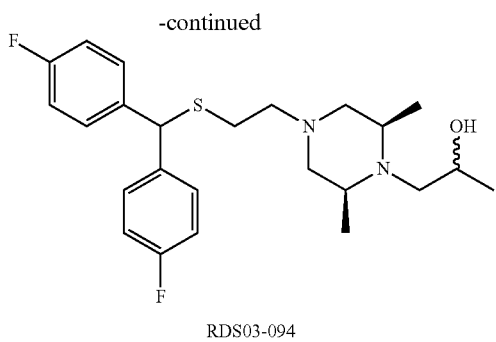

RDS03-094

Synthesis of 1-((2S,6R)-4-(2-((Bis(4-fluorophenyl)methyl)thio)ethyl)-2,6-dimethylpiperazin-1-yl)propan-2-ol (RDS03-094)

To an oven-dried 10 mL round bottom flask was added RDS3-071 (200 mg, 0.53 mmol) and dissolved in iPrOH (5.3 mL). Commercially available propylene oxide (372 µL, 5.31 mmol) was added via syringe. The reaction was closed tightly inside of a sealed tube and heated to 80° C. overnight after which time it was cooled to room temperature and concentrate under reduced pressure. The crude oil was purified via flash column chromatography (0-15% of a solution of 10% $NH_4OH$/MeOH in $CH_2Cl_2$) to afford RDS03-094 (78% yield, 179 mg, 0.41 mmol) as a colorless oil. The free base was converted into the oxalate salt in hot isopropanol and recrystallized from MeOH to yield a colorless solid. FTIR (ATR, $cm^{-1}$) ν 3010, 2970, 1737, 1630, 1506, 1217, 1158, 1013, 730, 529. MP=148.2-149.4° C. $^1H$ NMR (400 MHz $CDCl_3$) δ 7.39-7.28 (m, 4H), 7.03-6.87 (m, 4H), 5.18 (s, 1H), 3.63 (dq, J=7.6, 6.1 Hz, 1H), 2.57 (m, 4H), 2.50-2.33 (m, 6H), 1.85-1.65 (m, 2H), 1.07 (d, J=6.1 Hz, 3H), 0.99 (dd, J=6.2, 2.6 Hz, 6H). $^{13}C$ NMR (100 MHz, $CDCl_3$) δ 163.04, 160.60, 137.01, 136.98, 129.81, 129.73, 115.53, 115.32, 65.40, 60.82, 58.47, 58.29, 57.56, 56.17, 52.83, 29.24, 20.40, 19.33, 19.10. Anal. ($C_{29}H_{38}F_2N_2O_{11}S$-½$H_2O$) C, H, N. The c Log P of RDS03-094 is 4.46.

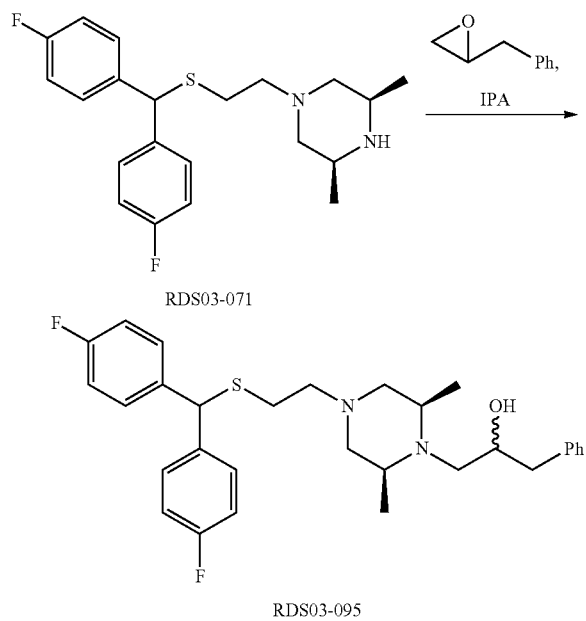

RDS03-071

RDS03-095

Synthesis of 1-((2S,6R)-4-(2-((bis(4-fluorophenyl)methyl)thio)ethyl)-2,6-dimethylpiperazin-1-yl)-3-phenylpropan-2-ol (RDS03-095)

To an oven-dried 10 mL round bottom flask was added RDS3-071 (200 mg, 0.53 mmol) and dissolved in iPrOH (5.3 mL). Commercially available (2,3-epoxypropyl)benzene (1.95 mL, 5.31 mmol) was added via syringe. The reaction was fitted with a condenser and refluxed overnight after which time it was cooled to room temperature and concentrate under reduced pressure. The crude oil was purified via flash column chromatography (0-15% of a solution of 10% $NH_4OH$/MeOH in $CH_2Cl_2$) to afford RDS3-095 (45% yield, 124 mg, 0.24 mmol) as a colorless oil. The free base was converted into the oxalate salt in hot isopropanol and recrystallized from MeOH to yield a colorless solid. FTIR (ATR, $cm^{-1}$) ν 2935, 2860, 1628, 1602, 1506, 1223, 1158, 1013, 837, 705, 574. MP 150.2-151.8° C. $^1H$ NMR (400 MHz, $CDCl_3$) δ 7.35 (dd, J=8.4, 5.4 Hz, 4H), 7.25 (m, 5H), 6.99 (t, J=8.5 Hz, 4H), 5.20 (s, 1H), 3.78 (dq, J=10.5, 5.5 Hz, 1H), 3.54 (bs, 1H), 2.80 (dd, J=13.7, 6.9 Hz, 2H), 2.76-2.53 (m, 6H), 2.51-2.35 (m, 5H), 1.74 (td, J=10.4, 7.6 Hz, 2H), 0.98 (dd, J=6.2, 3.0 Hz, 6H). $^{13}C$ NMR (100 MHz, $CDCl_3$) δ 163.09, 160.64, 138.37, 137.00, 136.97, 129.82, 129.74, 129.30, 128.33, 126.23, 115.56, 115.35, 70.04, 60.92, 60.87, 58.21, 57.58, 56.18, 52.88, 41.87, 29.27, 19.23, 19.00. Anal. ($C_{35}H_{42}F_2N_2O_{11}S$-½$H_2O$) C, H, N. The c Log P of RDS03-095 is 5.89.

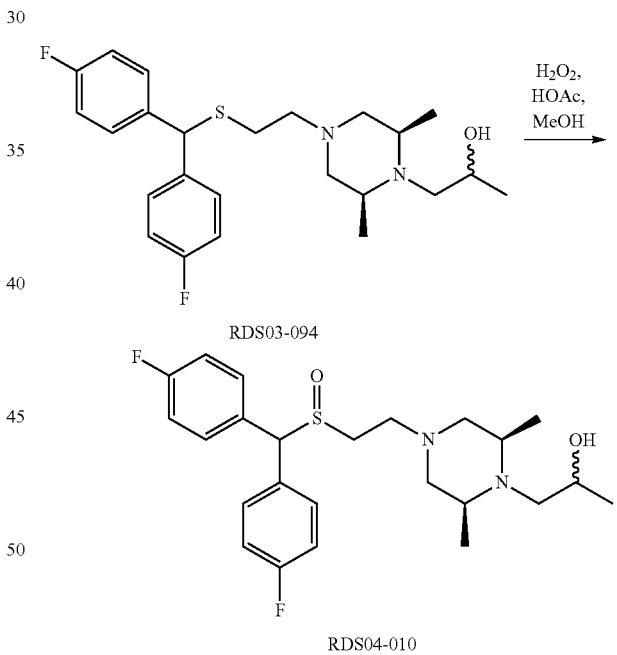

RDS03-094

RDS04-010

Synthesis of 1-((2S,6R)-4-(2-((Bis(4-fluorophenyl)methyl)sulfinyl)ethyl)-2,6-dimethylpiperazin-1-yl)propan-2-ol (RDS04-010)

To a 25 mL round bottom flask containing RDS03-094 (47.1 mg, 0.10 mmol) was added a solution of acetic acid:MeOH (1:3, c=0.25, 0.4 mL). $H_2O_2$ (33% in water, 10.6 µL, 0.10 mmol) was added via syringe at room temperature. The reaction was allowed to stir for 48 hr at room temperature before being quenched with water (5 mL) and extracted with $CH_2Cl_2$ (3×3 mL). The combined organics were dried with MgSO₄ and concentrated under reduced pressure. The resulting crude oil was purified by flash chromatography (0-15% of a solution of 10% NH₄OH/MeOH in CH₂Cl₂) to afford RDS04-010 as a colorless oil (82% yield, 36.9 mg, 0.082 mmol). The free base was converted into the oxalate salt in hot isopropanol and recrystallized from MeOH to yield an amorphous solid. FTIR (ATR, cm⁻¹) v 2984, 2502, 1709, 1623, 1602, 1507, 1223, 1013, 836, 699. ¹H NMR (400 MHz, CDCl₃) δ 7.53 (dddd, J=11.7, 9.1, 6.1, 3.3 Hz, 4H), 7.20 (dddd, J=13.8, 10.9, 7.0, 4.0 Hz, 4H), 5.44-5.36 (m, 1H), 5.12-5.04 (m, 1H), 3.80 (p, J=6.5 Hz, 1H), 3.58 (s, 1H), 3.18-2.63 (m, 8H), 2.57 (d, J=6.0 Hz, 2H), 2.00 (dd, J=24.7, 13.0 Hz, 2H), 1.32-1.03 (m, 9H). ¹³C NMR (100 MHz, CDCl₃) δ 163.91, 163.67, 161.45, 161.20, 131.82, 131.78, 131.02, 130.94, 130.59, 130.55, 130.34, 130.26, 116.34, 116.13, 115.76, 115.54, 69.55, 65.28, 60.91, 60.21, 58.25, 58.20, 56.12, 56.10, 53.45, 50.49, 50.48, 48.17, 48.14, 20.43, 20.40, 19.12, 19.04, 18.94, 18.85. (C₂₈H₃₆F₂N₂O₁₀S—H₂O) C, H, N. The c Log P of RDS4-010 is 2.53.

CDCl₃) δ 7.36 (dd, J=8.5, 5.1 Hz, 3H), 7.31-7.24 (m, 1H), 7.21 (d, J=7.1 Hz, 3H), 6.99 (t, J=8.4 Hz, 4H), 5.16 (s, 1H), 3.87 (p, J=6.4 Hz, 1H), 2.93-2.35 (m, 7H), 2.27-2.14 (m, 2H), 2.03 (t, J=10.9 Hz, 1H), 1.70 (t, J=10.5 Hz, 1H), 1.26 (s, 1H), 0.88 (t, J=5.5 Hz, 5H). ¹³C NMR (100 MHz, CDCl₃) δ 163.14, 138.17, 138.14, 136.75, 129.79, 129.77, 129.71, 129.69, 129.29, 129.26, 128.33, 128.30, 126.30, 115.64, 115.61, 115.42, 115.39, 67.13, 67.10, 63.12, 63.09, 62.56, 62.53, 59.35, 59.33, 54.21, 54.03, 54.01, 52.59, 52.57, 48.06, 41.34, 41.31, 27.23, 17.90, 17.87, 17.78, 17.75. Anal. (C₃₄H₄₀F₂N₂O₁₀S-2H₂O) C, H, N. The c Log P of RDS4-011 is 3.97.

Additional Substituted Piperazine analogue compounds are provided in Table 1.

Example 3. Synthesis of Spirobicyclodiaza Analogues

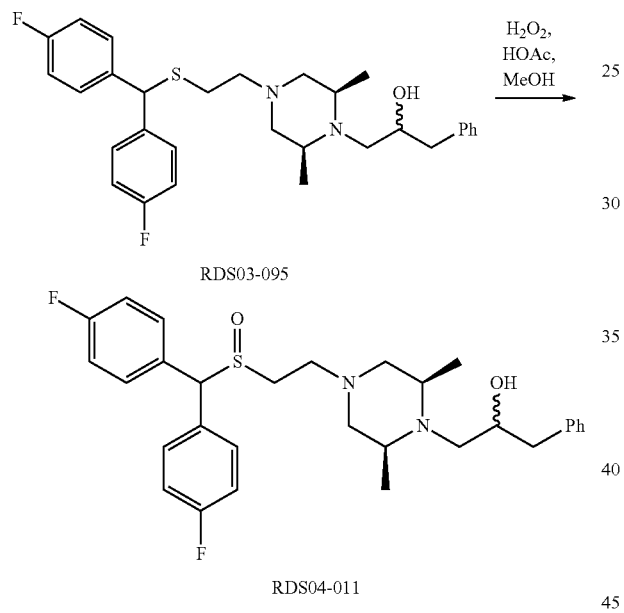

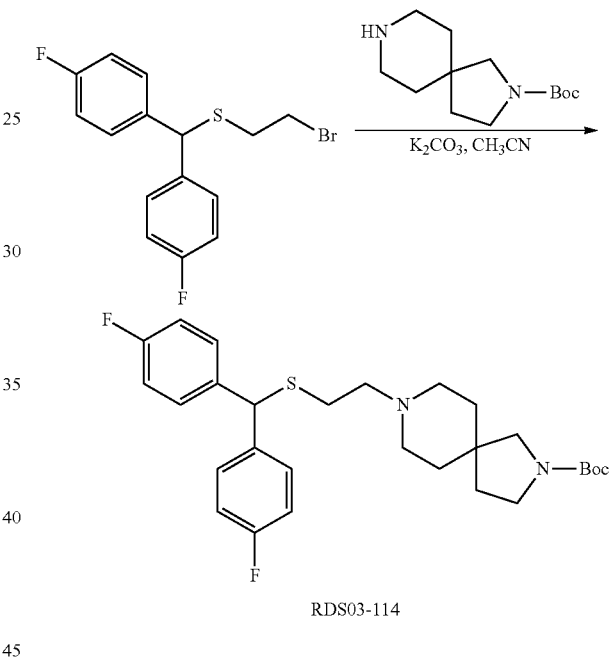

Synthesis of 1-((2S,6R)-4-(2-((Bis(4-fluorophenyl)methyl)sulfinyl)ethyl)-2,6-dimethylpiperazin-1-yl)-3-phenylpropan-2-ol (RDS04-011)

To a 25 mL round bottom flask containing RDS03-095 (34.3 mg, 0.067 mmol) was added a solution of acetic acid:MeOH (1:3, c=0.25, 0.4 mL). H₂O₂ (33% in water, 6.9 µL, 0.067 mmol) was added via syringe at room temperature. The reaction was allowed to stir for 48 hrs at room temperature before being quenched with water (5 mL) and extracted with CH₂Cl₂ (3×3 mL). The combined organics were dried with MgSO₄ and concentrated under reduced pressure. The resulting crude oil was purified by flash chromatography (0-15% of a solution of 10% NH₄OH/MeOH in CH₂Cl₂) to afford RDS04-011 as a colorless oil (94% yield, 33.17 mg, 0.063 mmol). The free base was converted into the oxalate salt in hot isopropanol and recrystallized from MeOH to yield an amorphous solid. FTIR (ATR, cm⁻¹) v 3007, 2926, 1627, 1603, 1507, 1414, 1223, 1160, 1104, 838, 703, 532. ¹H NMR (400 MHz, Synthesis of tert-Butyl 8-(2-((bis(4-fluorophenyl)methyl)thio)ethyl)-28-diazaspiro[4.5]decane-2-carboxylate (RDS03-114)

To an oven-dried 100 mL round bottom flask containing a solution of (bis(4-fluorophenyl)methyl)(2-bromoethyl)sulfane (428 mg, 1.25 mmol) in acetonitrile (6.25 mL) was added commercially available tert-butyl 2,8-diazaspiro[4.5]decane-2-carboxylate (300 mg, 1.25 mmol) and K₂CO₃ (2.59 g, 1.88 mmol). The reaction was refluxed overnight until starting material was consumed, upon which time it was concentrated under reduced pressure, resuspended in CH₂Cl₂ (10 mL) and partitioned with water (8 mL). The aqueous layer was extracted with CH₂Cl₂ (3×5 mL), and the combined organics were dried with Na₂SO₄ and concentrated in vacuo. The crude oil was purified by flash column chromatography (0-15% of a solution of 10% NH₄OH/MeOH in CH₂Cl₂) to afford RDS03-114 (577 mg, 1.15 mmol) as a pale yellow oil in 89% yield. ¹H NMR (400 MHz, CDCl₃) δ 7.41-7.32 (m, 4H), 7.04-6.92 (m, 4H), 5.22 (s, 1H), 3.35 (dt, J=20.6, 7.0 Hz, 2H), 3.13 (d, J=30.3 Hz, 2H), 2.51 (p, J=3.4 Hz, 4H), 2.46-2.32 (m, 3H), 2.23 (ddd, J=22.2, 13.1, 6.4 Hz, 2H), 1.63 (q, J=6.3, 5.7 Hz, 3H), 1.59-1.49 (m, 4H), 1.46 (s, 9H). $^{13}$C NMR (100 MHz, CDCl$_3$) δ 162.91, 160.47, 154.52, 137.07, 137.03, 129.77, 129.75, 129.69, 129.67, 115.50, 115.45, 115.41, 115.29, 115.20, 78.87, 58.00, 52.69, 50.78, 50.73, 44.08, 43.83, 40.26, 39.37, 34.60, 29.56, 29.45, 28.45.

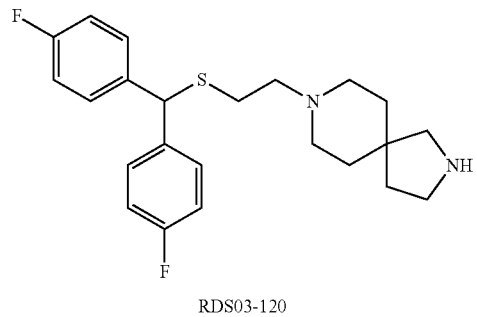

RDS03-114

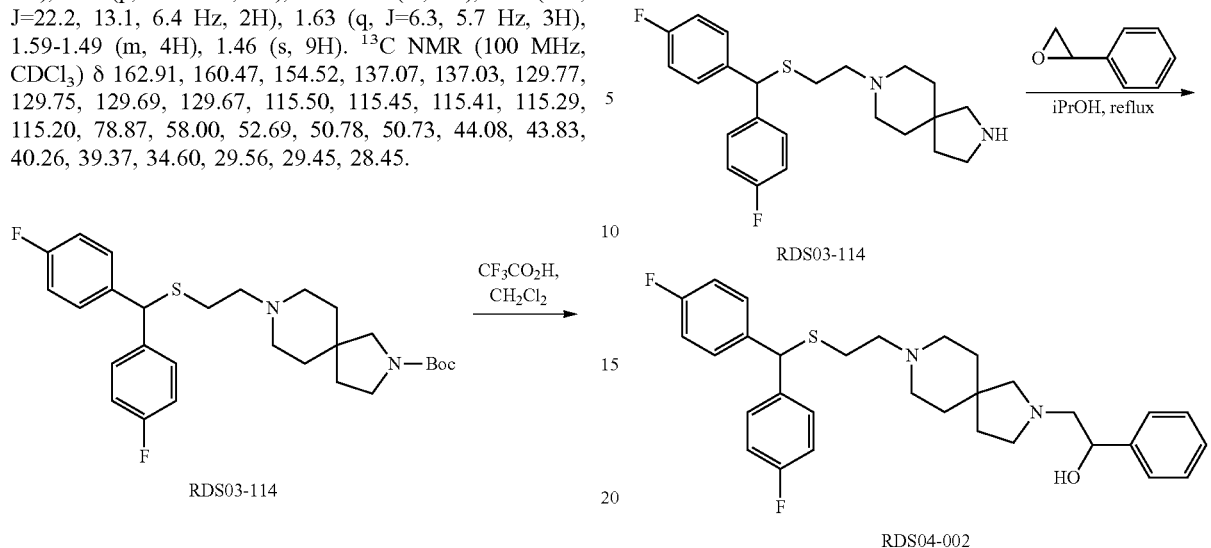

RDS03-120

Synthesis of 8-(2-((Bis(4-fluorophenyl)methyl)thio)ethyl)-2,8-diazaspiro[4.5]decane (RDS03-120)

To a solution of RDS03014 (800 mg, 1.59 mmol) in CH$_2$Cl$_2$ (7 mL) was added trifluoroacetic acid (1.5 mL) at room temperature. The reaction was allowed to stir for 5 hrs until TLC indicated consumption of starting material. The reaction was diluted with CH$_2$Cl$_2$ (8 mL) and partitioned with 15% NH$_4$OH (aq, 10 mL). The aqueous layer was extracted with CH$_2$Cl$_2$ (3×5 mL), dried with Na$_2$SO$_4$, and concentrated in vacuo. The resulting crude oil was purified by flash column chromatography (0-15% of a solution of 10% NH$_4$OH/MeOH in CH$_2$Cl$_2$) to afford RDS03-120 (92% yield, 589 mg, 1.46 mmol) as a pale yellow oil. $^1$H NMR (400 MHz, CDCl$_3$) δ 7.36 (ddd, J=8.7, 5.3, 1.5 Hz, 5H), 6.98 (tt, J=8.6, 2.2 Hz, 5H), 5.21 (s, 1H), 3.61-3.20 (m, 4H), 2.91 (td, J=7.0, 1.3 Hz, 3H), 2.65 (d, J=1.3 Hz, 3H), 2.51 (d, J=1.3 Hz, 5H), 2.43-2.13 (m, 5H), 1.67-1.38 (m, 8H). $^{13}$C NMR (100 MHz, CDCl$_3$) δ 162.64, 162.59, 160.19, 160.14, 136.67, 129.47, 129.40, 129.34, 129.32, 115.16, 115.13, 115.10, 115.08, 114.95, 114.92, 114.89, 114.87, 57.78, 57.74, 57.71, 52.43, 52.38, 50.98, 50.95, 50.91, 45.51, 45.47, 40.73, 40.69, 40.66, 37.50, 35.77, 35.73, 35.69, 29.13, 29.08, 29.05.

Synthesis of 2-(8-(2-Bis(4-fluorophenyl)methyl)thio)ethyl-2,8-diazaspiro[4.5]decan-2-yl)-1-phenylethan-1-ol (RDS04-002)

To a 25 mL round bottom flask was added RDS3-120 (300 mg, 0.75 mmol) and commercially available styrene oxide (5.22 mL, 75.6 mmol) and isopropanol (2.28 mL). The solution was heated to reflux overnight, upon which time TLC analysis indicated consumption of starting material. The reaction was concentrated in vacuo, and the crude oil was purified via flash column chromatography (0-15% of a solution of 10% NH$_4$OH/MeOH in CH$_2$C$_2$) to afford RDS4-002 (38% yield, 149.0, 0.29 mmol) as a pale yellow oil. The free base was converted into the oxalate salt in hot isopropanol and recrystallized from MeOH to yield a colorless solid. $^1$H NMR (400 MHz, CDCl$_3$) δ 7.43-7.32 (m, 4H), 7.32-7.16 (m, 5H), 7.05-6.92 (m, 4H), 5.20 (s, 1H), 3.89 (dddd, J=10.2, 6.9, 5.6, 3.2 Hz, 1H), 2.82 (dd, J=13.6, 7.0 Hz, 1H), 2.70 (ddt, J=13.6, 10.9, 6.3 Hz, 2H), 2.64-2.41 (m, 7H), 2.41-2.16 (m, 6H), 1.56 (dt, J=12.3, 6.6 Hz, 6H). $^{13}$C NMR (100 MHz, CDCl$_3$) δ 163.07, 160.62, 138.34, 137.10, 137.07, 129.86, 129.84, 129.76, 129.37, 128.33, 126.27, 115.65, 115.56, 115.44, 115.35, 68.91, 61.32, 58.22, 53.35, 52.87, 51.18, 51.16, 41.53, 39.87, 37.63, 37.49, 29.60. FTIR 2924, 2852, 1711, 1602, 1505, 1221, 1157, 1097, 702, 530. Anal. (C$_{35}$H$_{40}$F$_2$N$_2$O$_9$S-½H$_2$O) CH, N. The c Log P of RDS04-002 is 6.12.

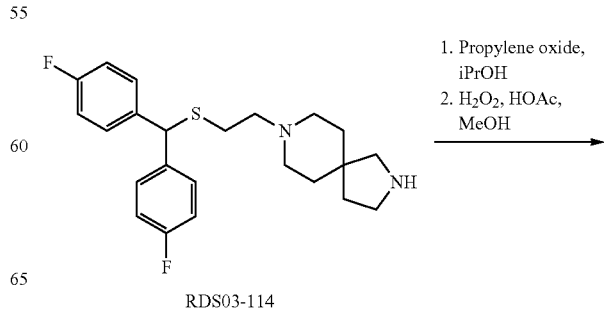

RDS03-114

-continued

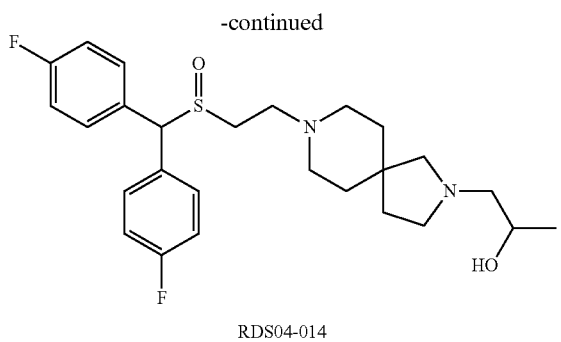

RDS04-014

Synthesis of (RDS04-014)

To a 10 mL round bottom flask was added RDS03-114 (97 mg, 0.24 mmol) and dissolved in iPrOH (2 mL) and propylene oxide (2 mL). The reaction was allowed to stir at reflux for 48 hrs before it was concentrated under reduced pressure. The crude oil was dissolved in $Et_2O$ (3 mL) and partitioned with 1N HCl (4 mL). The aqueous layer was basified with $NH_4OH$ to pH=9 and extracted with $CH_2Cl_2$ (3×3 mL). The combined organics were dried with $MgSO_4$ and concentrated in vacuo. The resulting oil was redissolved in a solution of acetic acid:MeOH (1:3, c=0.25, 1.0 mL) within a 2 dram vial equipped with a stir bar. $H_2O_2$ (33% in water, 24.4 μL, 0.24 mmol) was added via syringe at room temperature. The reaction was allowed to stir for 48 hrs at room temperature before being quenched with water (5 mL) and extracted with $CH_2Cl_2$ (3×3 mL). The combined organics were dried with $MgSO_4$ and concentrated under reduced pressure. The resulting crude oil was purified by flash chromatography (0-15% of a solution of 10% $NH_4OH$/MeOH in $CH_2Cl_2$) to afford RDS4-014 as a colorless oil (21% yield over 2 steps, 24.0 mg, 0.05 mmol). The free base was converted into the oxalate salt in hot isopropanol and recrystallized from MeOH to yield a colorless solid. FTIR (ATR, $cm^{-1}$) ν 3053, 2884, 1664, 1506, 1292, 1157, 1003, 832, 697. MP 166.0-166.8° C. $^1H$ NMR (400 MHz, $CDCl_3$) δ 7.50-7.32 (m, 4H), 7.32-7.14 (m, 6H), 7.05-6.83 (m, 4H), 5.16 (s, 1H), 2.97-2.74 (m, 4H), 2.74-2.64 (m, 2H), 2.54 (d, J=2.9 Hz, 1H), 2.45-2.38 (m, 2H), 2.27-2.19 (m, 2H), 2.09-1.96 (m, 1H), 1.70 (dd, J=11.1, 10.1 Hz, 1H), 1.01 (ddd, J=10.8, 6.4, 5.4 Hz, 1H), 0.89 (dd, J=6.2, 5.0 Hz, 6H). $^{13}C$ NMR (100 MHz, $CDCl_3$) δ 164.01, 163.85, 161.54, 161.38, 139.41, 130.97, 130.89, 130.86, 130.56, 130.48, 130.09, 130.06, 123.25, 116.36, 116.14, 115.76, 115.69, 115.55, 77.32, 77.00, 76.68, 72.81, 29.67, 23.22. Anal. ($C_{29}H_{38}F_2N_2O_{10}S$) C, H, N. The c Log P of RDS04-014 is 2.93.

Example 4. Animal Tissue Radioligand Binding Protocols

Binding affinities of the analogue compounds were evaluated at the DAT and SERT in rat brain membranes, and sigma-1 in guinea pig brain membranes according to the following protocols.

$\sigma_1R$ Radioligand Binding in Guinea Pig Cortex

Male Hartley guinea pig cortices were dissected from freshly harvested brains (shipped cold in PBS buffer from BioReclamation IVT (Hicksville, N.Y.)) and frozen at −80° C. for future use. On test day, thawed guinea pig cortices were suspended and homogenized in 10 ml of cold binding buffer (10 mM Tris.HCl, 0.32M Sucrose, pH 7.4 at 25° C.) with a glass-teflon apparatus and centrifuged (~1,200 rpm) for 10 min at 4° C. The supernatant was collected in a clean tube and the pellet re-suspended in 10 ml of cold buffer and centrifuged again (~1,200 rpm) for 10 min at 4° C. The supernatants were pooled together and centrifuged (20,000 rpm) for 15 min at 4° C. The final pellet was suspended in ice-cold binding buffer at 50 mg/ml concentration. A Bradford protein assay (Bio-Rad, Hercules, Calif.) was used to determine the protein concentration present in the tissue preparation (1.25 mg/ml). All test compounds were freshly dissolved in 30% DMSO and 70% $H_2O$ to a stock concentration of 1 mM or 100 μM. When necessary, to assist the solubilization of compounds, 10 μl of glacial acetic acid was added along with the DMSO (in place of 10 μl final $H_2O$ volume). Each test compound was then diluted into 10 half-log serial dilutions using 30% DMSO as the vehicle. Radioligand competition experiments were conducted in 96-well plates containing 300 μl fresh binding buffer, 50 μl of diluted test compound, 100 μl of tissue preparation (125 μg/well total protein amount), and 50 μl of radioligand diluted in binding buffer ($[^3H]$-(+)-Pentazocine: 3 nM final concentration, ARC, Saint Louis, Mo.). Nonspecific binding was determined using either 10 μM PRE084 or 10 μM (+)-Pentazocine and total binding was determined with 30% DMSO vehicle (3% DMSO final concentration). All compound dilutions were tested in triplicate and the competition reactions started with the addition of the tissue preparation and incubated for 120 min at room temperature. The reaction was terminated by filtration through Perkin Elmer UniFilter-96 GF/B, presoaked for 120 min in 0.05% polyethylenimine, using a Brandel 96-Well Plates Harvester Manifold (Brandel Instruments, Gaithersburg, Md.). The filters were washed 3 times with 3 ml (3×1 ml/well) of ice cold binding buffer. 65 μL Perkin Elmer MicroScint20 Scintillation Cocktail was added to each well and filters were counted using a Perkin Elmer MicroBeta Microplate Counter (calculated efficiency: 30.9%). $IC_{50}$ values for each compound were determined from dose-response curves and $K_i$ values were calculated using the Cheng-Prusoff equation; $K_d$ value for $[^3H]$-(+)-Pentazocine (5.18±0.751 nM) was determined via separate homologous competitive binding experiments. $K_i$ values were determined from at least 3 independent experiments and are reported as mean±SEM.

SERT Radioligand Binding in Rat Midbrain

Frozen brain stems dissected from male Sprague-Dawley rat brains (supplied in ice cold PBS buffer from Bioreclamation IVT (Hicksville, N.Y.)) were homogenized in 10-20 volumes (w/v) of 50 mM ice cold Tris buffer (120 mM NaCl and 5 mM KCl, adjusted to pH 7.4 at 25° C.) using a Brinkman Polytron (two cycles at setting 6 for 10 s each). The tissue was centrifuged at 20,000 rpm for 10 min at 4° C. The pellet was suspended in cold buffer and centrifuged again using the same settings. The resulting pellet was resuspended in cold buffer at a concentration of 20 mg/mL OWW (original wet weight). On test day, all test compounds were freshly dissolved in 30% DMSO and 70% $H_2O$ to a stock concentration of 1 mM or 100 μM. When necessary, to assist the solubilization of compounds, 10 μl of glacial acetic acid was added along with the DMSO (in place of 10 μl final $H_2O$ volume). Each test compound was then diluted into 10 half-log serial dilutions using 30% DMSO vehicle. Radioligand competition experiments were conducted in 96-well plates containing 50 μL of diluted test compound, 300 μl of fresh binding buffer, 50 μl of radioligand diluted in binding buffer ($[^3H]$-Citalopram HCl: 1.5 nM final concentration; ARC, Saint Louis, Mo.) and 100 μl of tissue preparation (2 mg of brain stem membranes per well). Non-specific binding was determined using 10 μL Fluoxetine HCl and total binding was determined with 30% DMSO vehicle. The reaction was started with the addition of the tissue. All compound dilutions were tested in triplicate and the reaction incubated for 60 min at room temperature. The reaction was terminated by filtration through Perkin Elmer Uni-Filter-96 GF/B, presoaked for 60 min in 0.3% polyethylenimine, using a Brandel 96-Well Plates Harvester Manifold (Brandel Instruments, Gaithersburg, Md.). The filters were washed 3 times with 3 mL (3×1 mL/well) of ice cold binding buffer. 65 μL Perkin Elmer MicroScint20 Scintillation Cocktail was added to each well and filters were counted using a Perkin Elmer MicroBeta Microplate Counter (calculated efficiency: 31.1%). $IC_{50}$ values for each compound were determined from dose-response curves and $K_i$ values were calculated using the Cheng-Prusoff equation; $K_d$ value for [$^3$H]-Citalopram HCl (6.68±1.05 nM) was determined via separate homologous competitive binding experiments. These analyses were performed using GraphPad Prism version 6.00 for Macintosh (GraphPad Software, San Diego, Calif.). $K_i$ values were determined from at least 3 independent experiments and are reported as mean±SEM.

DAT Radioligand Binding in Rat Striatum

Frozen brain striata dissected from male Sprague-Dawley rat brains (supplied in ice cold PBS buffer from Bioreclamation IVT (Hicksville, N.Y.)) were homogenized in 10-20 volumes (w/v) of modified sucrose phosphate buffer (0.32M Sucrose, 7.74 mM $Na_2HPO_4$, 2.26 mM $NaH_2PO_4$ adjusted to pH 7.4 at 25° C.) using a Brinkman Polytron (two cycles at setting 6 for 10 s each). The tissue was centrifuged at 20,000 rpm for 10 min at 4° C. The pellet was suspended in cold buffer and centrifuged again using the same settings. The resulting pellet was resuspended in cold buffer at a concentration of 15 mg/mL OWW (original wet weight). On test day, all test compounds were freshly dissolved in 30% DMSO and 70% $H_2O$ to a stock concentration of 1 mM or 100 μM When necessary, to assist the solubilization of compounds, 10 μl of glacial acetic acid was added along with the DMSO (in place of 10 μl final $H_2O$ volume). Each test compound was then diluted into 10 half-log serial dilutions using 30% DMSO vehicle. Radioligand competition experiments were conducted in 96-well plates containing 50 μL of diluted test compound, 300 μl of fresh binding buffer, 50 μl of radioligand diluted in binding buffer ([$^3$H]-WIN35,428: 1.5 nM final concentration; ARC, Saint Louis, Mo.) and 100 μl of tissue preparation (1.5 mg of brain striatum membranes per well). Non-specific binding was determined using 10 μL Indatraline and total binding was determined with 30% DMSO vehicle. The reaction was started with the addition of the tissue. All compound dilutions were tested in triplicate and the reaction incubated for 120 min at 4° C. The reaction was terminated by filtration through Perkin Elmer Uni-Filter-96 GF/B, presoaked for 120 min in 0.05% polyethylenimine, using a Brandel 96-Well Plates Harvester Manifold (Brandel Instruments, Gaithersburg, Md.). The filters were washed 3 times with 3 mL (3×1 mL/well) of ice cold binding buffer. 65 μL Perkin Elmer MicroScint20 Scintillation Cocktail was added to each well and filters were counted using a Perkin Elmer MicroBeta Microplate Counter (calculated efficiency: 34.7%). $IC_{50}$ values for each compound were determined from dose-response curves and $K_i$ values were calculated using the Cheng-Prusoff equation; $K_d$ value for [$^3$H]-WIN35,428 (28.1±1.07 nM) was determined via separate homologous competitive binding experiments. These analyses were performed using GraphPad Prism version 6.00 for Macintosh (GraphPad Software, San Diego, Calif.). $K_i$ values were determined from at least 3 independent experiments and are reported as mean±SEM.

The results of the assays are provided in Table 2.

TABLE 1

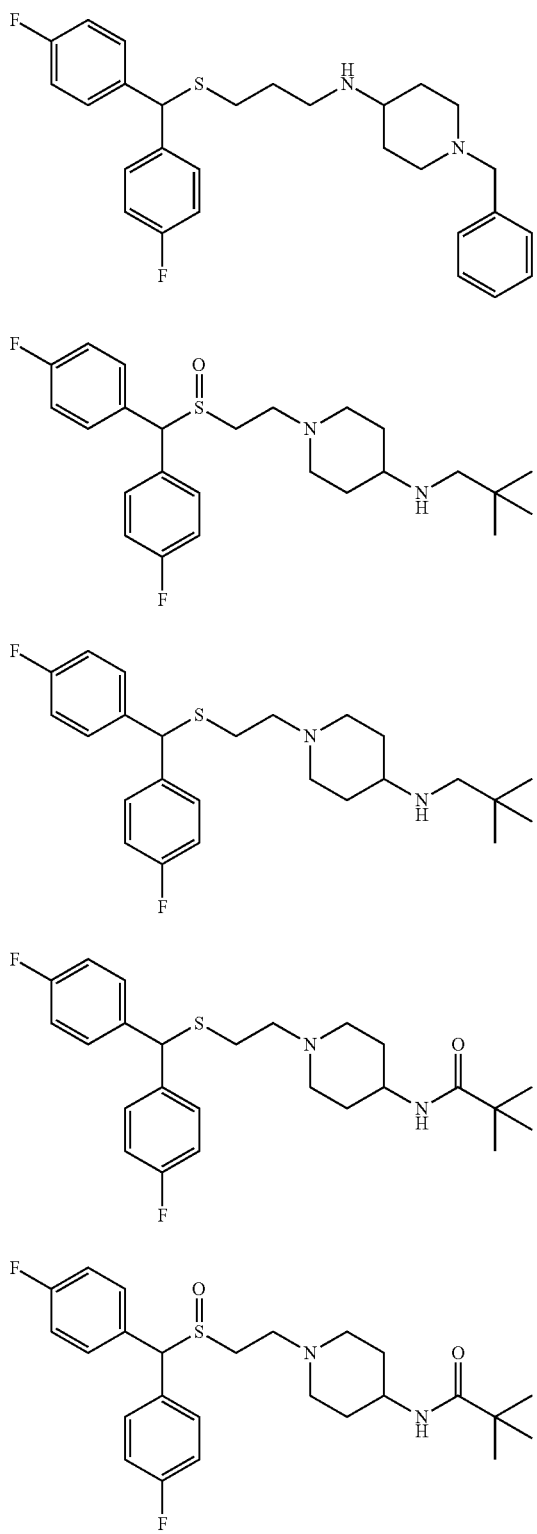

TABLE 1-continued
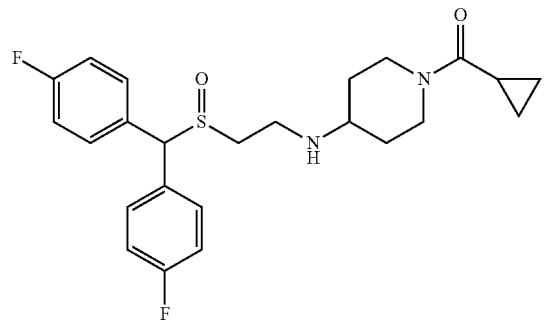 [SMILES: O=C(C1CC1)N1CCC(NCCS(=O)C(c2ccc(F)cc2)c2ccc(F)cc2)CC1]
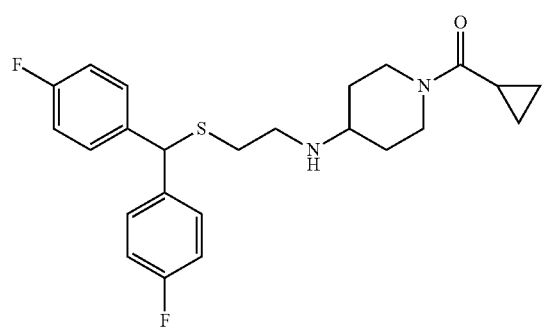 [SMILES: O=C(C1CC1)N1CCC(NCCSC(c2ccc(F)cc2)c2ccc(F)cc2)CC1]
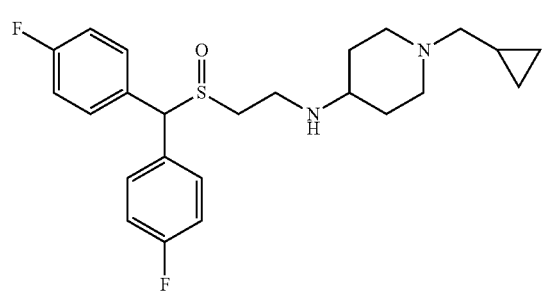 [SMILES: O=S(CCNC1CCN(CC2CC2)CC1)C(c1ccc(F)cc1)c1ccc(F)cc1]
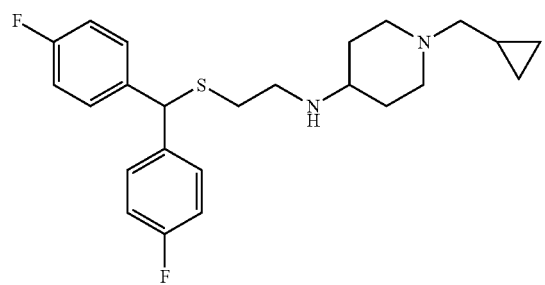 [SMILES: Fc1ccc(C(SCCNC2CCN(CC3CC3)CC2)c2ccc(F)cc2)cc1]
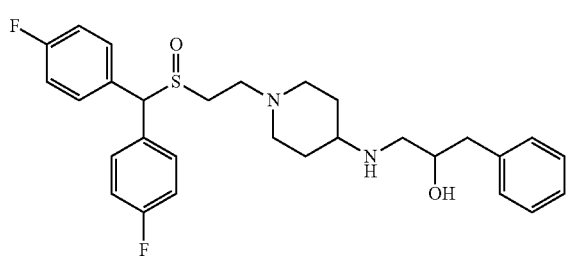 [SMILES: O=S(CCN1CCC(NCC(O)Cc2ccccc2)CC1)C(c1ccc(F)cc1)c1ccc(F)cc1]
TABLE 1-continued
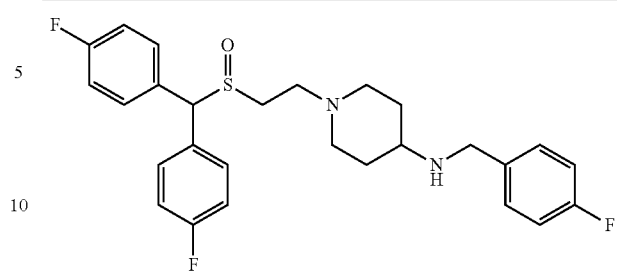
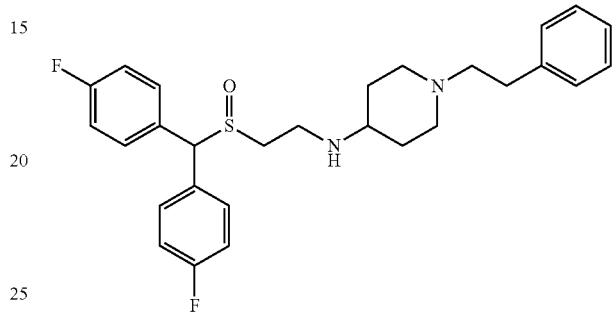
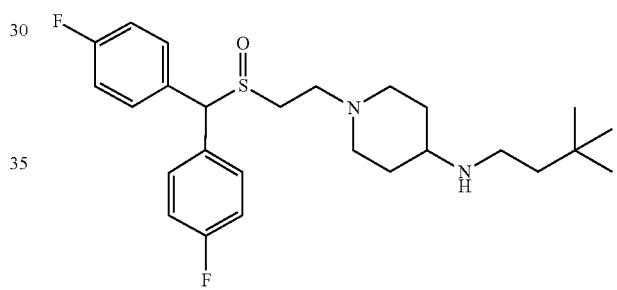
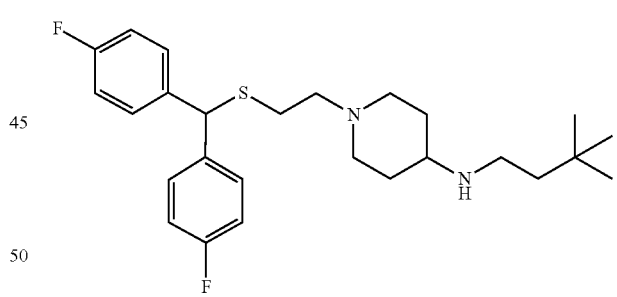
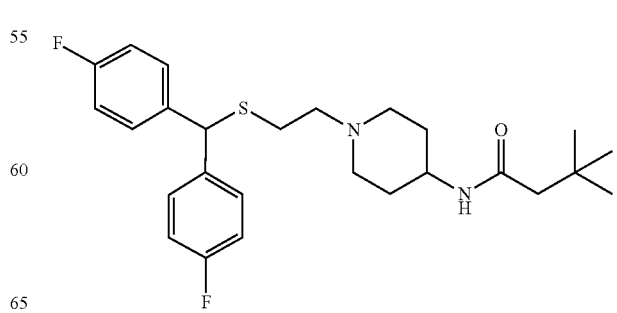

TABLE 1-continued
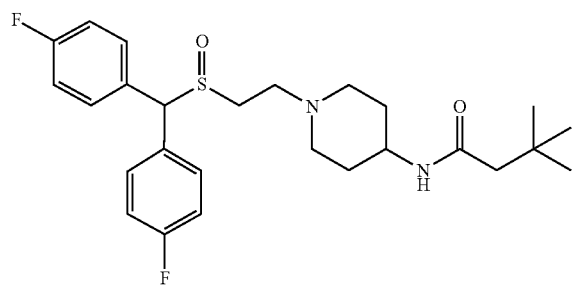 [SMILES: CC(C)(C)CC(=O)NC1CCN(CCS(=O)C(c2ccc(F)cc2)c2ccc(F)cc2)CC1]
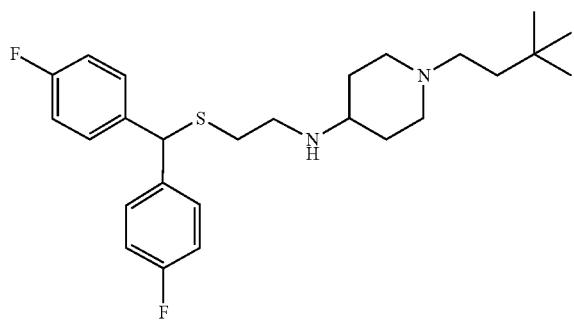 [SMILES: CC(C)(C)CCN1CCC(NCCSC(c2ccc(F)cc2)c2ccc(F)cc2)CC1]
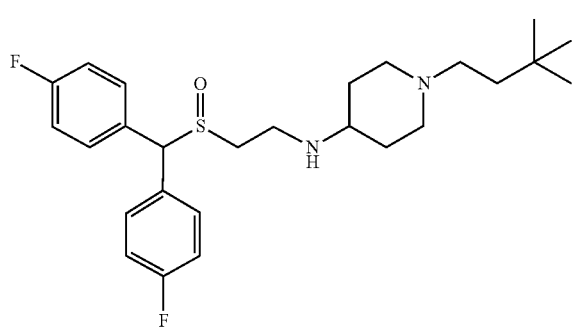 [SMILES: CC(C)(C)CCN1CCC(NCCS(=O)C(c2ccc(F)cc2)c2ccc(F)cc2)CC1]
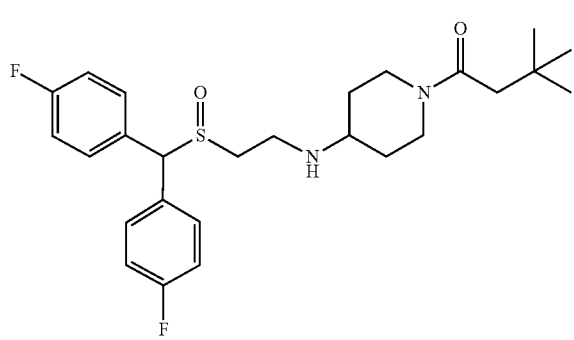 [SMILES: CC(C)(C)CC(=O)N1CCC(NCCS(=O)C(c2ccc(F)cc2)c2ccc(F)cc2)CC1]
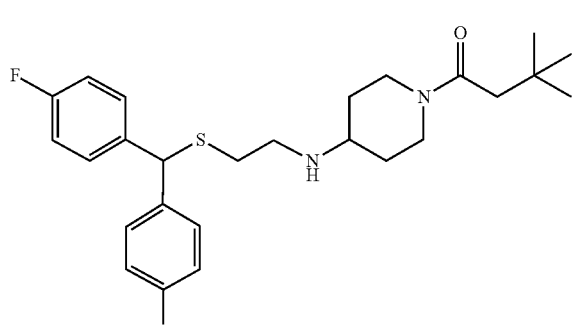
TABLE 1-continued
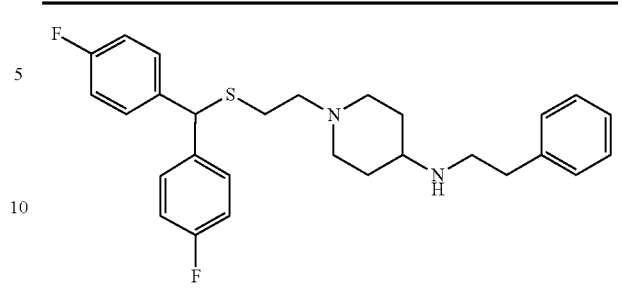
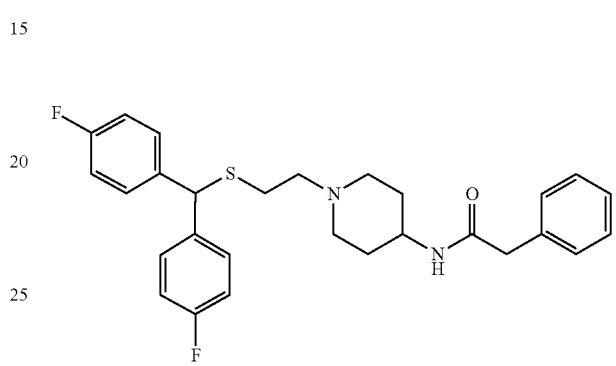
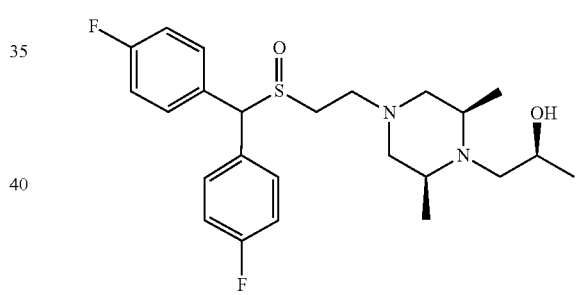
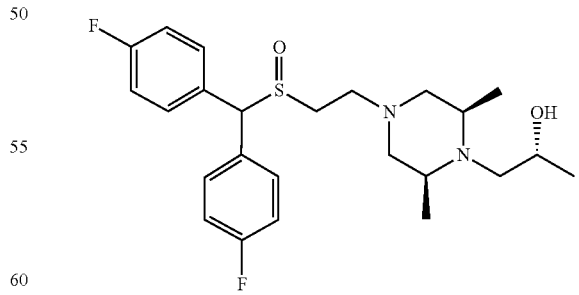

TABLE 2

| Compound | Structure | DAT (rat striatum) $K_i \pm$ SEM (nM) | n | SERT (rat mid-brain-stem) $K_i \pm$ SEM (nM) | n | σ1 (Guinea Pig Cortex) $K_d \pm$ SEM (nM) | n | SERT/ DAT | σ1/ SERT | σ1/ DAT |
|---|---|---|---|---|---|---|---|---|---|---|
| JBG01-052 | 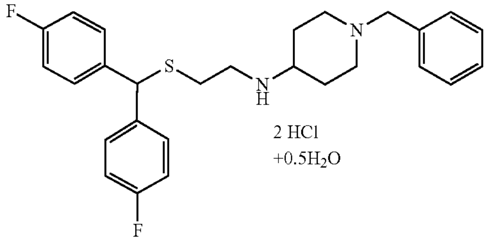 [SMILES: Fc1ccc(C(SCCNC2CCN(Cc3ccccc3)CC2)c2ccc(F)cc2)cc1] | 32.9 ± 5.86 | 4 | 407 ± 57.9 | 3 | 3.97 ± 0.767 | 3 | 12.37 | 0.0098 | 0.12 |
| JBG01-056 | 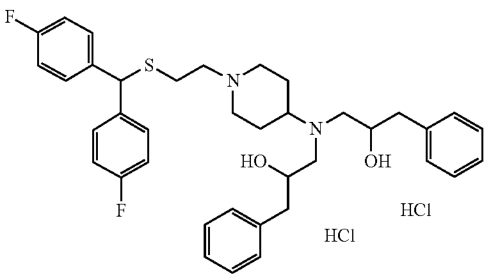 [SMILES: OC(Cc1ccccc1)CN(CC(O)Cc1ccccc1)C1CCN(CCSC(c2ccc(F)cc2)c2ccc(F)cc2)CC1 ; Cl ; Cl] | 186 ± 46.4 | 4 | 1570 ± 315 | 4 | 326 ± 22.4 | 3 | 8.44 | 0.21 | 1.75 |
| JBG01-061 | 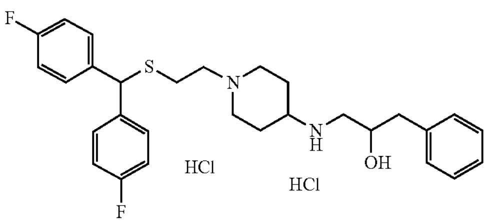 [SMILES: OC(CNC1CCN(CCSC(c2ccc(F)cc2)c2ccc(F)cc2)CC1)Cc1ccccc1 ; Cl ; Cl] | 47.7 ± 2.62 | 3 | 66.3 ± 2.810 | 3 | 88 ± 4.02 | 3 | 1.39 | 1.33 | 1.84 |
| JBG01-057 | 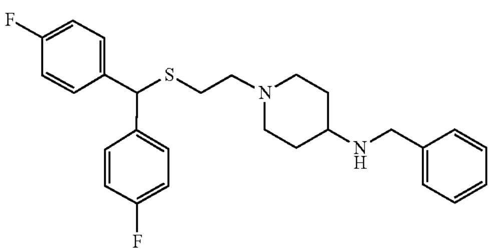 [SMILES: Fc1ccc(C(SCCN2CCC(NCc3ccccc3)CC2)c2ccc(F)cc2)cc1] | 108 ± 17.5 | 3 | 329 ± 34.3 | 4 | 60.9 ± 8.90 | 3 | 3.05 | 0.19 | 0.56 |
| JBG01-058 | 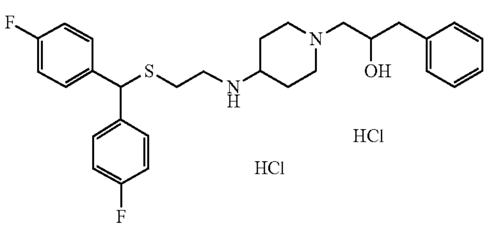 [SMILES: OC(Cc1ccccc1)CN1CCC(NCCSC(c2ccc(F)cc2)c2ccc(F)cc2)CC1 ; Cl ; Cl] | 32 ± 9.48 | 6 | 128 ± 33.2 | 5 | 309 ± 38.8 | 3 | 4.00 | 2.41 | 9.66 |

TABLE 2-continued
| Compound | Structure | DAT (rat striatum) $K_i \pm$ SEM (nM) | n | SERT (rat mid-brain-stem) $K_i \pm$ SEM (nM) | n | σ1 (Guinea Pig Cortex) $K_d \pm$ SEM (nM) | n | SERT/ DAT | σ1/ SERT | σ1/ DAT |
|---|---|---|---|---|---|---|---|---|---|---|
| JBG01-077 | 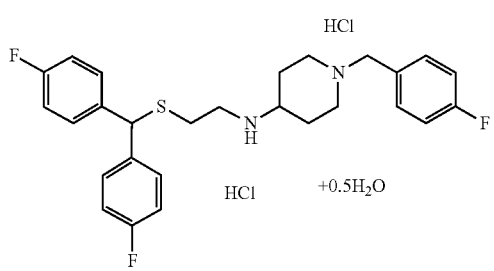 [SMILES: Cl ; Fc1ccc(CN2CCC(NCCSC(c3ccc(F)cc3)c3ccc(F)cc3)CC2)cc1 ; Cl] | 25.5 ± 6.95 | 4 | 277 ± 5.94 | 3 | 13.3 ± 2.75 | 4 | 10.86 | 0.048 | 0.52 |
| JBG01-078 | 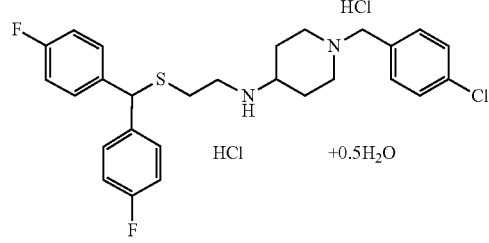 [SMILES: Cl ; Fc1ccc(C(SCCNC2CCN(Cc3ccc(Cl)cc3)CC2)c2ccc(F)cc2)cc1 ; Cl] | 39.6 ± 9.27 | 3 | 356 ± 0.862 | 3 | 45.5 ± 13.2 | 5 | 8.99 | 0.13 | 1.15 |
| JBG01-083 | 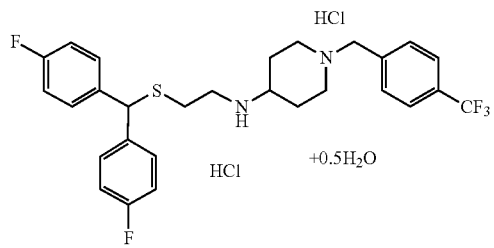 [SMILES: Cl ; Fc1ccc(C(SCCNC2CCN(Cc3ccc(C(F)(F)F)cc3)CC2)c2ccc(F)cc2)cc1 ; Cl] | 190 ± 47.9 | 3 | 1620 ± 175 | 3 | 186 ± 53 | 3 | 8.53 | 0.11 | 0.98 |
| JBG01-084 | 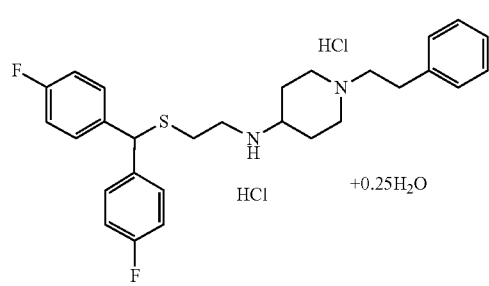 [SMILES: Fc1ccc(C(SCCNC2CCN(CCc3ccccc3)CC2)c2ccc(F)cc2)cc1 ; Cl ; Cl] | 31.5 ± 5.32 | 3 | 144 ± 17.0 | 3 | 57.7 ± 6.63 | 3 | 4.57 | 0.40 | 1.83 |
| JBG01-064 | 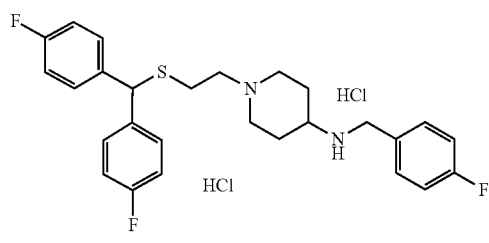 [SMILES: Fc1ccc(CNC2CCN(CCSC(c3ccc(F)cc3)c3ccc(F)cc3)CC2)cc1 ; Cl ; Cl] | 55.9 ± 6.08 | 3 | 267 ± 9.25 | 3 | 41.4 ± 10.9 | 4 | 4.78 | 0.16 | 0.74 |

TABLE 2-continued

| Compound | Structure | DAT (rat striatum) $K_i \pm$ SEM (nM) | n | SERT (rat mid-brain-stem) $K_i \pm$ SEM (nM) | n | σ1 (Guinea Pig Cortex) $K_d \pm$ SEM (nM) | n | SERT/ DAT | σ1/ SERT | σ1/ DAT |
|---|---|---|---|---|---|---|---|---|---|---|
| JBG01-086 | 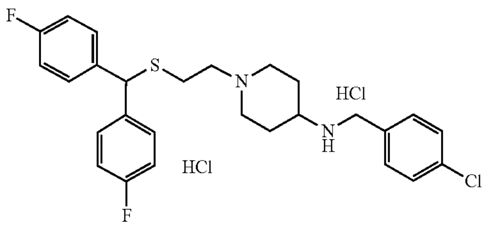 [SMILES: Fc1ccc(C(SCCN2CCC(NCc3ccc(Cl)cc3)CC2)c2ccc(F)cc2)cc1 ; Cl ; Cl] | 86.5 ± 35.6 | 4 | 395 ± 56.6 | 3 | 62.4 ± 6.95 | 3 | 4.57 | 0.16 | 0.72 |
| JBG01-087 | 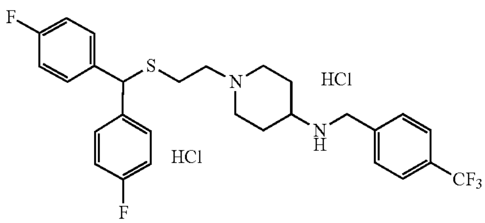 [SMILES: Fc1ccc(C(SCCN2CCC(NCc3ccc(C(F)(F)F)cc3)CC2)c2ccc(F)cc2)cc1 ; Cl ; Cl] | 128 ± 31.9 | 4 | 1040 ± 190 | 3 | 162 ± 32.5 | 3 | 8.13 | 0.16 | 1.27 |
| JBG02-009 | 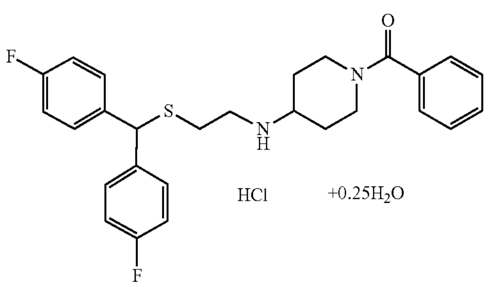 [SMILES: O=C(c1ccccc1)N1CCC(NCCSC(c2ccc(F)cc2)c2ccc(F)cc2)CC1 ; Cl] | 4.51 ± 0.86 | 3 | 282 ± 25.7 | 3 | 2.04 ± 0.298 | 3 | 62.53 | 0.0072 | 0.45 |
| JBG02-014 | 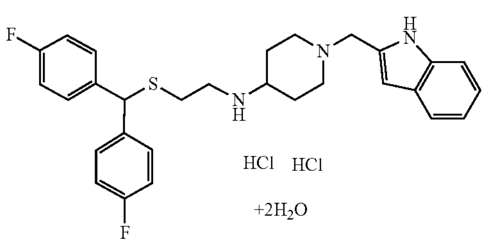 [SMILES: Fc1ccc(C(SCCNC2CCN(Cc3cc4ccccc4[nH]3)CC2)c2ccc(F)cc2)cc1 ; Cl ; Cl] | 179 ± 22 | 3 | 1720 ± 516 | 3 | 205 ± 42.2 | 3 | 9.61 | 0.12 | 1.15 |
| JBG02-015 | 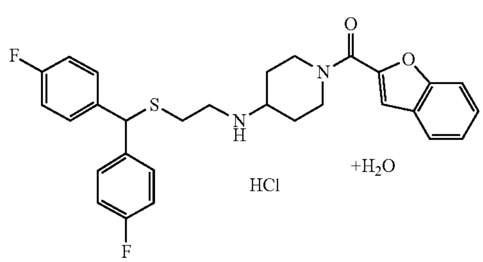 | 115 ± 19.5 | 3 | 96.4 ± 23.7 | 3 | 304 ± 23.1 | 3 | 0.84 | 3.15 | 2.64 |

TABLE 2-continued
| Compound | Structure | DAT (rat striatum) $K_i \pm$ SEM (nM) | n | SERT (rat mid-brain-stem) $K_i \pm$ SEM (nM) | n | σ1 (Guinea Pig Cortex) $K_d \pm$ SEM (nM) | n | SERT/ DAT | σ1/ SERT | σ1/ DAT |
|---|---|---|---|---|---|---|---|---|---|---|
| JBG02-018 | 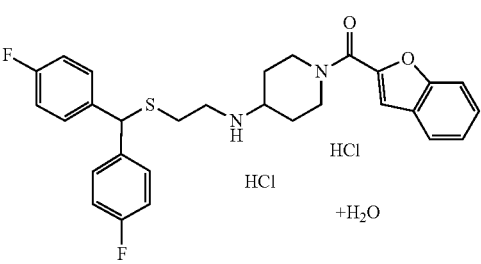 | 120 ± 24.3 | 3 | 691 ± 98.8 | 3 | 205 ± 1.02 | 3 | 5.76 | 0.30 | 1.71 |
| JBG02-028 | 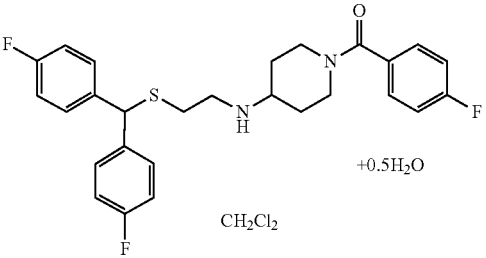 | 7.24 ± 0.78 | 3 | 485 ± 32.0 | 3 | 32.1 ± 4.38 | 3 | 66.99 | 0.066 | 4.43 |
| JBG02-029 | 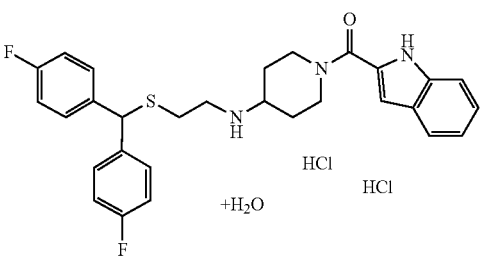 | 180 ± 39.8 | 3 | 938 ± 76.5 | 3 | 1130 ± 285 | 3 | 5.21 | 1.20 | 6.28 |
| JBG02-054 | 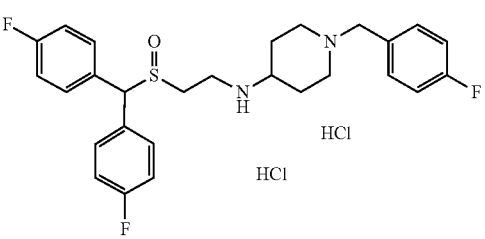 [SMILES: O=S(CCNC1CCN(Cc2ccc(F)cc2)CC1)C(c1ccc(F)cc1)c1ccc(F)cc1 ; Cl ; Cl] | 50.6 ± 11.2 | 4 | 370 ± 23.7 | 3 | 26.5 ± 3.88 | 3 | 7.31 | 0.072 | 0.52 |
| JBG02-055 | 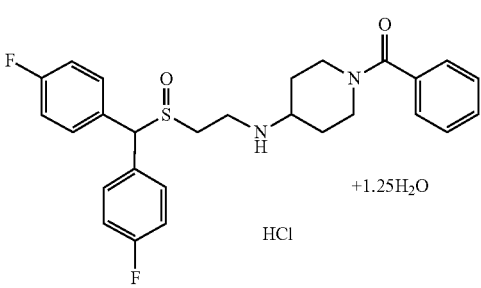 [SMILES: O=C(c1ccccc1)N1CCC(NCCS(=O)C(c2ccc(F)cc2)c2ccc(F)cc2)CC1 ; Cl ; "+1.25H2O"] | 79.1 ± 20.6 | 3 | 7730 ± 732 | 3 | 585 ± 21.5 | 3 | 97.72 | 0.076 | 7.40 |

TABLE 2-continued

| Compound | Structure | DAT (rat striatum) $K_i \pm$ SEM (nM) | n | SERT (rat mid-brain-stem) $K_i \pm$ SEM (nM) | n | σ1 (Guinea Pig Cortex) $K_d \pm$ SEM (nM) | n | SERT/ DAT | σ1/ SERT | σ1/ DAT |
|---|---|---|---|---|---|---|---|---|---|---|
| JBG02-056 | (4-F-C6H4)(4-F-C6H4)CH-S(=O)-CH2CH2-NH-(piperidin-4-yl)-N-C(=O)-(4-F-C6H4) · +2H2O · HCl | 77.2 ± 4.54 | 4 | 4620 ± 379 | 3 | 1320 ± 36.5 | 3 | 59.84 | 0.29 | 17.10 |
| JBG02-057 | (4-F-C6H4)(4-F-C6H4)CH-S(=O)-CH2CH2-NH-(piperidin-4-yl)-N-CH2-CH(OH)-CH2-C6H5 · +3HCl · H2O · +0.33NH4OH | 91.8 ± 21.3 | 3 | 595 ± 54.1 | 3 | 346 ± 27.1 | 3 | 6.48 | 0.58 | 3.77 |
| JBG02-064 | (4-F-C6H4)(4-F-C6H4)CH-S-CH2CH2-NH-(piperidin-4-yl)-N-C(=O)-C(CH3)3 · HCl · H2O | 352 ± 137 | 4 | 1000 ± 228 | 3 | 163 ± 8.77 | 3 | 2.84 | 0.16 | 0.46 |
| RDS03-094 | (4-F-C6H4)(4-F-C6H4)CH-S-CH2CH2-(2,6-dimethylpiperazinyl)-N-CH2-CH(OH)-CH3 · 2.5 Oxalate · 0.5 H2O | 23.5 ± 2.12 | 3 | 14800 ± 2260 | 3 | 5.62 ± 1.21 | 3 | 629.79 | 0.00038 | 0.24 |
| RDS03-095 | (4-F-C6H4)(4-F-C6H4)CH-S-CH2CH2-(2,6-dimethylpiperazinyl)-N-CH2-CH(OH)-CH2-C6H5 · 2.5 Oxalate · 0.5 H2O | 2.00 ± 0.15 | 3 | 1600 ± 152 | 3 | 15.2 ± 3.48 | 3 | 800.00 | 0.010 | 7.60 |

TABLE 2-continued

| Compound | Structure | DAT (rat striatum) $K_i \pm$ SEM (nM) | n | SERT (rat mid-brain-stem) $K_i \pm$ SEM (nM) | n | σ1 (Guinea Pig Cortex) $K_d \pm$ SEM (nM) | n | SERT/ DAT | σ1/ SERT | σ1/ DAT |
|---|---|---|---|---|---|---|---|---|---|---|
| RDS04-010 | •2 Oxalate•H$_2$O | 245 ± 49.7 | 3 | 19000 ± 2550 | 3 | 315 ± 19.1 | 3 | 77.55 | 0.017 | 1.29 |
| RDS04-011 | •2 Oxalate•2H$_2$O | 6.78 ± 2.97 | 4 | 2560 ± 181 | 3 | 75.4 ± 7.35 | 3 | 377.58 | 0.029 | 11.12 |
| RDS04-002 | •2 Oxalate•1/2 H$_2$O | 125 ± 9.70 | 3 | 124 ± 38.2 | 3 | 45.5 ± 11.1 | 3 | 0.99 | 0.37 | 0.36 |
| RDS04-014 | •2 Oxalate | 449 ± 120 | 4 | 617 ± 54.8 | 4 | 65.1 ± 1.34 | 3 | 1.37 | 0.11 | 0.14 |
| JBG02-083 | Oxalate•0.25H$_2$O | 178 ± 35 | 3 | 1010 ± 94 | 3 | 46.4 ± 4.13 | 3 | 5.67 | — | 0.26 |

TABLE 2-continued

| Compound | Structure | DAT (rat striatum) $K_i \pm$ SEM (nM) | n | SERT (rat mid-brain-stem) $K_i \pm$ SEM (nM) | n | σ1 (Guinea Pig Cortex) $K_d \pm$ SEM (nM) | n | SERT/DAT | σ1/SERT | σ1/DAT |
|---|---|---|---|---|---|---|---|---|---|---|
| JBG02-080 | (structure) Oxalate•0.5H$_2$O | 407 ± 65 | 3 | 1600 ± 164 | 3 | 269 ± 23 | 3 | 3.93 | — | 0.66 |
| JBG02-066 | (structure) | 279 ± 39.4 | 3 | 947 ± 101 | 3 | 315 ± 76 | 3 | 3.39 | — | 1.13 |
| JBG02-072 | (structure) | 10200 ± 3610 | 3 | 32000 ± 6760 | 3 | 11200 ± 2540 | * | 3.14 | — | 1.10 |
| JBG02-074 | (structure) | 431 ± 28.2 | 3 | 6990 ± 229 | 3 | 542 ± 224 | * | 16.22 | — | 1.26 |

Example 5. Phase I Metabolic Stability

Methods: Phase I metabolic stability assays were conducted in rat liver microsomes. For phase I metabolism, the reactions were carried out with 100 mM potassium phosphate buffer, pH 7.4, in the presence of NADPH regenerating system (1.3 mM NADPH, 3.3 mM glucose 6-phosphate, 3.3 mM MgCl$_2$, 0.4 U/mL glucose-6-phosphate dehydrogenase, 50 M sodium citrate). Reactions in triplicate were initiated by addition of the liver microsomes to the incubation mixture (compound final concentration was 10 μM; 0.5 mg/mL microsomes). Compound disappearance was monitored via LC/MS/MS. Chromatographic analysis was performed using an Accela™ ultra high-performance system consisting of an analytical pump, and an autosampler coupled with TSQ Vantage mass spectrometer (Thermo Fisher Scientific Inc., Waltham Mass.). Separation of the analyte from potentially interfering material was achieved at ambient temperature using Agilent Eclipse Plus column (100×2.1 mm i.d.) packed with a 1.8 μm C18 stationary phase. The mobile phase used was composed of 0.100 Formic Acid in Acetonitrile and 0.10% Formic Acid in H$_2$O with gradient elution, starting with 10% (organic) linearly increasing to 99% up to 2.5 min, maintaining at 99% (2.5-3.5 min) and re-equilibrating to 10% by 4.5 min. The total run time for each analyte was 5.0 min. The results of the assays are provided in Table 4.

TABLE 3

| Compound | Parent Ion (M + H) | Transitions |
|---|---|---|
| JBG01-058 | 497.061 | 185.992, 203.010, 218.101 |
| JBG01-061 | 496.994 | 183.000, 203.004 |
| JBG01-077 | 471.115 | 183.038, 203.049 |
| JBG02-009 | 468.071 | 183.031, 203.033 |
| JBG02-028 | 484.673 | 183.015, 203.014 |
| Losartan | 422.860 | 180.090, 208.113 |
| JBG-02-054 | 487.232 | 183.104, 284.215 |
| JBG-02-056 | 501.165 | 183.055, 203.062 |
| JBG-02-057 | 513.132 | 310.219 |
| Losartan | 423.023 | 180.086, 207.086 |
| RDS-03-094 | 435.184 | 182.998, 202.994 |
| RDS-03-095 | 511.226 | 183.018, 202.999 |
| RDS-04-002 | 537.162 | 183.024, 203.010 |
| RDS-04-010 | 451.152 | 203.115, 248.175 |
| RDS-04-011 | 527.194 | 324.218 |
| Losartan | 423.023 | 180.086, 207.086 |

TABLE 4

| Time (min.) | Rat | Negative Control |
|---|---|---|
| JBG01-058 Phase I in Liver Microsomes | | |
| 0 | 100% | 100% |
| 30 | 98% | — |
| 60 | 74% | 96% |
| JBG01-061 Phase I in Liver Microsomes | | |
| 0 | 100% | 100% |
| 30 | 83% | — |
| 60 | 69% | 109% |
| JBG01-077 Phase I in Liver Microsomes | | |
| 0 | 100% | 100% |
| 30 | 88% | — |
| 60 | 70% | 111% |
| JBG02-009 Phase I in Liver Microsomes | | |
| 0 | 100% | 100% |
| 30 | 20% | — |
| 60 | 7% | 100% |
| JBG02-028 Phase I in Liver Microsomes | | |
| 0 | 100% | 100% |
| 30 | 40% | — |
| 60 | 24% | 101% |
| JBG02-054 Phase I in Liver Microsomes | | |
| 0 | 100% | 100% |
| 30 | 100% | 102% |
| 60 | 95% | 102% |
| JBG02-056 Phase I in Liver Microsomes | | |
| 0 | 100% | 100% |
| 30 | 100% | 97% |
| 60 | 79% | 91% |
| JBG02-057 Phase I in Liver Microsomes | | |
| 0 | 100% | 100% |
| 30 | 50% | 102% |
| 60 | 22% | 100% |
| RDS03-094 Phase I in Liver Microsomes | | |
| 0 | 100% | 100% |
| 30 | 99% | 106% |
| 60 | 68% | 109% |
| RDS03-095 Phase I in Liver Microsomes | | |
| 0 | 100% | 100% |
| 30 | 42% | 117% |
| 60 | 10% | 125% |
| RDS04-002 Phase I in Liver Microsomes | | |
| 0 | 100% | 100% |
| 30 | 100% | 128% |
| 60 | 100% | 125% |
| RDS04-010 Phase I in Liver Microsomes | | |
| 0 | 100% | 100% |
| 30 | 115% | 130% |
| 60 | 95% | 108% |
| RDS04-011 Phase I in Liver Microsomes | | |
| 0 | 100% | 100% |
| 30 | 58% | 132% |
| 60 | 26% | 106% |

For compounds JBG01-058, JBG01-061, JBG01-077, JBG02-054, and JBG02-056, the results show that the compounds show stability to Phase I metabolism in rat liver microsomes fortified with NADPH. The compounds show stability in negative control studies with Rat liver microsomes lacking NADPH fortification. For compounds JBG02-009, JBG02-028, and JBG02-057, the results show the compounds show susceptibility to Phase I in rat liver microsomes fortified with NADPH. The compound shows stability in negative control studies with Rat liver microsomes lacking NADPH fortification. The results of the study for the foregoing compounds are found in FIG. 1.

Figure 2:
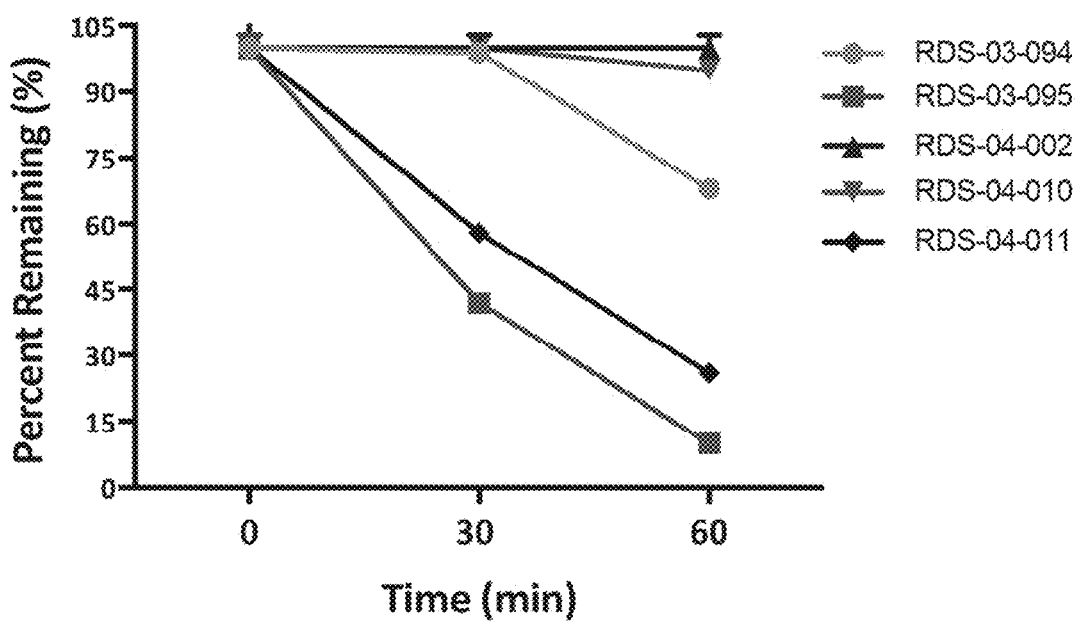
FIG. 2: Phase I metabolic stability assay results for substituted piperazine analogues and a spirobicyclodiaza analogue.

For compounds RDS04-002 and RDS04-010, the results show the compounds show stability to Phase I metabolism in rat liver microsomes fortified with NADPH, while RDS03-094 shows moderate stability. The compounds show stability in negative control studies with Rat liver microsomes lacking NADPH fortification. For RDS03-095 and RDS4-011, these compounds show susceptibility to Phase I metabolism in rat liver microsomes fortified with NADPH. These compounds show stability in negative control studies with Rat liver microsomes lacking NADPH fortification. The results of the study for the foregoing compounds are found in FIG. 2.

The terms "a" and "an" do not denote a limitation of quantity, but rather denote the presence of at least one of the referenced item. The term "or" means "and/or". Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. The modifier "about" used in connection with a quantity is inclusive of the stated value and has the meaning dictated by the context (e.g., includes the degree of error associated with measurement of the particular quantity).

The endpoints of all ranges directed to the same component or property are inclusive of the endpoints, are independently combinable, and include all intermediate points and ranges (e.g., ranges of "up to about 25 wt. %, or, more specifically, about 5 wt. % to about 20 wt. %," is inclusive of the endpoints and all intermediate values of the ranges of "about 5 wt. % to about 25 wt. %," such as about 10 wt % to about 23 wt %, etc.).

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

The invention includes at least the following embodiments.

Embodiment 1. A compound of Formula I

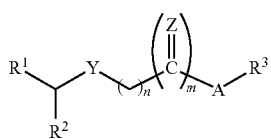

Formula I or a pharmaceutically acceptable salt thereof,
wherein $R^1$ and $R^2$ each independently is $C_6$-$C_{12}$ aryl, monocyclic heteroaryl, or bicyclic heteroaryl, each of which may be optionally substituted with 1, 2, or 3 substituents, each substituent independently selected from halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, or di-$C_1$-$C_2$ alkylamino; Y is S, S(O), or S(O)$_2$; n is 1, 2, or 3; Z is O, S, or 2H; m is 0 or 1; A is one of A1 to A4

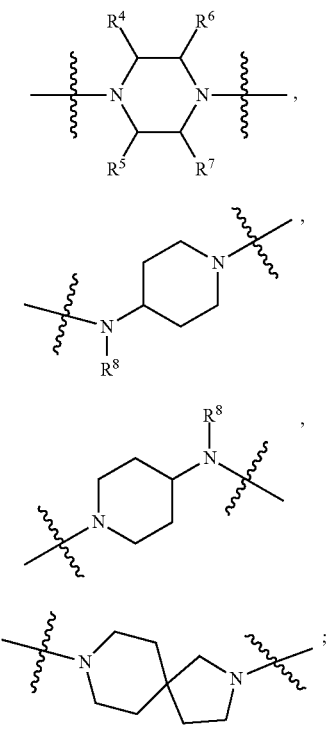

$R^4$, $R^5$, $R^6$, and $R^7$ each independently is hydrogen, $C_1$-$C_6$ alkyl, $C_2$-$C_6$ alkenyl, $C_1$-$C_6$ haloalkyl, or $C_2$-$C_6$ alkanoyl, with the proviso that at least one of $R^4$, $R^5$, $R^6$, and $R^7$ is other than hydrogen; $R^8$ is hydrogen, $C_1$-$C_6$ alkyl, $C_1$-$C_6$ haloalkyl, or $C_2$-$C_6$ alkanoyl; and $R^3$ is hydrogen, $C_1$-$C_8$ alkyl, $C_1$-$C_6$ haloalkyl, $C_2$-$C_6$ alkenyl, $C_3$-$C_7$ cycloalkyl, $C_2$-$C_6$ alkanoyl, aryl-(C=O)—, monocyclic heteroaryl-(C=O)—, bicyclic heteroaryl-(C=O)—, ($C_3$-$C_7$ cycloalkyl)$C_0$-$C_6$ alkyl, ($C_3$-$C_7$ cycloalkenyl)$C_0$-$C_6$ alkyl, (heterocycloalkyl)$C_0$-$C_6$ alkyl, (heterocycloalkenyl)$C_0$-$C_6$ alkyl, (aryl)$C_0$-$C_6$ alkyl, (monocyclic heteroaryl)$C_0$-$C_6$ alkyl, (bicyclic heteroaryl)$C_0$-$C_6$ alkyl, or ($C_2$-$C_6$ alkanoyl)$C_0$-$C_6$ alkyl, wherein each alkyl independently can optionally be substituted with 1 or 2 substituents and each aryl and heteroaryl independently can optionally be substituted with 1, 2, or 3 substituents, wherein each substituent is independently selected from halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, di-$C_1$-$C_2$ alkylamino, or phenyl, wherein the phenyl can optionally be substituted with halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, or di-$C_1$-$C_2$ alkylamino; with the proviso that when A is A2, $R^1$ and $R^2$ are each phenyl, Y is S, n is 1, m is 1, Z is O, and $R^8$ is methyl, then either i) $R^3$ is other than hydrogen or unsubstituted $C_1$-$C_8$ alkyl, or ii) both $R^1$ and $R^2$ have at least one substituent.

Embodiment 2. A compound or salt of Embodiment 1 in which each of $R^1$ and $R^2$ independently is an optionally substituted phenyl.

Embodiment 3. A compound or salt of Embodiment 1 or 2 in which Y is S or S(O).

Embodiment 4. A compound or salt of any one of Embodiments 1-3 wherein the substitution on $R^1$ and $R^2$ is fluoro.

Embodiment 5. A compound or salt of any one of Embodiments 1-4 in which Z is O or 2H.

Embodiment 6. A compound or salt of any one of Embodiments 1-4 wherein n is 2 and m is 0.

Embodiment 7. A compound or salt of any one of Embodiments 1-6 wherein $R^3$ is $C_1$-$C_8$ alkyl, $C_1$-$C_6$ haloalkyl, aryl-(C=O)—, monocyclic heteroaryl-(C=O)—, bicyclic heteroaryl-(C=O)—, ($C_3$-$C_7$ cycloalkyl)$C_0$-$C_6$ alkyl, (heterocycloalkyl)$C_0$-$C_6$ alkyl, (heterocycloalkenyl)$C_0$-$C_6$ alkyl, (aryl)$C_0$-$C_6$ alkyl, (monocyclic heteroaryl)$C_0$-$C_6$ alkyl, (bicyclic heteroaryl)$C_0$-$C_6$ alkyl, or ($C_2$-$C_6$ alkanoyl) $C_0$-$C_6$ alkyl, wherein each alkyl independently can optionally be substituted with 1 or 2 substituents, specifically substituted with 1 hydroxyl, and each aryl and heteroaryl independently can optionally be substituted with 1, 2, or 3 substituents.

Embodiment 8. A compound or salt of any one of Embodiments 1-7 wherein A is

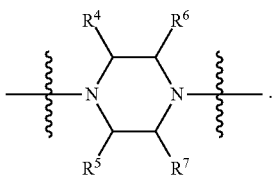

A1

Embodiment 9. A compound or salt of any one of Embodiments 1-7 wherein A is

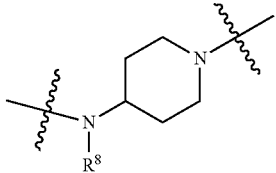

A2

Embodiment 10. A compound or salt of any one of Embodiments 1-7 wherein A is

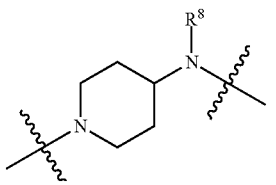

A3

Embodiment 11. A compound or salt of any one of Embodiments 1-7 wherein A is

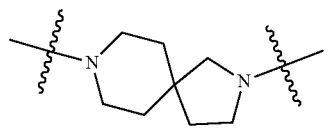

A4

Embodiment 12. A compound or salt of any one of Embodiments 1-11, wherein a sulfoxide fragment has an (R)-configuration or an (S)-configuration.

Embodiment 13. A compound or salt of Embodiment 1 of formula:

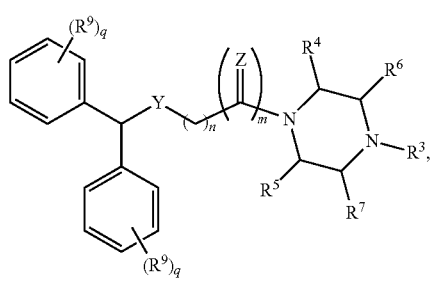

IA1 wherein Y, n, Z, m, $R^3$, $R^4$, $R^5$, $R^6$, and $R^7$ are as defined in Embodiment 1; each instance of q is 0, 1, 2, or 3; and each instance of $R^9$ is halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, or di-$C_1$-$C_2$ alkylamino.

Embodiment 14. A compound or salt of Embodiment 1 of formula:

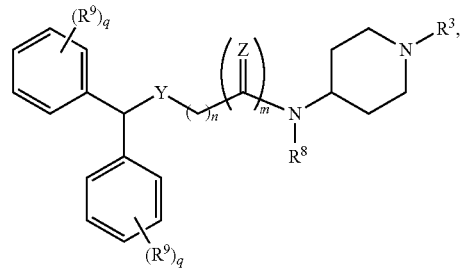

IA2 wherein Y, n, Z, m, $R^3$, and $R^8$ are as defined in Embodiment 1; each instance of q is 0, 1, 2, or 3; and each instance of $R^9$ is halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, or di-$C_1$-$C_2$ alkylamino.

Embodiment 15. A compound or salt of Embodiment 1 of formula:

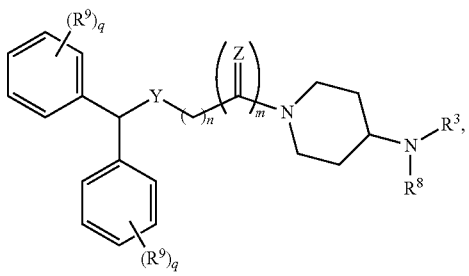

IA3 wherein Y, n, Z, m, $R^3$, and $R^8$ are as defined in Embodiment 1; each instance of q is 0, 1, 2, or 3; and each instance of $R^9$ is halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, or di-$C_1$-$C_2$ alkylamino.

Embodiment 16. A compound or salt of Embodiment 1 of formula:

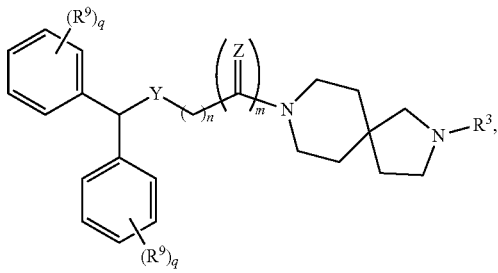

IA4 wherein Y, n, Z, m, and $R^3$ are as defined in Embodiment 1; each instance of q is 0, 1, 2, or 3; and each instance of $R^9$ is halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, or di-$C_1$-$C_2$ alkylamino.

Embodiment 17. A compound or salt of Embodiment 1 as disclosed in Table 1 or Table 2.

Embodiment 18. A compound of Embodiment 1, comprising 1-((2S,6R)-4-(2-(bis(4-fluorophenyl)methylthio) ethyl)-2,6-dimethylpiperazin-1-yl)propan-2-ol; (S)-1-((2S,6R)-4-(2-(bis(4-fluorophenyl)methylthio)ethyl)-2,6-dimethylpiperazin-1-yl)propan-2-ol; (R)-1-((2S,6R)-4-(2-(bis(4-fluorophenyl)methylthio)ethyl)-2,6-dimethylpiperazin-1-yl)propan-2-ol; or a pharmaceutically acceptable salt thereof.

Embodiment 19. A pharmaceutical composition comprising a compound or salt of any one of Embodiments 1-18, and at least one pharmaceutically acceptable carrier.

Embodiment 20. The pharmaceutical composition of Embodiment 19, wherein the composition is formulated as an injectable fluid, an aerosol, a cream, a gel, a tablet, a pill, a capsule, a syrup, an ophthalmic solution, or a transdermal patch.

Embodiment 21. A package comprising the pharmaceutical composition of Embodiment 19 or 20 in a container and further comprising instructions for using the composition in order to elicit a wake-promoting, cognition-enhancing or mood-enhancing effect in a patient or for treating a patient suffering from substance use disorders, attention deficit (hyperactivity) disorder, depressive disorders, sleep disorders, cognitive impairment, or obesity.

Embodiment 22. A method for treating substance use disorders, attention deficit (hyperactivity) disorder, depressive disorders, sleep disorders or cognitive impairment or for eliciting a wake-promoting, cognition-enhancing or mood-enhancing effect, comprising: providing a therapeutically effective amount of a compound or salt of any one of Embodiments 1-18 to a patient in need of such treatment, optionally in the form of a pharmaceutical composition according to Embodiment 19 or 20.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A compound of Formula I

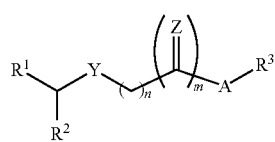

Formula I or a pharmaceutically acceptable salt thereof,
wherein
$R^1$ and $R^2$ each independently is $C_6$-$C_{12}$ aryl, monocyclic heteroaryl, or bicyclic heteroaryl, each of which may be optionally substituted with 1, 2, or 3 substituents, each substituent independently selected from halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono- $C_1$-$C_2$ alkylamino, or di-$C_1$-$C_2$ alkylamino;

Y is S, S(O), or S(O)$_2$;
n is 1, 2, or 3;
Z is O, S, or 2H;
m is 0 or 1;
A is one of A1 to A4

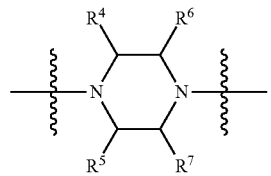

A1

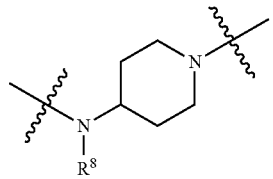

A2

$R^4$ and $R^5$ each independently is hydrogen, and $R^6$ and $R^7$ each independently is $C_1$-$C_6$ alkyl;

$R^8$ is hydrogen, $C_1$-$C_6$ alkyl, $C_1$-$C_6$ haloalkyl, or $C_2$-$C_6$ alkanoyl; and $R^3$ is hydrogen, $C_1$-$C_8$ alkyl, $C_1$-$C_6$ haloalkyl, $C_2$-$C_6$ alkenyl, $C_3$-$C_7$ cycloalkyl, $C_2$-$C_6$ alkanoyl, aryl-(C=O)—, monocyclic heteroaryl-(C=O)—, bicyclic heteroaryl-(C=O)—, ($C_3$-$C_7$ cycloalkyl)$C_0$-$C_6$ alkyl, ($C_3$-$C_7$ cycloalkenyl)$C_0$-$C_6$ alkyl, (heterocycloalkyl) $C_0$-$C_6$ alkyl, (heterocycloalkenyl)$C_0$-$C_6$ alkyl, (aryl)$C_0$-$C_6$ alkyl, (monocyclic heteroaryl)$C_0$-$C_6$ alkyl, (bicyclic heteroaryl)$C_0$-$C_6$ alkyl, or ($C_2$-$C_6$ alkanoyl)$C_0$-$C_6$ alkyl, wherein each alkyl independently can optionally be substituted with 1 or 2 substituents and each aryl and heteroaryl independently can optionally be substituted with 1, 2, or 3 substituents, wherein each substituent is independently selected from halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, di-$C_1$-$C_2$ alkylamino, or phenyl, wherein the phenyl can optionally be substituted with halogen, hydroxyl, amino, nitro, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkoxy, —COOH, —CHO, —CONH$_2$, $C_2$-$C_6$ alkanoyl, mono-$C_1$-$C_2$ alkylamino, or di-$C_1$-$C_2$ alkylamino;

with the proviso that when A is A2, $R^1$ and $R^2$ are each phenyl, Y is S, n is 1, m is 1, Z is O, and $R^8$ is methyl, then either
i) $R^3$ is other than hydrogen or unsubstituted $C_1$-$C_8$ alkyl, or
ii) both $R^1$ and $R^2$ have at least one substituent.

2. A compound or salt of claim 1 in which each of $R^1$ and $R^2$ independently is an optionally substituted phenyl.

3. A compound or salt of claim 1 in which Y is S or S(O).

4. A compound or salt of claim 1 wherein the substitution on $R^1$ and $R^2$ is fluoro.

5. A compound or salt of claim 1 in which Z is O or 2H.

6. A compound or salt of claim 1 wherein n is 2 and m is 0.

7. A compound or salt of claim 1 wherein R³ is C₁-C₈ alkyl, C₁-C₆ haloalkyl, aryl-(C═O)—, monocyclic heteroaryl-(C═O)—, bicyclic heteroaryl-(C═O)—, (C₃-C₇ cycloalkyl)C₀-C₆ alkyl, (heterocycloalkyl)C₀-C₆ alkyl, (heterocycloalkenyl)C₀-C₆ alkyl, (aryl)C₀-C₆ alkyl, (monocyclic heteroaryl)C₀-C₆ alkyl, (bicyclic heteroaryl)C₀-C₆ alkyl, or (C₂-C₆ alkanoyl)C₀-C₆ alkyl, wherein each alkyl independently can optionally be substituted with 1 or 2 substituents, specifically substituted with 1 hydroxyl, and each aryl and heteroaryl independently can optionally be substituted with 1, 2, or 3 substituents.

8. A compound or salt of claim 1 wherein A is

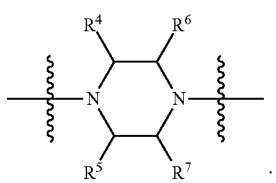

A1

9. A compound or salt of claim 1 wherein a sulfoxide fragment has an (R)-configuration or an (S)-configuration.

10. A compound or salt of claim 1 of formula:

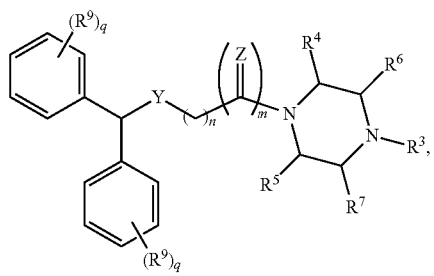

IA1 wherein Y, n, Z, m, R³, R⁴, R⁵, R⁶, and R⁷ are as defined in claim 1;
each instance of q is 0, 1, 2, or 3; and
each instance of R⁹ is halogen, hydroxyl, amino, nitro, cyano, C₁-C₆ alkyl, C₂-C₆ alkenyl, C₁-C₆ alkoxy, C₁-C₆ haloalkyl, C₁-C₆ haloalkoxy, —COOH, —CHO, —CONH₂, C₂-C₆ alkanoyl, mono- C₁-C₂ alkylamino, or di-C₁-C₂ alkylamino.

11. A compound or salt of claim 1, selected from the group consisting of:

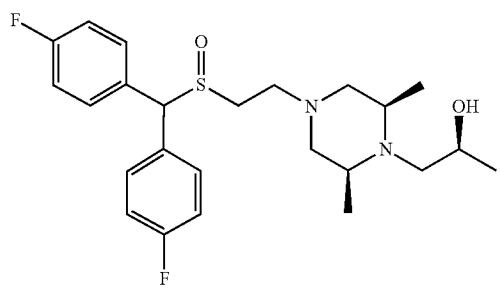

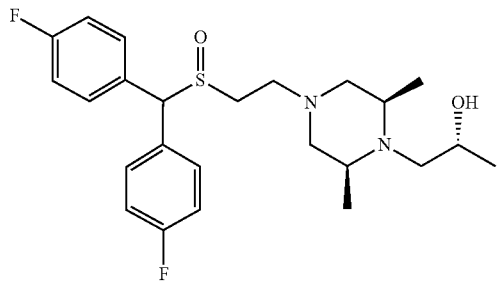

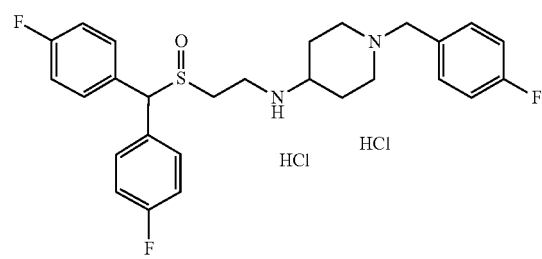

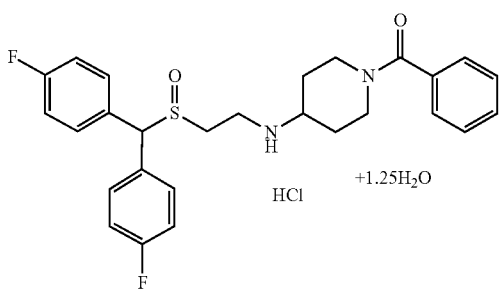

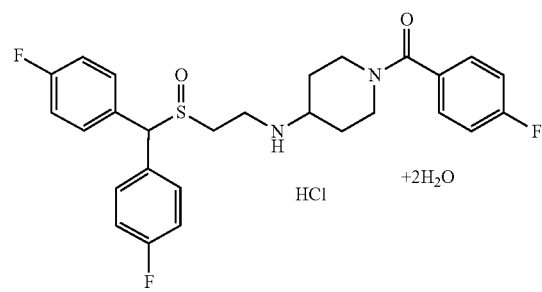 [SMILES: O=C(c1ccc(F)cc1)N1CCC(NCCS(=O)C(c2ccc(F)cc2)c2ccc(F)cc2)CC1 ; Cl ; "+2H2O"]

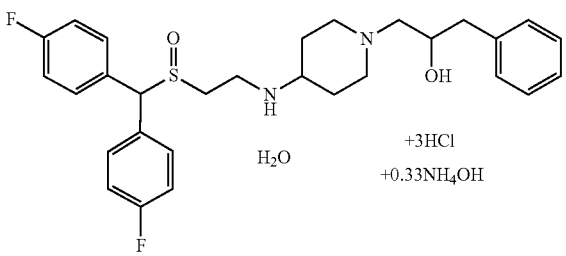

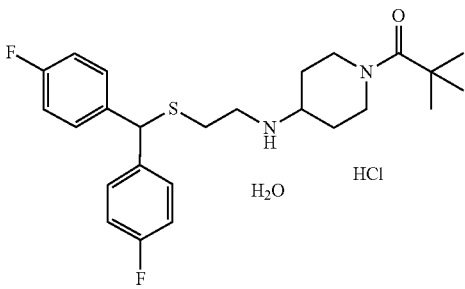

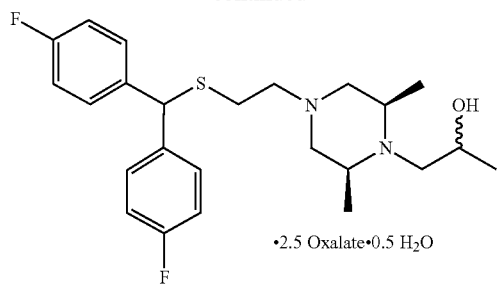
• 2.5 Oxalate•0.5 H₂O
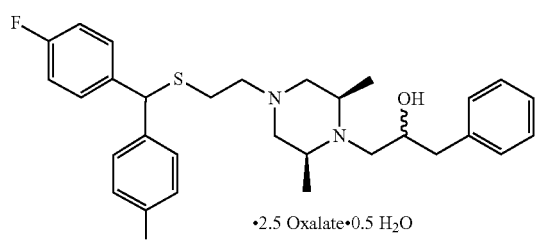
• 2.5 Oxalate•0.5 H₂O
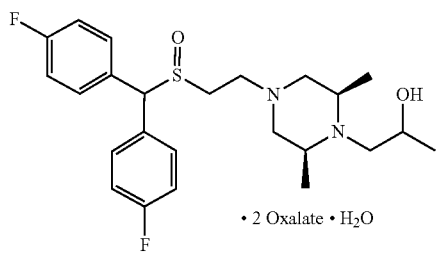
• 2 Oxalate • H₂O
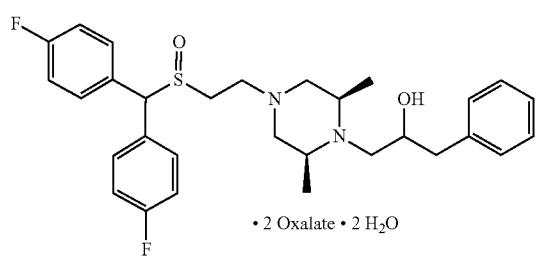 [SMILES: C[C@@H]1CN(CCS(=O)C(c2ccc(F)cc2)c2ccc(F)cc2)C[C@H](C)N1CC(O)Cc1ccccc1]
• 2 Oxalate • 2 H₂O
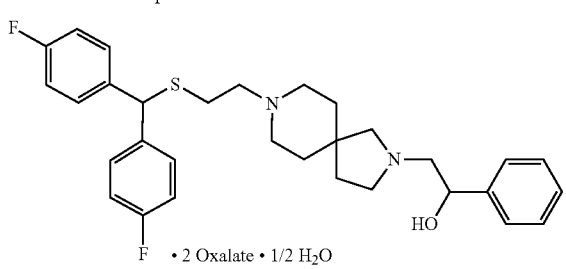
• 2 Oxalate • 1/2 H₂O
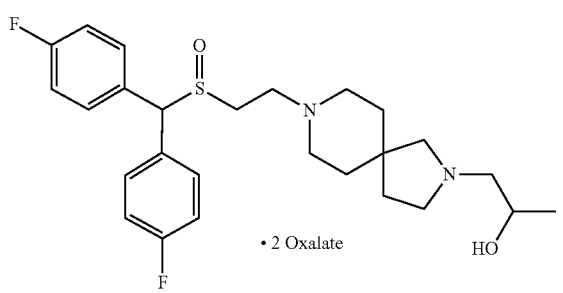
• 2 Oxalate
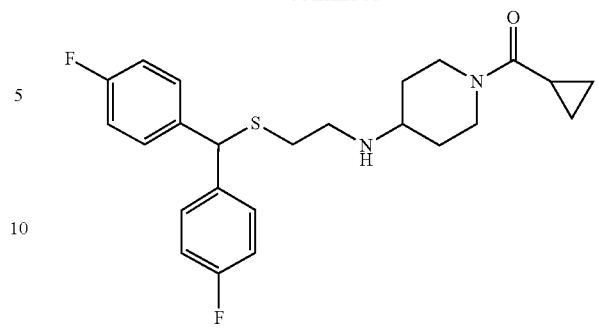
Oxalate•0.25H₂O
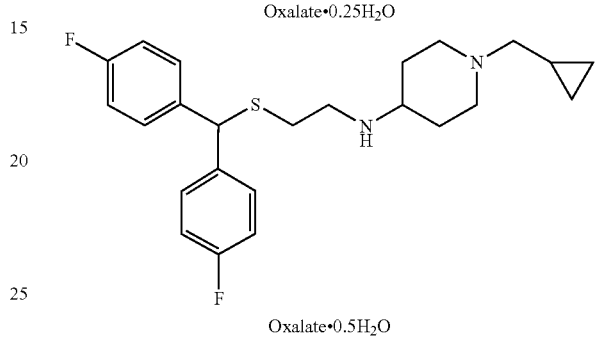
Oxalate•0.5H₂O
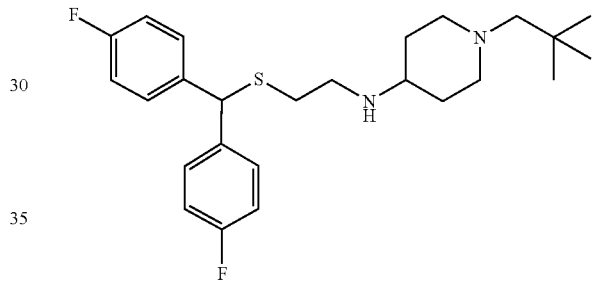
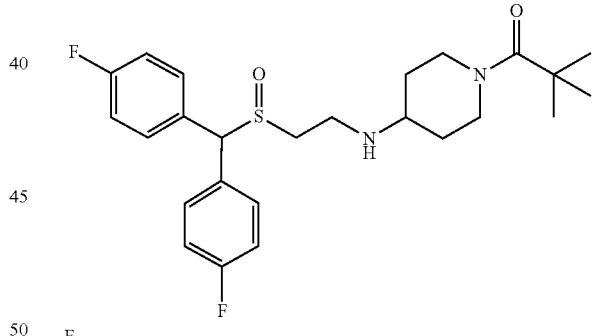
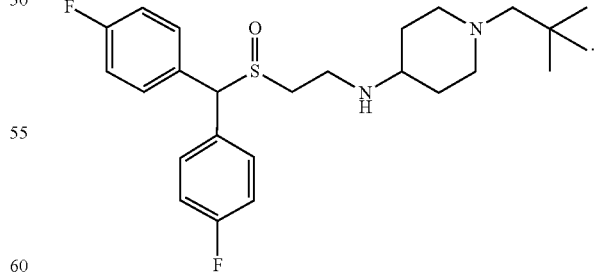
12. A compound of claim 1, comprising 1-(2S,6R)-4-(2-(bis(4-fluorophenyl)methylthio)ethyl)-2,6-dimethylpiperazin-1-yl)propan-2-ol; (S)-1-((2S,6R)-4-(2-(bis(4-fluorophenyl)methylthio)ethyl)-2,6-dimethylpiperazin-1-yl)propan-2-ol; (R)-1-((2S,6R)-4-(2-(bis(4-fluorophenyl)

methylthio)ethyl)-2,6-dimethylpiperazin-1-yl)propan-2-ol; or a pharmaceutically acceptable salt thereof.

13. A pharmaceutical composition comprising a compound or claim 1 and at least one pharmaceutically acceptable carrier.

14. The pharmaceutical composition of claim 13, wherein the composition is formulated as an injectable fluid, an aerosol, a cream, a gel, a tablet, a pill, a capsule, a syrup, an ophthalmic solution, or a transdermal patch.

15. A package comprising the pharmaceutical composition of claim 13 in a container and further comprising instructions for using the composition in order to elicit a wake-promoting, cognition-enhancing or mood-enhancing effect in a patient or for treating a patient suffering from substance use disorders, attention deficit (hyperactivity) disorder, depressive disorders, sleep disorders, cognitive impairment, or obesity.

16. A method for treating substance use disorders, attention deficit (hyperactivity) disorder, depressive disorders, sleep disorders or cognitive impairment or for eliciting a wake-promoting, cognition-enhancing or mood-enhancing effect, comprising:
providing a therapeutically effective amount of a compound or salt of claim 1 to a patient in need of such treatment, optionally in the form of a pharmaceutical composition.

17. A compound or salt of claim 1, wherein $R^6$ and $R^7$ each independently is methyl.

* * * * *